US006358978B1

United States Patent
Ritzeler et al.

(10) Patent No.: US 6,358,978 B1
(45) Date of Patent: Mar. 19, 2002

(54) SUBSTITUTED BENZIMIDAZOLES

(75) Inventors: Olaf Ritzeler, Frankfurt am Main; Hans Ulrich Stilz, Frankfurt; Bernhard Neises, Offenburg, all of (DE); William Jerome Bock, Jr., Tucson, AZ (US); Armin Walser, Tucson, AZ (US); Gary A. Flynn, Tucson, AZ (US); Jörg Habermann, Bad Soden; Gerhard Jähne, Frankurt am Main, both of (DE)

(73) Assignee: Aventis Pharma Deutschland GmbH, Frankfurt (DE)

( * ) Notice: Subject to any disclaimer, the term of this patent is extended or adjusted under 35 U.S.C. 154(b) by 0 days.

(21) Appl. No.: 09/599,390

(22) Filed: Jun. 22, 2000

(30) Foreign Application Priority Data

Jun. 23, 1999 (DE) .......................... 199 28 424
Feb. 12, 2000 (DE) .......................... 100 06 297

(51) Int. Cl.$^7$ .................... A61K 31/445; C07D 243/00; C07D 413/00; C07D 421/00; C07D 235/04
(52) U.S. Cl. ............. 514/319; 514/211.08; 514/211.15; 514/217.03; 514/227.08; 514/233.5; 514/252.06; 514/254.06; 514/256; 514/314; 514/394; 540/553; 540/603; 544/60; 544/132; 544/238; 544/333; 544/366; 546/199; 546/152; 548/304.7
(58) Field of Search .................... 514/319, 211.08, 514/211.15, 217.03, 227.08, 233.5, 252.06, 254.06, 256, 314, 394; 540/553, 603; 544/60, 132, 238, 333, 366; 546/199, 152; 548/304.7

(56) References Cited

U.S. PATENT DOCUMENTS

| | | | |
|---|---|---|---|
| 4,264,325 A | * | 4/1981 | Meyer et al. .................. 8/648 |
| 4,360,679 A | * | 11/1982 | Meyer et al. ............. 548/305.1 |
| 5,741,804 A | | 4/1998 | Keenan et al. .............. 514/394 |
| 5,852,011 A | * | 12/1998 | Matsunaga et al. ....... 514/228.2 |
| 6,114,390 A | * | 9/2000 | Engel et al. ................ 514/595 |

FOREIGN PATENT DOCUMENTS

| | | | |
|---|---|---|---|
| DE | 26-41-060 | * | 3/1978 |
| EP | 0 719 765 A2 | | 7/1996 |
| GB | 2 164 648 A | | 3/1986 |
| WO | WO 94/12478 | | 6/1994 |
| WO | WO 98/05335 | | 2/1998 |

OTHER PUBLICATIONS

Xue et al., "Design, synthesis and in vitro activities of a series of benzimidazole/ . . . " Bioorg. Med. Chem. Lett., (1996), 6(3), pp. 339–344.*

N.M. Akimenko et al., "Interaction Specificity of Benzimidazol Group Compounds with AT–Containing Polynucleotides," *J. Biomol. Struct. Dyn.*, 12(5): 1121–1127 (1995).

W.A. Denny et al., "Potential Antitumor Agents. 59. Structure–Activity Relationships for 2–Phenylbenzimidazole–4–carboxamides, a New Class of 'Minimal' DNA–Intercalating Agents Which May Not Act via Topoisomerase II," *J. Med. Chem.*, 33:814–819 (1990).

H. Göker et al., "Synthesis of 1,2–Disubstituted Benzimidazole–5(6)–Carboxamides and Evaluation of Their Antimicrobial Activity," *Il Farmaco*, 51(1):53–58 (1996).

H. Göker et al., "Synthesis of some new benzimidazolecarboxamides and evaluation of their antimicrobial activity," *Il Farmaco*, 53:415–420 (1998).

C.J. O'Connor et al., "Damage of Egg Phosphatidylcholine Liposomes by DNA–Binding Cytotoxic Agents," *Bull. Chem. Soc. Jpn.*, 64(4):1364–1369 (1991).

M. Rafalski et al., "Synthesis and Biological Evaluation of Substituted Benzimidazoles—Potential GPIIb/IIIa Receptor Antagonists," *Peptides: Chem., Struct. and Bio.: Proceedings of the* 14$^{th}$ *American Peptide Symposium*, 707–708 (P. Kaumaya & R. Hodges eds. 1996).

A.E. Vinogradov et al., "Some Properties of New DNA–Specific Bisbenzimidazole Fluorochromes without a Piperazine Ring," *Bio. & Histochem.*, 68(5):265–270 (1993).

Z. Chen et al., "Site–Specific Phosphorylation of Ikbα by a Novel Ubiquitination–Dependent Protein Kinase Activity," *Cell*, 84:853–862 (1996).

S. Pansare et al., "Synthesis of N–Protected α–Amino Acids from N–(Benzyloxycarbonyl)–L–Serine . . . ," *Org. Synth*, (70), 1ff: 1–9 (1991).

P. Kociénski, "Amino Protecting Groups," *Thieme Verlag*, 185–207 (1994).

P. Stelzel, Methoden der org. Chemie (Methods of Organic Chemistry), vol. 15/1 and 15/2, George Thieme Verlag, Stuttgart, 355–364 (1974).

* cited by examiner

*Primary Examiner*—Richard L. Raymond
*Assistant Examiner*—Tamthom N. Truong
(74) *Attorney, Agent, or Firm*—Finnegan, Henderson, Farabow, Garrett, & Dunner, L.L.P.

(57) ABSTRACT

Compounds of formula I

I

[chemical structure of substituted benzimidazole with substituents $R^1$, $R^2$, $R^3$, $R^4$, $R^5$, $R^6$]

are suitable for the production of pharmaceuticals for the prophylaxis and therapy of disorders in whose course an increased activity of NFκB is involved.

28 Claims, No Drawings

SUBSTITUTED BENZIMIDAZOLES

The invention relates to novel substituted benzimidazoles, a process for their preparation, and use thereof as pharmaceuticals.

The application WO 94/12478 describes, inter alia, benzimidazole derivatives that inhibit blood platelet aggregation.

NFκB is a heterodimeric transcription factor that can activate a large number of genes that code, inter alia, for proinflammatory cytokines such as IL-1, IL-2, TNFα, or IL-6. NFκB is present in the cytosol of cells, complexed with its naturally occurring inhibitor IκB. The stimulation of cells, for example, by cytokines, leads to the phosphorylation and subsequent proteolytic degradation of IκB. This proteolytic degradation leads to the activation of NFκB, which subsequently migrates into the nucleus of the cell and there activates a large number of proinflammatory genes.

In disorders such as rheumatoid arthritis (in the case of inflammation), osteoarthritis, asthma, cardiac infarct, Alzheimer's disease, or atherosclerosis, NFκB is activated beyond the normal extent. The inhibition of NFκB is also of benefit in cancer therapy, since it is employed there for the reinforcement of the cytostatic therapy. It was possible to show that pharmaceuticals such as glucocorticoids, salicylates, or gold salts, which are employed in rheumatic therapy, intervene in an inhibitory manner at various points in the NFκB-activating signal chain or interfere directly with the transcription of the genes.

The first step in the signal cascade mentioned is the degradation of IκB. This phosphorylation is regulated by the specific IκB kinase. To date, no inhibitors are known which specifically inhibit IκB kinase.

In the attempt to obtain active compounds for the treatment of rheumatoid arthritis (in the case of inflammation), osteoarthritis, asthma, cardiac infarct, Alzheimer's disease, carcinomatous disorders (potentiation of cytotoxic therapies), or atherosclerosis, it has now been found that the benzimidazoles according to the invention are strong and very specific inhibitors of IκB kinase.

The invention therefore relates to compounds of formula I

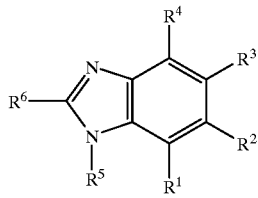

I or a stereoisomeric form of the compound of formula I or a physiologically tolerable salt of the compound of formula I, where one of the substituents $R^1$, $R^2$, $R^3$, and $R^4$ is a radical of formula II

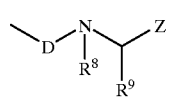

II in which:
D is —C(O)—, —S(O)—, or —S(O)$_2$—;
$R^8$ is hydrogen or (C$_1$–C$_4$)-alkyl;
$R^9$ is (1) a characteristic radical of an amino acid;
(2) aryl, in which aryl is unsubstituted or substituted;
(3) heteroaryl having 5 to 14 ring members, in which the heteroaryl is unsubstituted or substituted;
(4) a heterocycle having 5 to 12 ring members, in which the heterocycle is unsubstituted or substituted;
(5) (C$_1$–C$_6$)-alkyl, in which alkyl is unsubstituted or mono-, di-, or trisubstituted independently of one another by
   (5)(1) aryl, in which aryl is unsubstituted or substituted;
   (5)(2) heteroaryl having 5 to 14 ring members, in which the heteroaryl is unsubstituted or substituted;
   (5)(3) a heterocycle having 5 to 12 ring members, in which the heterocycle is unsubstituted or substituted;
   (5)(4) —O—R$^{11}$;
   (5)(5) =O;
   (5)(6) halogen;
   (5)(7) —CN;
   (5)(8) —CF$_3$;
   (5)(9) —S(O)$_x$—R$^{11}$, in which x is the integer 0, 1, or 2;
   (5)(10) —C(O)—O—R$^{11}$;
   (5)(11) —C(O)—N(R$^{11}$)$_2$;
   (5)(12) —N(R$^{11}$)$_2$;
   (5)(13) (C$_3$–C$_6$)-cycloalkyl;

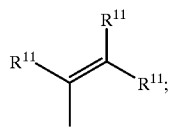

(5)(14) a radical of formula
or
(5)(15) a radical of formula

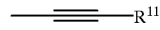

in which
$R^{11}$ is
  (a) hydrogen;
  (b) (C$_1$–C$_6$)-alkyl, in which alkyl is unsubstituted or mono-, di-, or trisubstituted independently of one another by
    (1) aryl, in which aryl is unsubstituted or substituted;
    (2) heteroaryl having 5 to 14 ring members, in which the heteroaryl is unsubstituted or substituted;
    (3) a heterocycle having 5 to 12 ring members, in which the heterocycle is unsubstituted or substituted;
    (4) halogen;
    (5) —N—(C$_1$–C$_6$)$_n$-alkyl, in which n is the integer 0, 1, or 2, and alkyl is unsubstituted or mono-, di-, or trisubstituted independently of one another by halogen or by —COOH;
    (6) —O—(C$_1$–C$_6$)-alkyl; or
    (7) —COOH;
  (c) aryl, in which aryl is unsubstituted or substituted;
  (d) heteroaryl having 5 to 14 ring members, in which the heteroaryl is unsubstituted or substituted; or
  (e) a heterocycle having 5 to 12 ring members, in which the heterocycle is unsubstituted or substituted; and in the case of $(R^{11})_2$, $R^{11}$ independently of one another has the meaning of (a) to (e);

Z is
(1) aryl, in which aryl is unsubstituted or substituted;
(2) heteroaryl having 5 to 14 ring members, in which the heteroaryl is unsubstituted or substituted;
(3) a heterocycle having 5 to 12 ring members, in which the heterocycle is unsubstituted or substituted;
(4) —$(C_1-C_6)$-alkyl, in which alkyl is substituted or unsubstituted independently of one another by
  (4)(1) aryl, in which aryl is unsubstituted or substituted;
  (4)(2) heteroaryl having 5 to 14 ring members, in which the heteroaryl is unsubstituted or substituted;
  (4)(3) a heterocycle having 5 to 12 ring members, in which the heterocycle is unsubstituted or substituted;
  (4)(4) halogen;
  (4)(5) —N—$(C_1-C_6)_n$-alkyl, in which n is the integer 0, 1, or 2, and alkyl is unsubstituted or mono-, di-, or trisubstituted independently of one another by halogen or by —COOH;
  (4)(6) —O—$(C_1-C_6)$-alkyl; or
  (4)(7) —COOH; or
(5) —C(O)—$R^{10}$, in which
  $R^{10}$ is
    (1) —O—$R^{11}$; or
    (2) —N$(R^{11})_2$;
    in which $R^{11}$ is as defined above; or $R^8$ and $R^9$, together with the nitrogen and carbon to which they are each bonded, form a heterocyclic ring of formula IIa

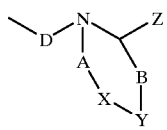

IIa in which:
D, Z, and $R^{10}$ are as defined in formula II;
A is nitrogen or —$CH_2$—;
B is oxygen, sulfur, nitrogen, or —$CH_2$—;
X is oxygen, sulfur, nitrogen, or —$CH_2$—;
Y is absent or is oxygen, sulfur, nitrogen, or —$CH_2$—; or
X and Y together form a phenyl, 1,2-diazine, 1,3-diazine, or a 1,4-diazine radical;
  where the ring system formed by N, A, X, Y, B, and the carbon contains no more than one oxygen; X is not oxygen, sulfur, or nitrogen if A is nitrogen; contains no more than one sulfur; contains 1, 2, 3, or 4 nitrogens; and where oxygen and sulfur do not occur at the same time;
  where the ring system formed by N, A, X, Y, B, and the carbon is unsubstituted or mono-, di-, or trisubstituted independently of one another by $(C_1-C_8)$-alkyl, in which alkyl is straight-chain or branched and is unsubstituted or mono- or disubstituted by
    (1)(1) —OH;
    (1)(2) $(C_1-C_8)$-alkoxy, in which alkoxy is straight-chain or branched;
    (1)(3) halogen;
    (1)(4) —$NO_2$;
    (1)(5) —$NH_2$;
    (1)(6) —$CF_3$;
    (1)(7) —OH;
    (1)(8) methylenedioxy;
    (1)(9) —C(O)—$CH_3$;
    (1)(10) —CH(O);
    (1)(11) —CN;
    (1)(12) —COOH;
    (1)(13) —C(O)—$NH_2$;
    (1)(14) $(C_1-C_4)$-alkoxycarbonyl, in which alkoxycarbonyl is straight-chain or branched;
    (1)(15) phenyl;
    (1)(16) phenoxy;
    (1)(17) benzyl;
    (1)(18) benzyloxy; or
    (1)(19) tetrazolyl; or $R^9$ and Z together with the carbons to which they each are bonded form a heterocyclic ring of formula IIc

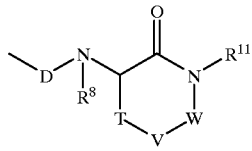

IIc in which:
D, $R^8$, and $R^{11}$ are as defined in formula II;
T is oxygen, sulfur, nitrogen, or —$CH_2$—;
W is oxygen, sulfur, nitrogen, or —$CH_2$—;
V is absent or is oxygen, sulfur, nitrogen, or —$CH_2$—; or
T and V together form a phenyl, 1,2-diazine, 1,3-diazine, or a 1,4-diazine radical; or
V and W together form a phenyl, 1,2-diazine, 1,3-diazine, or a 1,4-diazine radical;
  where the ring system formed by N, T, V, W, and the two carbons contains no more than one oxygen, no more than one sulfur, and 1, 2, 3, or 4 nitrogen; where oxygen and sulfur do not occur at the same time; and where the ring system formed by N, T, V, W, and the two carbons is unsubstituted or mono-, di-, or trisubstituted independently of one another by the substituents defined above under (1)(1) to (1)(19); and
the other substituents $R^1$, $R^2$, $R^3$, and $R^4$ are chosen independently of one another, and are
(1) hydrogen;
(2) halogen;
(3) $(C_1-C_4)$-alkyl;
(4) heteroaryl having 5 to 14 ring members, in which the heteroaryl is unsubstituted or substituted;
(5) a heterocycle having 5 to 12 ring members, in which the heterocycle is unsubstituted or substituted;
(6) $(C_1-C_6)$-alkyl;
(7) —CN;
(8) —$NO_2$;
(9) —O—$(C_0-C_4)$-alkyl-aryl, in which alkyl is straight-chain or branched;
(10) —O—$(C_1-C_4)$-alkyl;
(11) —$OR^{11}$;
(12) —$N(R^{11})_2$;
(13) —$S(O)_x$—$R^{11}$, in which x is the integer 0, 1, or 2; or
(14) —$CF_3$;
  in which $R^{11}$ is as defined above;

$R^5$ is
- (1) hydrogen;
- (2) —OH; or
- (3) =O; and $R^6$ is
- (1) aryl, in which aryl is unsubstituted or substituted;
- (2) phenyl, mono- or disubstituted independently of one another by
  - (2)(1) —CN;
  - (2)(2) —NO$_2$;
  - (2)(3) —O—(C$_1$-C$_4$)-alkyl;
  - (2)(4) —N(R$^{11}$)$_2$;
  - (2)(5) —NH—C(O)—R$^{11}$;
  - (2)(6) —S(O)$_x$—R$^{11}$, in which x is the integer 0, 1, or 2;
  - (2)(7) —C(O)—R$^{11}$; or
  - (2)(8) —(C$_1$-C$_4$)-alkyl—NH$_2$;
    in which R$^{11}$ is as defined above;
- (3) heteroaryl having 5 to 14 ring members, in which the heteroaryl is unsubstituted or substituted; or
- (4) a heterocycle having 5 to 12 ring members, in which the heterocycle is unsubstituted or substituted.

A preferred compound of formula I is one where one of the substituents $R^1$, $R^2$, $R^3$, and $R^4$ is a radical of formula II in which $R^8$ is hydrogen;

$R^9$ is
- (1) a characteristic radical of an amino acid; or
- (2) (C$_1$-C$_6$)-alkyl, in which alkyl is unsubstituted or mono- or disubstituted independently of one another by at least one radical selected from pyrrole, pyrrole mono- or disubstituted independently of one another by —(C$_1$-C$_4$)-alkyl, pyrazole, phenyl, imidazole, triazole, thiophene, thiazole, oxazole, isoxazole, pyridine, pyrimidine, indole, benzothiophene, benzimidazole, benzoxazole, benzothiazole, azetidine, pyrroline, pyrrolidine, piperidine, isothiazole, diazepine, thiomorpholine, —CN, morpholine, azepine, pyrazine, 1,3,4-oxadiazole, —N(R$^{13}$)-phenyl, wherein R$^{13}$ is defined below, (C$_3$-C$_6$)-cycloalkyl, —OR$^{11}$, —NH(R$^{11}$), in which R$^{11}$ is as defined above, —S(O)$_x$—R$^{12}$, in which x is the integer 0, 1, or 2, and R$^{12}$ is naphthyl, pyrimidinyl, morpholinyl, or phenyl, which are unsubstituted or mono- or disubstituted independently of one another by —OH, (C$_1$-C$_4$)-alkyl, —CF$_3$, halogen, —O—(C$_1$-C$_4$)-alkyl, —COOH, —C(O)—O—(C$_1$-C$_4$)-alkyl, —NH$_2$, or —NH—C(O)—(C$_1$-C$_4$)-alkyl, or C(O)—R$^{12}$, in which R$^{12}$ is as defined above;

Z is —C(O)—R$^{10}$, tetrazole, (C$_1$-C$_6$)-alkyl, in which alkyl is unsubstituted or mono- or disubstituted independently of one another by phenyl or —OH, or 1,3,4-oxadiazole, in which 1,3,4-oxadiazole is unsubstituted or monosubstituted by
—NH$_2$, —NH(C$_1$-C$_4$)-alkyl, —N—[(C$_1$-C$_4$)-alkyl]$_2$, —NH—C(O)—(C$_1$-C$_4$)-alkyl, —NH—C(O)—NH—(C$_1$-C$_4$)-alkyl, –NH–C(O)–NH–(C$_3$–C$_7$)-cycloalkyl, —NH—C(O)—NH-aryl, —NH—C(O)—NH-phenyl, —NH—SO$_2$-aryl, —NH—SO$_2$—(C$_1$-C$_4$)-alkyl, —OH, or —(C$_1$-C$_4$)-alkyl, in which R$^{10}$ is —O—R$^{11}$, phenyl, pyrimidine, —OH, morpholinyl, —N(R$^{11}$)$_2$, or —NH$_2$;

$R^{11}$ is
- (1) —(C$_1$-C$_4$)-alkyl;
- (2) R$^{13}$; or
- (3) —N(R$^{13}$)$_2$, in which $R^{13}$ independently of one another is
- (a) hydrogen;
- (b) —(C$_1$-C$_6$)-alkyl;
- (c) —(C$_1$-C$_4$)-alkyl—O—(C$_1$-C$_4$)-alkyl;
- (d) —(C$_1$-C$_6$)-alkyl—N(R$^{13}$)$_2$;
- (e) halogen; or
- (f) —(C$_0$-C$_4$)-alkyl, mono- or disubstituted by aryl, imidazolyl, morpholinyl, or phenyl; or $R^8$ and $R^9$, together with the nitrogen and carbon to which they are each bonded, form a ring of formula IIa selected from pyrrole, pyrroline, pyrrolidine, pyridine, piperidine, piperylene, pyridazine, pyrimidine, pyrazine, piperazine, pyrazole, imidazole, pyrazoline, imidazoline, pyrazolidine, imidazolidine, oxazole, isoxazole, 2-isoxazolidine, isoxazolidine, morpholine, isothiazole, thiazole, tetrazole, 1,2,3,5-oxathiadiazole-2-oxides, oxadiazolones, isoxazolones, triazolones, oxadiazolidinediones, triazoles which are substituted by F, CN, CF$_3$, or COO—(C$_1$-C$_4$)-alkyl, 3-hydroxypyrro-2,4-diones, 5-oxo-1,2,4-thiadiazoles, 1,3,4-oxadiazole, isothiazolidine, thiomorpholine, indazole, thiadiazole, benzimidazole, quinoline, triazole, phthalazine, quinazoline, quinoxaline, purine, pteridine, indole, tetrahydroquinoline, tetrahydroisoquinoline, and isoquinoline; or $R^9$ and Z, together with the carbons to which they are each bonded, form a ring of formula IIc selected from pyrrole, pyrroline, pyrrolidine, pyridine, piperidine, piperylene, pyridazine, pyrimidine, pyrazine, piperazine, pyrazole, imidazole, pyrazoline, imidazoline, pyrazolidine, imidazolidine, oxazole, isoxazole, 2-isoxazolidine, isoxazolidine, morpholine, isothiazole, thiazole, isothiazolidine, thiomorpholine, indazole, thiadiazole, benzimidazole, quinoline, triazole, phthalazine, quinazoline, quinoxaline, purine, pteridine, indole, tetrahydroquinoline, tetrahydroisoquinoline, isoquinoline, tetrazole, 1,2,3,5-oxathiadiazole-2-oxides, oxadiazolones, isoxazolones, triazolones, oxadiazolidinediones, triazoles which are substituted by F, CN, CF$_3$, or COO—(C$_1$-C$_4$)-alkyl, 3-hydroxypyrrole-2,4-diones, 1,3,4-oxadiazole, and 5-oxo-1,2,4-thiadiazoles; and the other substituents $R^1$, $R^2$, $R^3$, and $R^4$ are chosen independently of one another, and are
- (1) hydrogen;
- (2) halogen;
- (3) (C$_1$-C$_4$)-alkyl;
- (4) —CN;
- (5) —NO$_2$;
- (6) —O—(C$_0$-C$_4$)-alkyl-aryl, in which alkyl is straight-chain or branched;
- (7) —O—(C$_1$-C$_4$)-alkyl;
- (8) —N—(C$_0$-C$_4$)-alkyl-aryl, in which alkyl is straight-chain or branched;
- (9) —N—(C$_1$-C$_4$)-alkyl; or
- (10) —CF$_3$;

$R^5$ is
- (1) hydrogen;
- (2) —OH; or
- (3) =O; and $R^6$ is
- (1) phenyl, mono- or disubstituted independently of one another by
  - (1)(1) —CN;
  - (1)(2) —NO$_2$;
  - (1)(3) —O—(C$_1$-C$_4$)-alkyl;

(1)(4) —NH$_2$; or (1)(5) —(C$_1$–C$_4$)-alkyl—NH$_2$;

(2) heteroaryl having 5 to 14 ring members, in which the heteroaryl is unsubstituted or mono-, di-, or trisubstituted independently of one another by —N—R$^{14}$, in which R$^{14}$ is —(C$_1$–C$_6$)-alkyl, —(C$_3$–C$_6$)-cycloalkyl, phenyl, halogen, —OH, or —(C$_1$–C$_4$)-alkyl; or (3) a heterocycle having 5 to 12 ring members, in which the heterocycle is unsubstituted or mono-, di-, or trisubstituted independently of one another by —N—R$^{14}$, in which R$^{14}$ is —(C$_1$–C$_6$)-alkyl, —(C$_3$–C$_6$)-cycloalkyl, phenyl, halogen, –OH, or —(C$_1$–C$_4$)-alkyl.

The term "halogen" is understood as meaning fluorine, chlorine, bromine, or iodine. The term "(C$_1$–C$_4$)-alkyl" is understood as meaning hydrocarbon radicals whose carbon chain is straight-chain or branched and contains 1 to 4 carbon atoms. The term "(C$_1$–C$_6$)-alkyl" is understood as meaning hydrocarbon radicals whose carbon chain is straight-chain or branched and contains 1 to 6 carbon atoms. The term "Co-alkyl" is understood as meaning a covalent bond. Cyclic alkyl radicals are, for example, 3- to 6-membered monocyclic systems such as cyclopropyl, cyclobutyl, cyclopentyl, or cyclohexyl.

The expression "R$^8$ and R$^9$, together with the nitrogen atom and carbon atom to which they are each bonded, form a heterocyclic ring of formula IIa" is understood as meaning radicals which are derived from pyrrole, pyrroline, pyrrolidine, imidazole, pyrazole, oxazole, tetrazole, 1,2,3,5-oxathiadiazole-2-oxides, triazolones, oxadiazolones, isoxazolones, 1,3,4-oxadiazole, oxadiazolidinediones, triazoles which are substituted by F, CN, CF$_3$, or COO—(C$_1$–C$_4$)-alkyl, 3-hydroxypyrrole-2,4-diones, 5-oxo-1,2,4-thiadiazoles, isoxazole, indole, isoxazoline, isoxazolidine, morpholine, thiazole, isothiazole, isothiazoline, purine, isothiazolidine, thiomorpholine, pyridine, piperidine, pyrazine, piperazine, pyrimidine, pyridazine, isoindole, indazole, benzimidazole, phthalazine, quinoline, isoquinoline, quinoxaline, quinazoline, cinnoline, pteridine, imidazolidine, carboline, and benzo-fused derivatives of these heterocycles.

The term "aryl" is understood as meaning aromatic hydrocarbon radicals having 6 to 14 carbon atoms in the ring. (C$_6$–C$_{14}$)-Aryl radicals are, for example, phenyl, naphthyl, for example, 1-naphthyl, 2-naphthyl, biphenylyl, for example, 2-biphenylyl, 3-biphenylyl, and 4-biphenylyl, anthryl, or fluorenyl. Biphenylyl radicals, naphthyl radicals, and, in particular, phenyl radicals are preferred aryl radicals. Aryl radicals, in particular phenyl radicals, can be monosubstituted or polysubstituted, preferably monosubstituted, disubstituted, or trisubstituted, by identical or different radicals, preferably by radicals selected from (C$_1$–C$_8$)-alkyl, in particular (C$_1$–C$_4$)-alkyl, (C$_1$–C$_8$)-alkoxy, in particular (C$_1$–C$_4$)-alkoxy, halogen, nitro, amino, trifluoromethyl, hydroxyl, hydroxy-(C$_1$–C$_4$)-alkyl such as hydroxymethyl, 1-hydroxyethyl, or 2-hydroxyethyl, methylenedioxy, ethylenedioxy, formyl, acetyl, cyano, hydroxycarbonyl, aminocarbonyl, (C$_1$–C$_4$)-alkoxycarbonyl, phenyl, phenoxy, benzyl, benzyloxy, or tetrazolyl. Further, when aryl is phenyl, phenyl is optionally mono- or disubstituted independently of one another by —CN, —NO$_2$, —O—(C$_1$–C$_4$)-alkyl, —N(R$^{11}$)$_2$, —NH—C(O)—R$^{11}$, —S(O)$_x$R$^1$, in which x is the integer 0, 1, or 2, —C(O)—R$^{11}$, in which R$^{11}$ is as defined above, or —(C$_1$–C$_4$)-alkyl—NH$_2$. The same applies, for example, to radicals such as arylalkyl or arylcarbonyl. Arylalkyl radicals are, in particular, benzyl and also 1- and 2-naphthylmethyl, 2-, 3-, and 4-biphenylylmethyl, and 9-fluorenylmethyl. Substituted arylalkyl radicals are, for example, benzyl radicals and naphthylmethyl radicals substituted in the aryl moiety by one or more (C$_1$–C$_8$)-alkyl radicals, in particular (C$_1$–C$_4$)-alkyl radicals, for example, 2-, 3-, and 4-methylbenzyl, 4-isobutylbenzyl, 4-tert-butylbenzyl, 4-octylbenzyl, 3,5-dimethylbenzyl, pentamethylbenzyl, 2-, 3-, 4-, 5-, 6-, 7-, and 8-methyl-1-naphthylmethyl, 1-, 3-, 4-, 5-, 6-, 7-, and 8-methyl-2-naphthylmethyl, by one or more (C$_1$–C$_8$)-alkoxy radicals, in particular (C$_1$–C$_4$)-alkoxy radicals, benzyl radicals, and naphthylmethyl radicals substituted in the aryl moiety, for example, 4-methoxybenzyl, 4-neopentyloxybenzyl, 3,5-dimethoxybenzyl, 3,4-methylenedioxybenzyl, 2,3,4-trimethoxybenzyl, nitrobenzyl radicals, for example, 2-, 3-, and 4-nitrobenzyl, halobenzyl radicals, for example, 2-, 3-, and 4-chloro- and 2-, 3-, and 4-fluorobenzyl, 3,4-dichlorobenzyl, pentafluorobenzyl, trifluoromethylbenzyl radicals, for example, 3- and 4-trifluoromethylbenzyl, or 3,5-bis(trifluoromethyl)benzyl.

In monosubstituted phenyl radicals, the substituent can be located in the 2-position, the 3-position, or the 4-position. Disubstituted phenyl can be substituted in the 2,3-position, the 2,4-position, the 2,5-position, the 2,6-position, the 3,4-position, or the 3,5-position. In trisubstituted phenyl radicals, the substituents can be located in the 2,3,4-position, the 2,3,5-position, the 2,4,5-position, the 2,4,6-position, the 2,3,6-position, or the 3,4,5-position.

The explanations for the aryl radicals apply accordingly to divalent arylene radicals, for example, to phenylene radicals that can be present, for example, as 1,4-phenylene or as 1,3-phenylene.

Phenylene-(C$_1$–C$_6$)-alkyl is in particular phenylenemethyl (—C$_6$H$_4$–CH$_2$—) and phenyleneethyl. (C$_1$–C$_6$)-Alkylenephenyl is in particular methylenephenyl (—CH$_2$–C$_6$H$_4$—). Phenylene-(C$_2$–C$_6$)-alkenyl is in particular phenyleneethenyl and phenylenepropenyl.

The expression "heteroaryl having 5 to 14 ring members" represents a radical of a monocyclic or polycyclic aromatic system having 5 to 14 ring members, which contains 1, 2, 3, 4, or 5 heteroatoms as ring members. Examples of heteroatoms are N, O, and S. If a number of heteroatoms are contained, these can be identical or different. Heteroaryl radicals can likewise be monosubstituted or polysubstituted, preferably monosubstituted, disubstituted, or trisubstituted, by identical or different radicals selected from (C$_1$–C$_8$)-alkyl, in particular (C$_1$–C$_4$)-alkyl, (C$_1$–C$_8$)-alkoxy, in particular (C$_1$–C$_4$)-alkoxy, halogen, nitro, —N(R$^{11}$)$_2$, trifluoromethyl, hydroxyl, hydroxy-(C$_1$–C$_4$)-alkyl such as hydroxymethyl, 1-hydroxyethyl, or 2-hydroxyethyl, methylenedioxy, formyl, acetyl, cyano, hydroxycarbonyl, aminocarbonyl, (C$_1$–C$_4$)-alkoxycarbonyl, phenyl, phenoxy, benzyl, benzyloxy, or tetrazolyl. Heteroaryl having 5 to 14 ring members preferably represents a monocyclic or bicyclic aromatic radical which contains 1, 2, 3, or 4, in particular 1, 2, or 3, identical or different heteroatoms selected from N, O, and S, and which can be substituted by 1, 2, 3, or 4, in particular 1, 2, or 3, identical or different substituents selected from (C$_1$–C$_6$)-alkyl, (C$_1$–C$_6$)-alkoxy, fluorine, chlorine, nitro, —N(R$^{11}$)$_2$, trifluoromethyl, hydroxyl, hydroxy-(C$_1$–C$_4$)-alkyl, (C$_1$–C$_4$)-alkoxycarbonyl, phenyl, phenoxy, benzyloxy, and benzyl. Heteroaryl particularly preferably represents a monocyclic or bicyclic aromatic radical having 5 to 10 ring members, in particular a 5-membered or 6-membered monocyclic aromatic radical which contains 1, 2, or 3, in particular 1 or 2, identical or different heteroatoms selected from N, O, and S, and can be substituted by 1 or 2 identical or different substituents selected from $(C_1-C_4)$-alkyl, halogen, hydroxyl, —$N(R^{11})_2$, $(C_1-C_4)$-alkoxy, phenyl, phenoxy, benzyloxy, and benzyl. $R^{11}$ is as defined in substituent $R^9$ of formula I.

The expression "heterocycle having 5 to 12 ring members" represents a monocyclic or bicyclic 5-membered to 12-membered heterocyclic ring that is partly saturated or completely saturated. Examples of heteroatoms are N, O, and S. The heterocycle is unsubstituted or substituted on one or more carbons or on one or more heteroatoms by identical or different substituents. These substituents have been defined above for the radical heteroaryl. In particular, the heterocyclic ring is monosubstituted or polysubstituted, for example, monosubstituted, disubstituted, trisubstituted, or tetrasubstituted, on carbons by identical or different radicals selected from $(C_1-C_8)$-alkyl, for example, $(C_1-C_4)$-alkyl, $(C_1-C_8)$-alkoxy, for example, $(C_1-C_4)$-alkoxy such as methoxy, phenyl-$(C_1-C_4)$-alkoxy, for example, benzyloxy, hydroxyl, oxo, halogen, nitro, amino, or trifluoromethyl, and/or it is substituted on the ring nitrogens in the heterocyclic ring by $(C_1-C_8)$-alkyl, for example, $(C_1-C_4)$-alkyl such as methyl or ethyl, by optionally substituted phenyl or phenyl-$(C_1-C_4)$-alkyl, for example, benzyl. Nitrogen heterocycles can also be present as N-oxides or as quaternary salts.

Examples of the expressions heteroaryl having 5 to 14 ring members or heterocycle having 5 to 12 ring members are radicals which are derived from pyrrole, furan, thiophene, imidazole, pyrazole, oxazole, isoxazole, thiazole, isothiazole, tetrazole, 1,3,4-oxadiazole, 1,2,3,5-oxathiadiazole-2-oxides, triazolones, oxadiazolones, isoxazolones, oxadiazolidinediones, triazoles which are substituted by F, CN, $CF_3$, or COO—$(C_1-C_4)$-alkyl, 3-hydroxypyrrole-2,4-diones, 5-oxo-1,2,4-thiadiazoles, pyridine, pyrazine, pyrimidine, indole, isoindole, indazole, phthalazine, quinoline, isoquinoline, quinoxaline, quinazoline, cinnoline, carboline, and benzo-fused, cyclopenta-, cyclohexa-, or cyclohepta-fused derivatives of these heterocycles. Particularly preferred radicals are 2- or 3-pyrrolyl, phenylpyrrolyl such as 4- or 5-phenyl-2-pyrrolyl, 2-furyl, 2-thienyl, 4-imidazolyl, methylimidazolyl, for example, 1-methyl-2-, 4-, or -5-imidazolyl, 1,3-thiazol-2-yl, 2-pyridyl, 3-pyridyl, 4-pyridyl, 2-, 3-, or 4-pyridyl-N-oxide, 2-pyrazinyl, 2-, 4-, or 5-pyrimidinyl, 2-, 3-, or 5-indolyl, substituted 2-indolyl, for example, 1-methyl-, 5-methyl-, 5-methoxy-, 5-benzyloxy-, 5-chloro-, or 4,5-dimethyl-2-indolyl, 1-benzyl-2- or -3-indolyl, 4,5,6,7-tetrahydro-2-indolyl, cyclohepta[b]-5-pyrrolyl, 2-, 3-, or 4-quinolyl, 1-, 3-, or 4-isoquinolyl, 1-oxo-1,2-dihydro-3-isoquinolyl, 2-quinoxalinyl, 2-benzofuranyl, 2-benzothienyl, 2-benzoxazolyl, or benzothiazolyl, or dihydropyridinyl, pyrrolidinyl, for example, 2- or 3-(N-methylpyrrolidinyl), piperazinyl, morpholinyl, thiomorpholinyl, tetrahydrothienyl, or benzodioxolanyl.

The structural formula of α-amino acids is as follows:

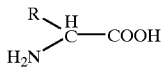

The α-amino acids differ from one another by the radical R, which in the context of the present application is described as a "characteristic radical" of an amino acid.

In the case where $R^9$ is the characteristic radical of an amino acid, the characteristic radicals employed are preferably those of the following naturally occurring α-amino acids: glycine, alanine, valine, leucine, isoleucine, phenylalanine, tyrosine, tryptophan, serine, threonine, cysteine, methionine, asparagine, glutamine, lysine, histidine, arginine, glutamic acid, and aspartic acid. Those particularly preferred are histidine, tryptophan, serine, threonine, cysteine, methionine, asparagine, glutamine, lysine, arginine, glutamic acid, and aspartic acid. Preferred characteristic radicals of an amino acid which are furthermore employed as the radical $R^9$ are also non-naturally occurring amino acids such as 2-aminoadipic acid, 2-aminobutyric acid, 2-aminoisobutyric acid, 2,3-diaminopropionic acid, 2,4-diaminobutyric acid, 1,2,3,4-tetrahydroisoquinoline-1-carboxylic acid, 1,2,3,4-tetrahydroisoquinoline-3-carboxylic acid, 2-aminopimelic acid, 2-amino-3-phenylaminoethyl-propionic acid, 2-amino-3-phenylamino-propionic acid, phenylglycine, 3-(2-thienyl)alanine, 3-(3-thienyl)alanine, 2-(2-thienyl)glycine, 2-aminoheptanoic acid, pipecolic acid, hydroxylysine, sarcosine, N-methylisoleucine, 6-N-methyllysine, N-methylvaline, norvaline, norleucine, ornithine, allo-isoleucine, allo-threonine, allo-hydroxylysine, 4-hydroxyproline, 3-hydroxyproline, 3-(2-naphthyl)alanine, 3-(1-naphthylalanine), homophenylalanine, homocysteine, homocysteic acid, homotryptophan, cysteic acid, 3-(2-pyridyl)alanine, 3-(3-pyridyl)alanine, 3-(4-pyridyl)alanine, phosphinothricin, 4-fluorophenylalanine, 3-fluorophenylalanine, 4-fluorophenylalanine, 3-fluorophenylalanine, 3-fluorophenylalanine, 2-fluorophenylalanine, 4-chlorophenylalanine, 4-nitrophenylalanine, 4-aminophenylalanine, cyclohexylalanine, citrulline, 5-fluorotryptophan, 5-methoxytryptophan, methionine sulfone, methionine sulfoxide, or —NH—$NR^{11}$—$CON(R^{11})_2$, which are optionally also substituted. In the case of natural but also of non-naturally occurring amino acids that have a functional group such as amino, hydroxyl, carboxyl, mercapto, guanidyl, imidazolyl, or indolyl, this group can also be protected.

Suitable protective groups for this are preferably the N-protective groups customarily used in peptide chemistry, for example, protective groups of the urethane type, benzyloxycarbonyl (Z), t-butoxycarbonyl (Boc), 9-fluorenyloxycarbonyl (Fmoc), allyloxycarbonyl (Aloc), or of the acid amide type, in particular formyl, acetyl, or trifluoroacetyl, and of the alkyl type, for example, benzyl. In the case of an imidazole radical in $R^9$, for example, the sulfonic acid derivative of formula IV employed for the sulfonamide formation is used as a protective group of the imidazole nitrogen, which can be removed again, in particular in the presence of bases such as sodium hydroxide solution.

The term "independently of one another" is understood as meaning that the radicals selected are independent of one another and can be identical or different. For example, two radicals substituted independently of one another by A and B means that one radical may be A and the other may be B, both radicals may be A, or both radicals may be B.

The starting substances for the chemical reactions are known or can be easily prepared by methods known from the literature.

The invention further relates to a process for the preparation of compounds of formula I or a stereoisomeric form of compounds of formula I or of a physiologically tolerable salt of compounds of formula I, comprising a) reacting a compound of formula IV

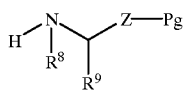

IV in which Pg is a suitable protective group (e.g., methyl ester), an amide group, or a hydroxyl group, and Z, $R^8$, and $R^9$ are as defined in formula II, with an acid chloride or an activated ester of the compound of formula III

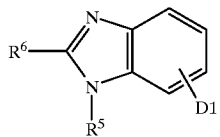

III where D1 is —COOH or sulfonylhalogen, and $R^5$ and $R^6$ are as defined in formula I, in the presence of a base or, if appropriate, of a dehydrating agent in solution and, after removal of the protective group, converting into a compound of formula I, or b) reacting a compound of formula IVa

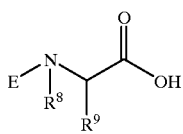

IVa in which $R^8$ and $R^9$ are as defined in formula II, and E is an N-amino protective group, with its carboxyl group coupled via an intermediate chain L to a polymeric resin of formula PS, a compound of formula V

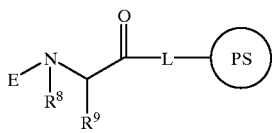

V resulting, which, after selective removal of the protective group E, is reacted with a compound of formula III, where $R^5$ and $R^6$ are as defined in formula I, in the presence of a base or, if appropriate, of a dehydrating agent to give a compound of formula VI

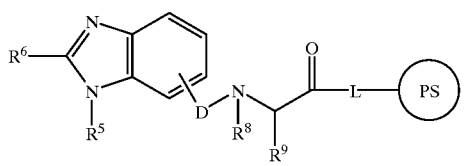

VI and converting the compound of formula VI, after removal of the support material, into a compound of formula I, or c) reacting a compound of formula V, after selective removal of the protective group E, with a compound of formula VII

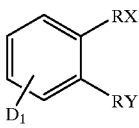

VII where $D_1$ is —COOH or sulfonylhalogen, and RX is halogen and RY is a radical —$NO_2$ or —NH—E, and E is a protective group, to give a compound of formula VIII

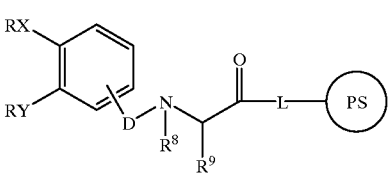

VIII and then reacting the compound of formula VIII with a compound of formula IX

IX in which $R^6$ is as defined in the compound of formula I, to give an intermediate compound of formula VIa

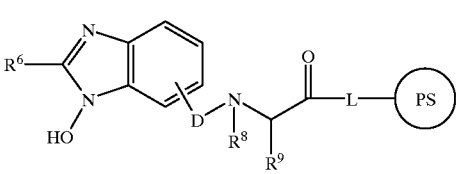

VIa then either converting the intermediate compound of formula VIa into a compound of formula I after removal of the support material or reducing it, for example, with tributylphosphine, to give a compound of formula VI and converting into a compound of formula I after removal of the support material, or d) converting a compound of formula I into a physiologically tolerable salt.

In process variant a) of the general working procedure, the acid functions of compounds of formula IVa are provided with a protective group Pg; this selective carboxylic acids derivatization is carried out according to methods such as are described in Houben-Weyl, *Methoden der Org. Chemie* (Methods of Organic Chemistry), Vol. 15/1. In process variant b) of the general working procedure, the amino functions of the starting compounds of formula IVa are provided with a protective group E; this selective amino groups derivatization is carried out according to methods such as are described in Houben-Weyl, *Methoden der Org. Chemie* (Methods of Organic Chemistry), Vol. 15/1.

A suitable protective group Pg preferably used for this is the carboxyl protective groups customary in peptide chemistry, for example, protective groups of the alkyl ester type, such as methyl, ethyl, tert-butyl, isopropyl, benzyl, fluorenylmethyl, or allyl, aryl ester type, such as phenyl, or amide type, such as amide or benzhydrylamine. Suitable protective groups E used for this are preferably the N-protective groups customary in peptide chemistry, for example, protective groups of the urethane type, such as benzyloxycarbonyl (Z), t-butoxycarbonyl (Boc), 9-fluorenylmethoxycarbonyl (Fmoc), and allyloxycarbonyl (Aloc), or of the acid amide type, in particular formyl, acetyl, or trifluoroacetyl of alkyl type such as benzyl.

The (trimethylsilyl)ethoxycarbonyl (Teoc) group has also proven particularly suitable for this (P. Kociēnski, Protecting Groups, Thieme Verlag (1994)).

Starting materials used for the preparation of the benzimidazole derivatives of formula III are preferably 2,3- and 3,4-diaminobenzoic acids and aryl- or heteroarylaldehydes, which are reacted at 145° C. in the presence of nitrobenzene as a solvent. The acids mentioned are furthermore reacted with methyl or ethyl imidates, which are prepared from the corresponding arylnitriles or heteroarylnitriles in a Pinner reaction.

For the condensation of compounds of formula IV with those of formula III, the coupling methods which are well-known per se to the person skilled in the art are advantageously used (see, for example, Houben-Weyl, *Methoden der Org. Chemie* (Methods of Organic Chemistry]), Vol. 15/1 and 15/2, Georg Thieme Verlag, Stuttgart (1974)). Suitable condensing agents or coupling reagents are compounds such as carbonyldiimidazole, carbodiimides such as dicyclohexylcarbodiimide or diisopropylcarbodiimide (DIC), O-((cyano(ethoxycarbonyl)methylene)amino)-N,N, N',N'-tetramethyluronium tetrafluoroborate (TOTU), or propanephosphonic anhydride (PPA).

The condensations can be carried out under standard conditions. During the condensation, as a rule it is necessary for the non-reacting amino groups present to be protected by reversible protective groups. The same applies to carboxyl groups not involved in the reaction, which during the condensation are preferably present as ($C_1$–$C_6$)-alkyl esters, benzyl esters, or tert-butyl esters. Amino group protection is unnecessary if the amino groups are still present in the form of precursors such as nitro groups or cyano groups and are only formed by hydrogenation after the condensation. After the condensation, the protective groups present are removed in a suitable manner. For example, $NO_2$ groups (guanidino protection in amino acids), benzyloxycarbonyl groups, and benzyl groups in benzyl esters can be removed by hydrogenation. The protective groups of the tert-butyl type are removed using acid, while the 9-fluorenylmethoxycarbonyl radical is removed by secondary amines.

The polymeric support designated in formulae V and VI by PS is a crosslinked polystyrene resin having a linker designated as the intermediate chain L. This linker carries a suitable functional group, for example, amine, known, for example, as Rink amide resin, or an OH group, known, for example, as Wang resin or Kaiser's oxime resin. Alternatively, other polymeric supports such as glass, cotton, or cellulose having various intermediate chains L can be employed.

The intermediate chain designated by L is covalently bonded to the polymeric support and allows a reversible, amide-like or ester-like bond with the compound of formula IVa, which remains stable during the further reaction on the bonded compound of formula IVa; but under strongly acidic reaction conditions, e.g., mixtures with trifluoroacetic acid, releases the group located on the linker again. The release of the desired compound of formula I from the linker can be carried out at various positions in the reaction sequence.

A. General procedure for the coupling of protected aminocarboxylic acids of formula IVa to the solid support according to process variant b) in the general working procedure:

The synthesis was carried out in reactors each having a reaction volume of 15 ml. Each of the reactors was filled with 0.179 g of Rink amide AM resin (Fmoc-Rink amide AM/Nova-Biochem; loading 0.56 mmol/g; i.e., 0.1 mmol/reactor). For the removal of the Fmoc protective group from the resin, a 30% strength piperidine/DMF solution was metered into each reactor and the mixture was shaken for 45 minutes (min). It was then filtered and the resin was washed three times with dimethylformamide (DMF).

For the coupling of the protected amino acid, a 0.5 molar solution of the corresponding Fmoc-amino acid (0.3 mmol in DMF), a solution of HOBt (0.33 mmol in DMF), and a solution of DIC (0.33 mmol in DMF) were each added to the resin thus prepared and the mixture was shaken at 35° C. for 16 hours (h). The resin was then washed with DMF a number of times.

To check the coupling, a few resin beads were removed and subjected to a KAISER test; in all cases the test was negative.

The removal of the Fmoc protective group was carried out, as mentioned above, using 30% strength piperidine/DMF solution.

For the coupling of the benzimidazolecarboxylic acids, a 0.1 molar solution of the corresponding 4- or 5-substituted acid (0.4 mmol in DMF), a 0.5 molar solution of the coupling reagent TOTU (0.44 mmol in DMF), and a 0.5 molar solution of DIPEA (0.6 mmol in DMF) were added and the mixture was shaken at 40° C. for 16 h. It was then washed a number of times with DMF.

To check the reaction, a few beads of resin were again removed and subjected to a KAISER test.

For the removal of the desired substances from the solid support, the resin was washed a number of times with dichloromethane. The cleavage solution (50% dichloromethane and 50% of a mixture of 95% TFA, 2% $H_2O$, and 3% triisopropylsilane) was then added and the mixture was shaken at room temperature (RT) for 1 h. The mixture was filtered and the filtrate was concentrated to dryness. The residue was precipitated with diethyl ether and filtered.

The solid residues usually contained the desired products in high purity or were fractionated, for example, on a reverse phase (eluent: A: 100% $H_2O$/0.1 % TFA, B: 100% acetonitrile/0.1% TFA) using preparative high-pressure liquid chromatography. Lyophilization of the fractions obtained yielded the desired products.

The preparation of physiologically tolerable salts of compounds of formula I capable of salt formation, including their stereoisomeric forms, is carried out in a manner known per se. With basic reagents such as hydroxides, carbonates, hydrogencarbonates, alkoxides, and also ammonia or organic bases, for example, trimethyl- or triethylamine, ethanolamine, or triethanolamine, or alternatively basic amino acids, for example, lysine, ornithine, or arginine, the carboxylic acids form stable alkali metal, alkaline earth metal, or optionally substituted ammonium salts. If compounds of formula I contain basic groups, stable acid addition salts can also be prepared using strong acids. For this, both inorganic and organic acids such as hydrochloric, hydrobromic, sulfuric, phosphoric, methanesulfonic, benzenesulfonic, p-toluenesulfonic, 4-bromobenzenesulfonic, cyclohexylamidosulfonic, trifluoromethylsulfonic, acetic, oxalic, tartaric, succinic, or trifluoroacetic acid are suitable.

The invention also relates to pharmaceuticals comprising an efficacious amount of at least one compound of formula I or of a physiologically tolerable salt of compounds of formula I or an optionally stereoisomeric form of compounds of formula I, together with a pharmaceutically suitable and physiologically tolerable excipient, additive, and/or other active compounds and auxiliaries.

On account of the pharmacological properties, compounds according to the invention are suitable for the prophylaxis and therapy of all those disorders in whose course an increased activity of IκB kinase is involved. These include, for example, asthma, rheumatoid arthritis (in the case of inflammation), osteoarthritis, Alzheimer's disease, carcinomatous disorders (potentiation of cytotoxic therapies), cardiac infarct, cardiac insufficiency, acute coronary syndrome (unstable angina pectoris), septic shock, acute and chronic kidney failure, stroke, or atherosclerosis. In both the specification and the amended claims, the term "treating" includes prophylaxis and/or prevention.

The pharmaceuticals according to the invention are in general administered orally or parenterally. Rectal, inhalative, or transdermal administration is also possible.

The invention also relates to a process for the production of a pharmaceutical, comprising bringing at least one compound of formula I into a suitable administration form using a pharmaceutically suitable and physiologically tolerable excipient and, if appropriate, further suitable active compounds, additives, or auxiliaries.

Suitable solid or pharmaceutical preparation forms are, for example, granules, powders, coated tablets, tablets, (micro)capsules, suppositories, syrups, juices, suspensions, emulsions, drops, or injectable solutions, and preparations having protracted release of active compound, in whose preparation customary auxiliaries, such as excipients, disintegrants, binders, coating agents, swelling agents, glidants or lubricants, flavorings, sweeteners, and solubilizers are used. Frequently used auxiliaries which may be mentioned are magnesium carbonate, titanium dioxide, lactose, mannitol and other sugars, talc, lactoprotein, gelatin, starch, cellulose and its derivatives, animal and vegetable oils such as cod liver oil, sunflower, groundnut, or sesame oil, polyethylene glycol, and solvents such as, for example, sterile water and mono- or polyhydric alcohols such as glycerol.

The pharmaceutical preparations are preferably produced and administered in dose units, each unit containing as active constituent a certain dose of the compound of formula I according to the invention. In the case of solid dose units such as tablets, capsules, coated tablets, or suppositories, this dose can be up to approximately 1000 mg, preferably from approximately 50 mg to 300 mg, and in the case of injection solutions in ampoule form up to approximately 300 mg, preferably from approximately 10 mg to 100 mg.

For the treatment of an adult patient weighing approximately 70 kg, depending on the efficacy of the compound according to formula I, daily doses of approximately 20 mg to 1000 mg of active compound, preferably from approximately 100 mg to 500 mg, are indicated. Under certain circumstances, however, even higher or lower daily doses may be appropriate. The administration of the daily dose can be carried out both by single administration in the form of an individual dose unit or else of a number of smaller dose units and by multiple administration of subdivided doses at specific intervals.

As a rule, final products are determined by mass-spectroscopic methods (FAB-, ESI-MS). Unless stated otherwise, temperatures are given in degrees Celsius and RT means RT (22°–26° C.). Abbreviations used are either explained or correspond to the customary conventions.

Examples according to process variant b) as in the general working procedure

HPLC (RP 18; UV 210 nm): gradient 0–15 min. B=5–70% (A=100% $H_2O$/0.1% trifluoroacetic acid; B=100% acetonitrile/0.1% trifluoroacetic acid)

The examples in Table 1 which follows have been prepared analogously to process variant b).

TABLE 1

| Example | Structure | | Empirical formula | MS (M + H) | Note |
|---|---|---|---|---|---|
| 1 | 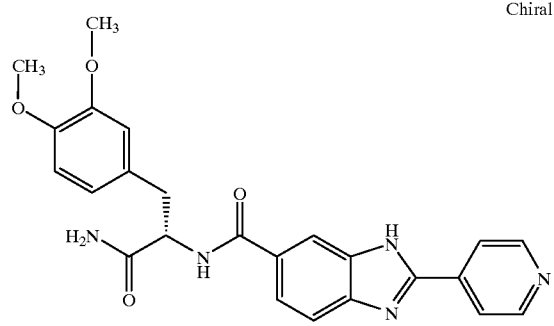 | Chiral | $C_{24}H_{23}N_5O_4$ | 446.12 | b) |
| 2 | 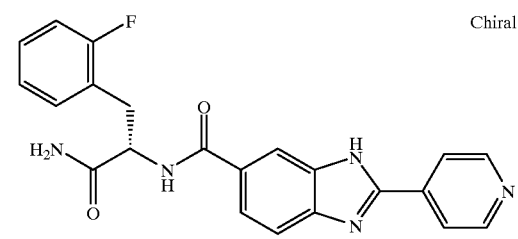 | Chiral | $C_{22}H_{18}FN_5O_2$ | 403.89 | b) |

TABLE 1-continued

| Example | Structure | | Empirical formula | MS (M + H) | Note |
|---|---|---|---|---|---|
| 3 | 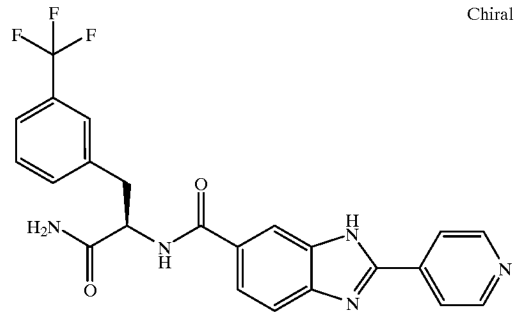 | Chiral | $C_{23}H_{18}F_3N_5O_2$ | 453.90 | b) |
| 4 | 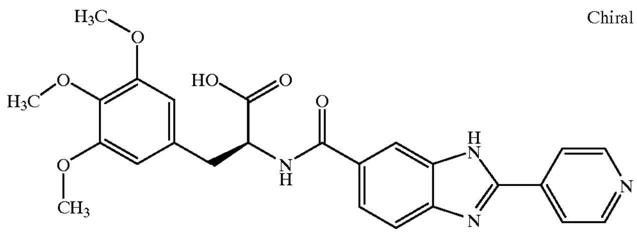 | Chiral | $C_{25}H_{24}N_4O_6$ | 476.1 | b) |
| 5 | 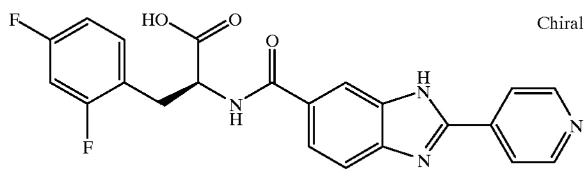 | Chiral | $C_{22}H_{16}F_2N_4O_3$ | 422.03 | b) |
| 6 | 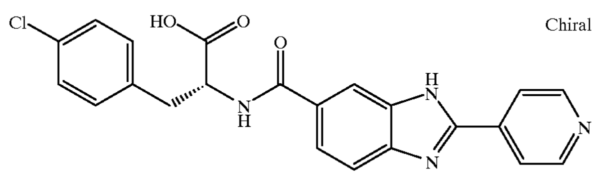 | Chiral | $C_{22}H_{17}ClN_4O_3$ | 421.88<br>419.94 | b) |
| 7 | 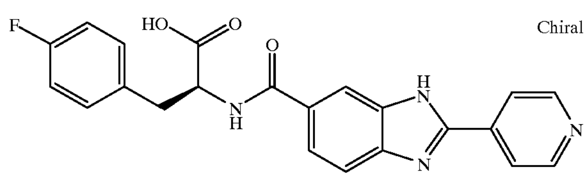 | Chiral | $C_{22}H_{17}FN_4O_3$ | 403.87 | b) |
| 8 | 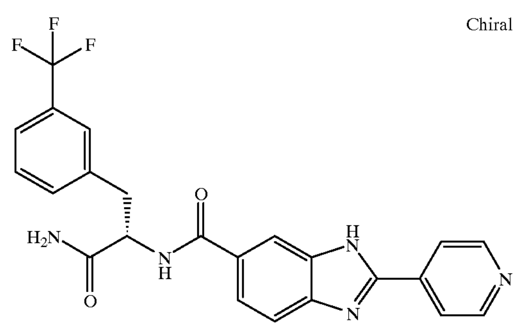 | Chiral | $C_{23}H_{18}F_3N_5O_2$ | 453.91 | b) |

TABLE 1-continued

| Example | Structure | Empirical formula | MS (M + H) | Note |
|---|---|---|---|---|
| 9 | Chiral | $C_{22}H_{18}N_6O_4$ | 430.84 | b) |
| 10 | 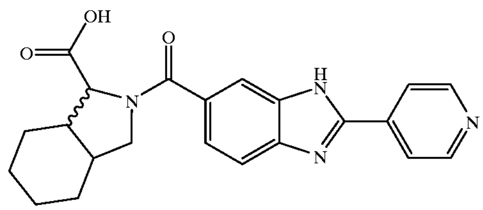 | $C_{22}H_{22}N_4O_3$ | 389.87 | b) |
| 11 | Chiral | $C_{20}H_{17}N_5O_2S$ | 391.79 | b) |
| 12 | Chiral | $C_{21}H_{18}N_6O_2$ | 387.22 | b) |
| 13 | Chiral | $C_{19}H_{19}N_5O_2$ | 349.79 | b) |
| 14 | Chiral | $C_{23}H_{19}N_5O_4$ | 430.04 | b) |

TABLE 1-continued

| Example | Structure | | Empirical formula | MS (M + H) | Note |
|---|---|---|---|---|---|
| 15 | 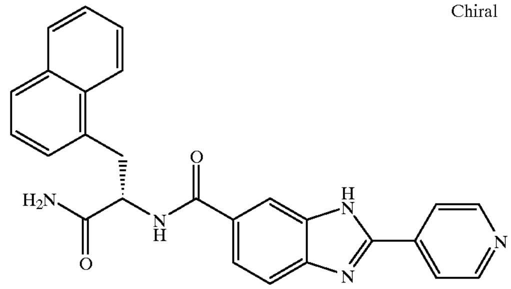 | Chiral | $C_{26}H_{21}N_5O_2$ | 435.89 | b) |
| 16 | 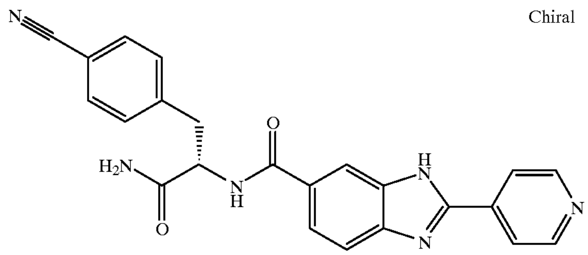 | Chiral | $C_{23}H_{18}N_6O_2$ | 410.4352 | b) |
| 17 | 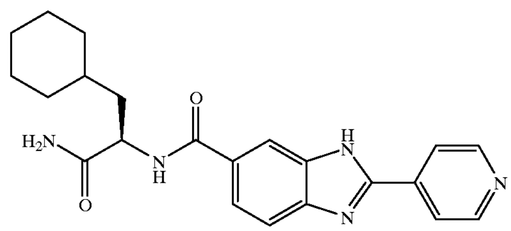 | Chiral | $C_{22}H_{25}N_5O_2$ | 392.18 | b) |
| 18 | 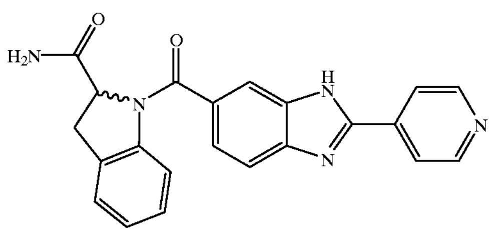 | | $C_{22}H_{17}N_5O_2$ | 383.86 | b) |
| 19 | 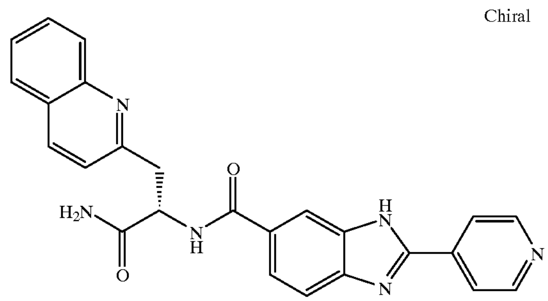 | Chiral | $C_{25}H_{20}N_6O_2$ | 437.10 | b) |

TABLE 1-continued

| Example | Structure | Empirical formula | MS (M + H) | Note |
|---|---|---|---|---|
| 20 | Chiral | $C_{22}H_{17}Br_2N_5O_3$ | 559.94 <br> 561.82 | b) |
| 21 | Chiral | $C_{24}H_{23}N_5O_4$ | 446.12 | b) |
| 22 | 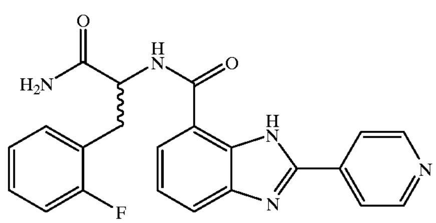 | $C_{22}H_{18}FN_5O_2$ | 403.96 | b) |
| 23 | Chiral | $C_{23}H_{18}F_3N_5O_2$ | 454.08 | b) |
| 24 | Chiral | $C_{23}H_{18}F_3N_5O_2$ | 453.99 | b) |

TABLE 1-continued

| Example | Structure | | Empirical formula | MS (M + H) | Note |
|---|---|---|---|---|---|
| 25 | 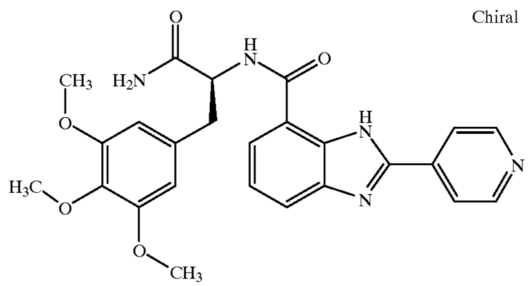 | Chiral | $C_{25}H_{25}N_5O_5$ | 476.17 | b) |
| 26 | 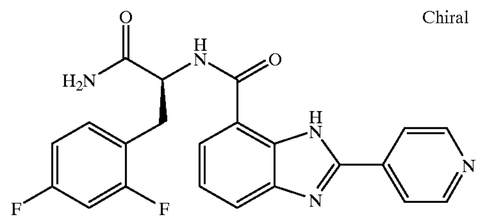 | Chiral | $C_{22}H_{17}F_2N_5O_2$ | 421.31 | b) |
| 27 | 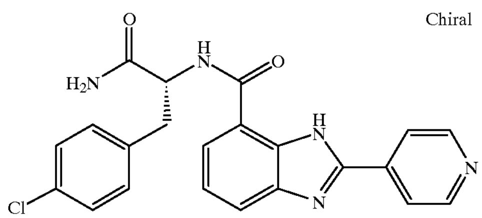 | Chiral | $C_{22}H_{18}ClN_5O_2$ | 419.94 | b) |
| 28 | 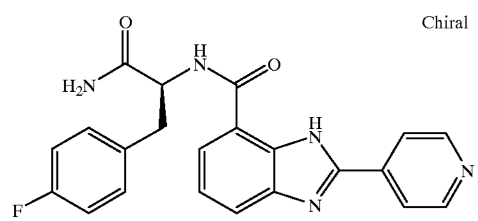 | Chiral | $C_{22}H_{18}FN_5O_2$ | 403.80 | b) |
| 29 | 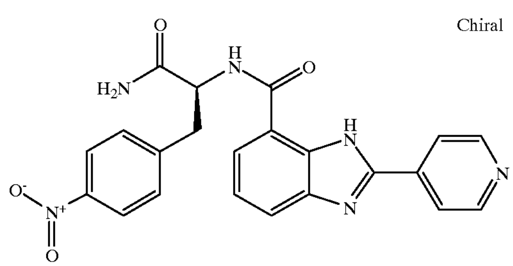 | Chiral | $C_{22}H_{18}N_6O_4$ | 431.07 | b) |
| 30 | 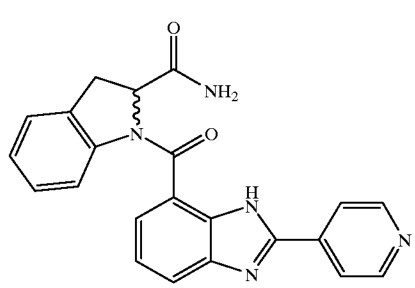 | | $C_{22}H_{17}N_5O_2$ | 383.74 | b) |

TABLE 1-continued

| Example | Structure | Empirical formula | MS (M + H) | Note |
|---|---|---|---|---|
| 31 | Chiral | $C_{23}H_{18}F_3N_5O_2$ | 453.97 | b) |
| 32 | Chiral | $C_{22}H_{18}N_6O_4$ | 430.83 | b) |
| 33 | 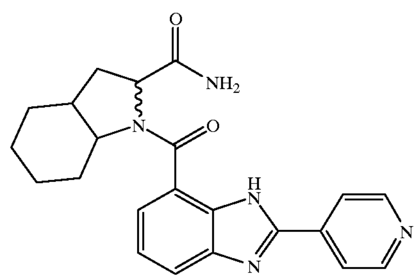 | $C_{22}H_{23}N_5O_2$ | 389.95 | b) |
| 34 | Chiral | $C_{20}H_{17}N_5O_2S$ | 392.20 | b) |
| 35 | Chiral | $C_{21}H_{18}N_6O_2$ | 387.04 | b) |
| 36 | Chiral | $C_{19}H_{19}N_5O_2$ | 349.98 | b) |

TABLE 1-continued

| Example | Structure | Empirical formula | MS (M + H) | Note |
|---|---|---|---|---|
| 37 | Chiral | $C_{23}H_{19}N_5O_4$ | 429.74 | b) |
| 38 | Chiral | $C_{26}H_{21}N_5O_2$ | 435.90 | b) |
| 39 | Chiral | $C_{23}H_{18}N_6O_2$ | 410.44 | b) |
| 40 | Chiral | $C_{22}H_{17}Br_2N_5O_3$ | 559.99 561.85 | b) |
| 41 | Chiral | $C_{22}H_{25}N_5O_2$ | 391.83 | b) |
| 42 | Chiral | $C_{22}H_{18}FN_5O_2$ | 404.17 | b) |

TABLE 1-continued
| Example | Structure | Empirical formula | MS (M + H) | Note |
|---|---|---|---|---|
| 43 | 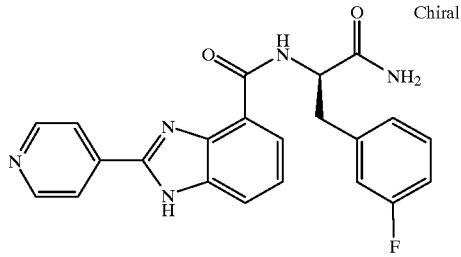 Chiral | C$_{22}$H$_{18}$FN$_5$O$_2$ | 404.08 | b) |
| 44 | 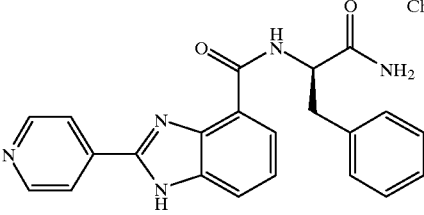 Chiral | C$_{22}$H$_{18}$FN$_5$O$_2$ | 403.88 | b) |
| 45 | 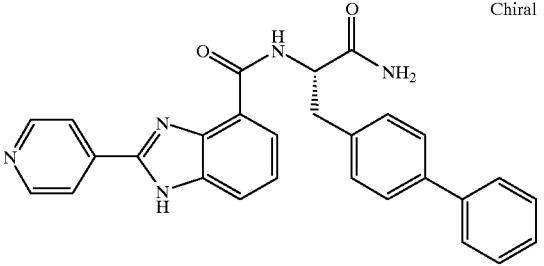 Chiral | C$_{28}$H$_{23}$N$_5$O$_2$ | 462.18 | b) |
| 46 | 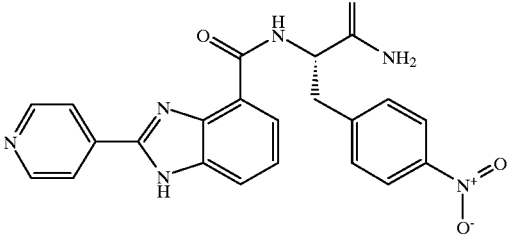 Chiral | C$_{22}$H$_{18}$N$_6$O$_4$ | 431.03 | b) |
| 47 | 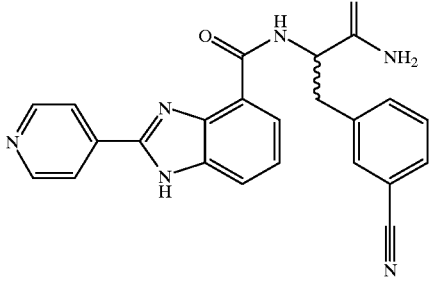 | C$_{23}$H$_{18}$N$_6$O$_2$ | 411.1 | b) |

TABLE 1-continued
| Example | Structure | Empirical formula | MS (M + H) | Note |
|---|---|---|---|---|
| 48 | 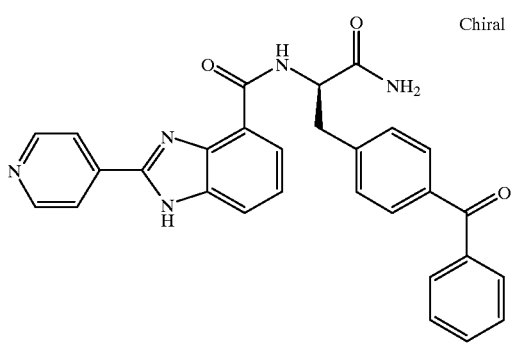 | $C_{29}H_{23}N_5O_3$ | 489.93 | b) |
| 49 | 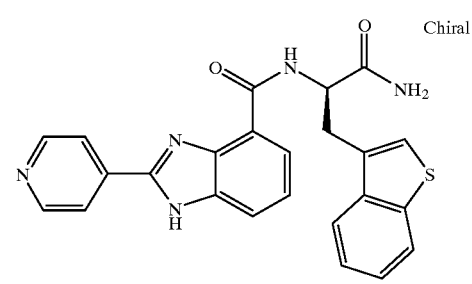 | $C_{24}H_{19}N_5O_2S$ | 442.1 | b) |
| 50 | 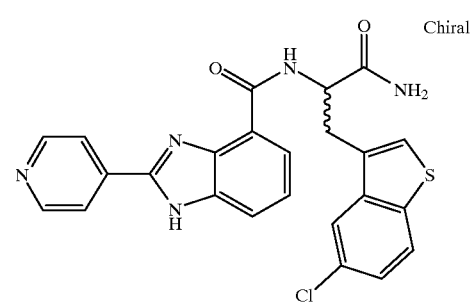 | $C_{24}H_{18}ClN_5O_2S$ | 475.98 | b) |
| 51 | 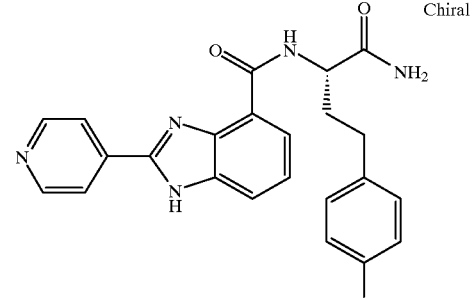 | $C_{23}H_{21}N_5O_3$ | 416.27 | b) |

TABLE 1-continued

| Example | Structure | Empirical formula | MS (M + H) | Note |
|---|---|---|---|---|
| 52 | 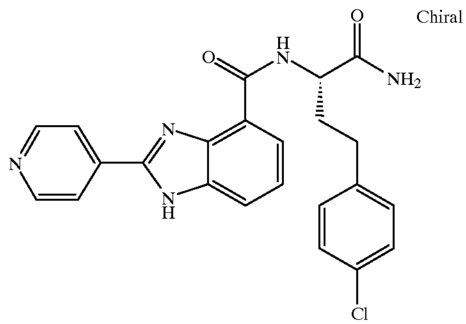 | $C_{22}H_{18}ClN_5O_2$ | 421.88 419.84 | b) |
| 53 | 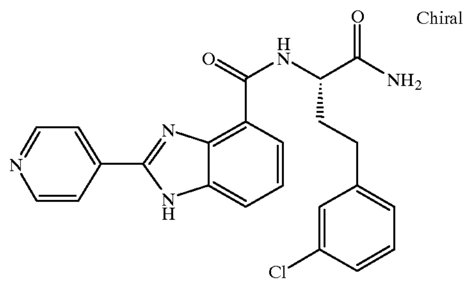 | $C_{22}H_{18}ClN_5O_2$ | 421.91 | b) |
| 54 | 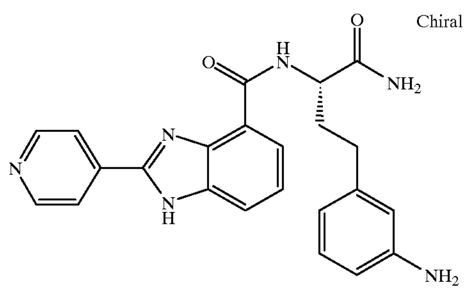 | $C_{22}H_{20}N_6O_2$ | 400.94 | b) |
| 55 | 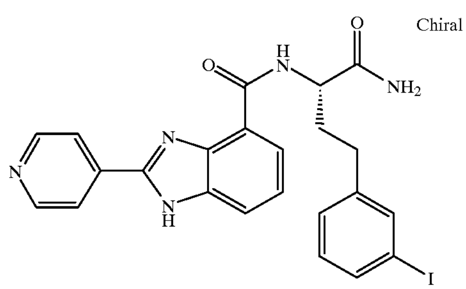 | $C_{22}H_{18}IN_5O_2$ | 510.72 | b) |
| 56 | 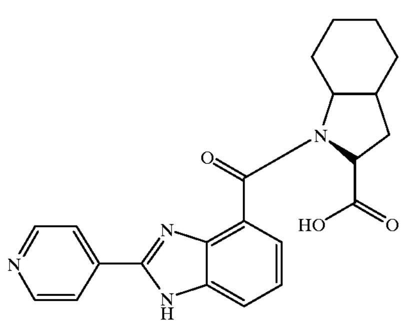 | $C_{22}H_{22}N_4O_3$ | 389.85 | b) |

TABLE 1-continued

| Example | Structure | Empirical formula | MS (M + H) | Note |
|---|---|---|---|---|
| 57 | 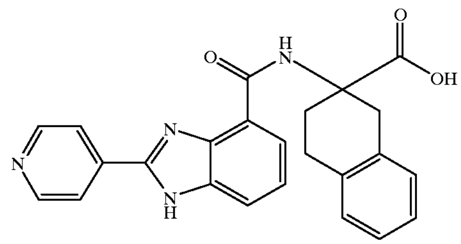 | $C_{24}H_{20}N_4O_3$ | 411.88 413.14 | b) |
| 58 | 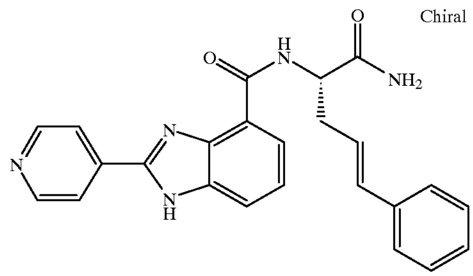 | $C_{24}H_{21}N_5O_2$ | 412.01 | b) |
| 59 | 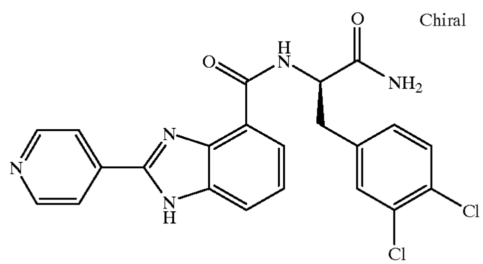 | $C_{22}H_{17}Cl_2N_5O_2$ | 456.02 454.13 | b) |
| 60 | 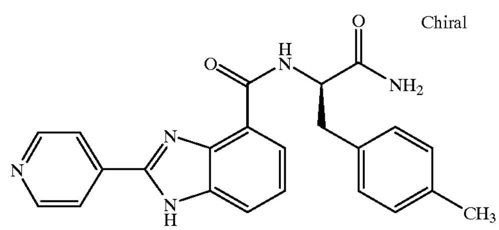 | $C_{23}H_{21}N_5O_2$ | 400.14 | b) |
| 61 | 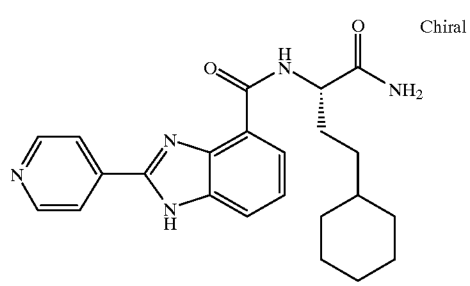 | $C_{23}H_{27}N_5O_2$ | 406.21 | b) |

TABLE 1-continued
| Example | Structure | Empirical formula | MS (M + H) | Note |
|---|---|---|---|---|
| 62 | 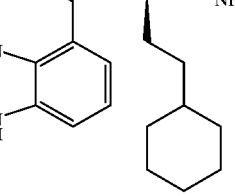 | $C_{23}H_{27}N_5O_2$ | 406.12 | b) |
| 63 | 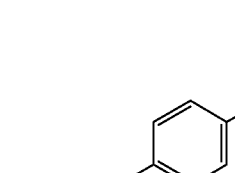 | $C_{28}H_{23}N_5O_2$ | 462.21 | b) |
| 64 | 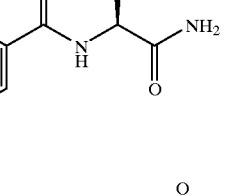 | $C_{22}H_{19}N_5O_2$ | 385.67 | b) |
| 65 | 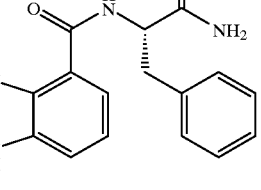 | $C_{22}H_{18}FN_5O_2$ | 403.92 | b) |
| 66 | 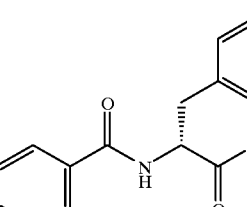 | $C_{22}H_{18}FN_5O_2$ | 404.02 | b) |

TABLE 1-continued

| Example | Structure | Empirical formula | MS (M + H) | Note |
|---|---|---|---|---|
| 67 | Chiral | $C_{22}H_{18}FN_5O_2$ | 404 | b) |
| 68 | Chiral | $C_{22}H_{18}N_6O_4$ | 430.96 | b) |
| 69 | 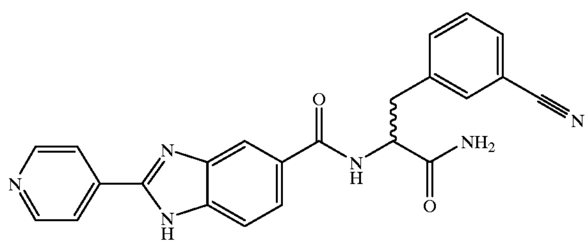 | $C_{23}H_{18}N_6O_2$ | 411.04 | b) |
| 70 | Chiral | $C_{24}H_{19}N_5O_2S$ | 441.81 | b) |
| 71 | 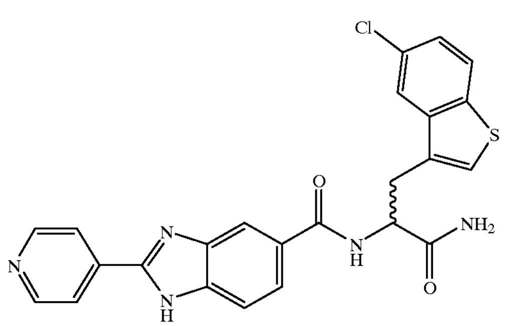 | $C_{24}H_{18}ClN_5O_2S$ | 477.96<br>475.97 | b) |

TABLE 1-continued
| Example | Structure | Empirical formula | MS (M + H) | Note |
|---|---|---|---|---|
| 72 | 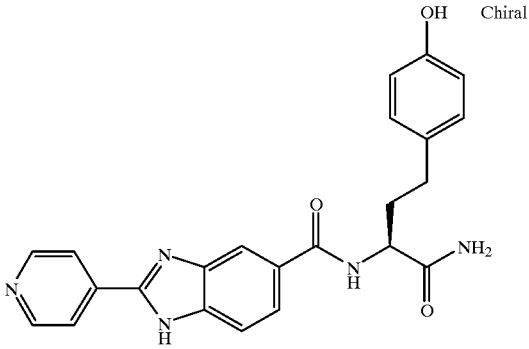 | $C_{23}H_{21}N_5O_3$ | 416.13 | b) |
| 73 | 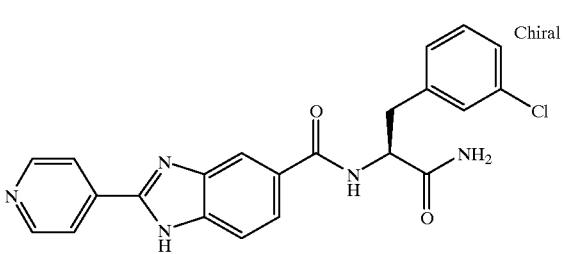 | $C_{22}H_{18}ClN_5O_2$ | 419.98<br>421.90 | b) |
| 74 | 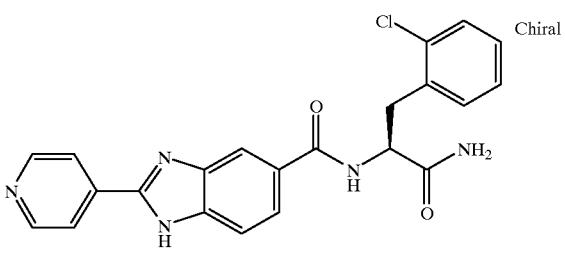 | $C_{22}H_{18}ClN_5O_2$ | 420.12 | b) |
| 75 | 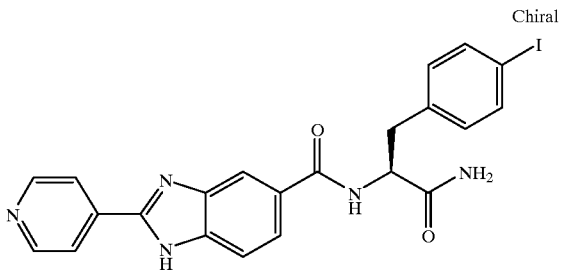 | $C_{22}H_{18}IN_5O_2$ | 512.06 | b) |
| 76 | 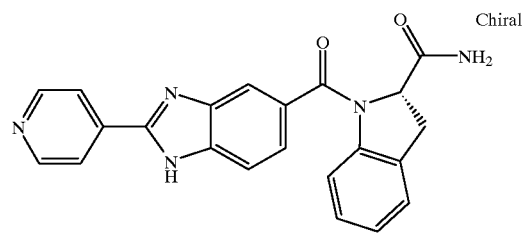 | $C_{22}H_{17}N_5O_2$ | 384.1 | b) |

TABLE 1-continued
| Example | Structure | Empirical formula | MS (M + H) | Note |
|---|---|---|---|---|
| 77 | 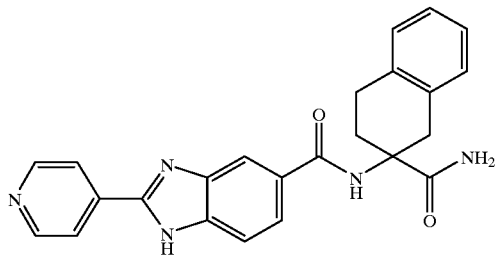 | C₂₄H₂₁N₅O₂ | 412.1 | b) |
| 78 | 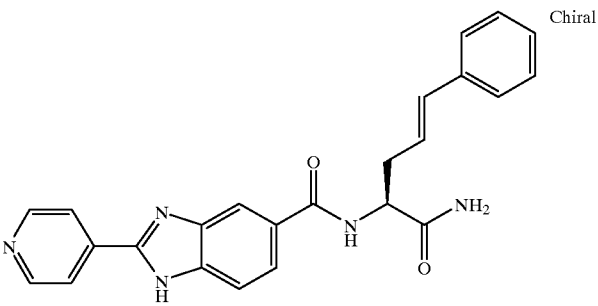 Chiral | C₂₄H₂₁N₅O₂ | 412.07 | b) |
| 79 | 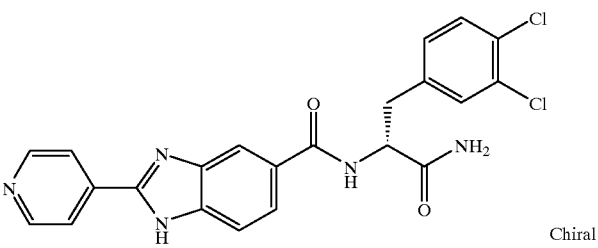 Chiral | C₂₂H₁₇Cl₂N₅O₂ | 456.05<br>453.89 | b) |
| 80 | 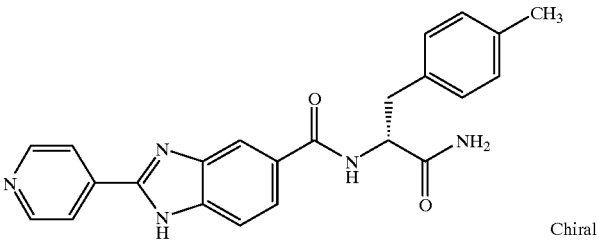 Chiral | C₂₃H₂₁N₅O₂ | 399.95 | b) |
| 81 | 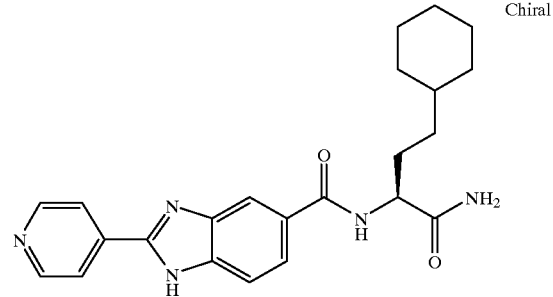 Chiral | C₂₃H₂₇N₅O₂ | 406.04 | b) |

TABLE 1-continued
| Example | Structure | Empirical formula | MS (M + H) | Note |
|---|---|---|---|---|
| 82 | 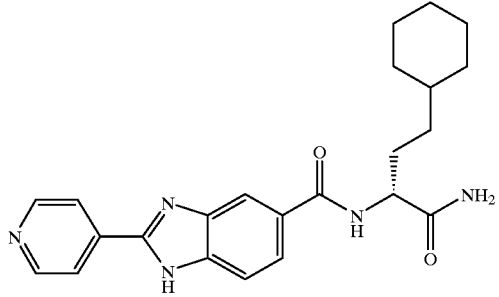 Chiral | C₂₃H₂₇N₅O₂ | 405.87 | b) |
| 83 | 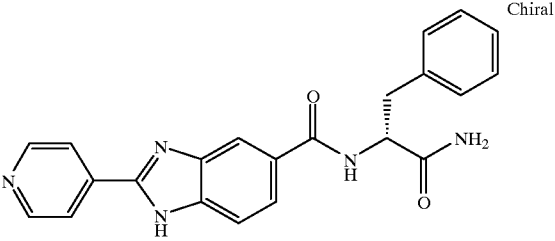 Chiral | C₂₂H₁₉N₅O₂ | 385.78 | b) |
| 84 | 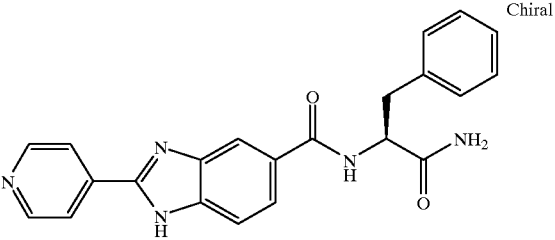 Chiral | C₂₂H₁₉N₅O₂ | 385.78 | b) |
| 85 | 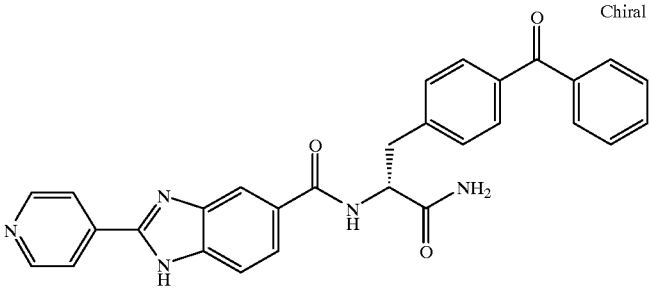 Chiral | C₂₉H₂₃N₅O₃ | 490.1 | b) |
| 86 | 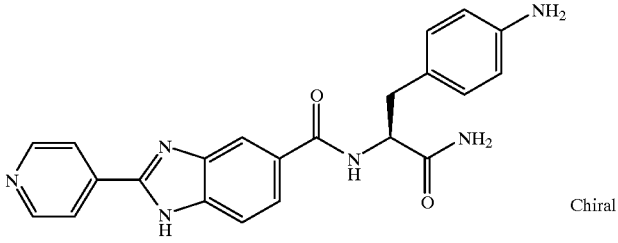 Chiral | C₂₂H₂₀N₆O₂ | 400.44 | b) |

TABLE 1-continued

| Example | Structure | | Empirical formula | MS (M + H) | Note |
|---|---|---|---|---|---|
| 87 | 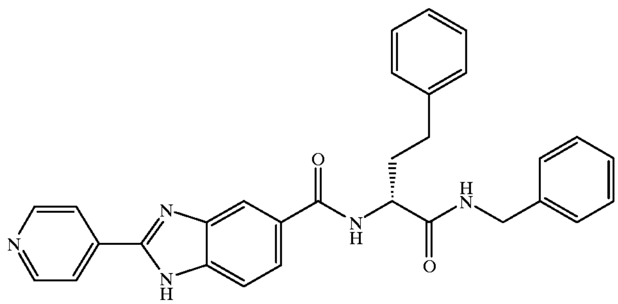 | Chiral | C30H27N5O2 | 490.3 | b) |
| 88 | 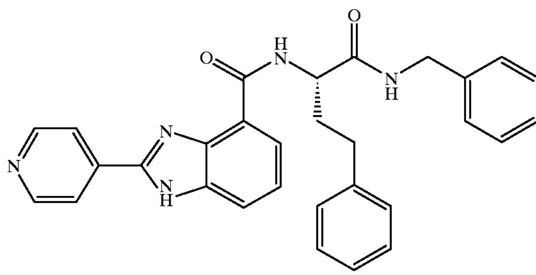 | Chiral | C30H27N5O2 | 490.27 | b) |
| 89 | 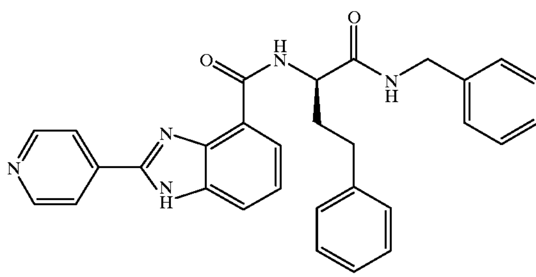 | Chiral | C30H27N5O2 | 490.22 | b) |

EXAMPLE 90

(2-(Pyridyl-4-yl)-1H-benzimidazole-4-carbonyl)-(L)-leucine methyl ester (1)

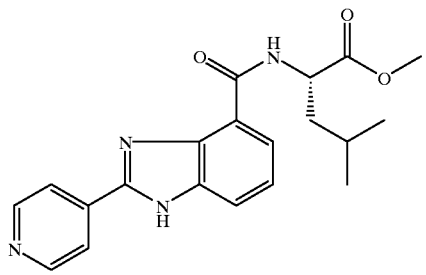

Ammonium 3-nitrophthalamidate (1a)

100 g (518 mmol) of 3-nitrophthalic anhydride were introduced at RT and treated rapidly with 170 ml of concentrated ammonium hydroxide solution with stirring. The mixture was stirred at RT for 1 h. The precipitate was filtered off and dried in a desiccator. Yield: 95.6 g (88%).

2-Amino-3-nitrobenzoic acid (1b)

22 g (105.2 mmol) of ammonium 3-nitrophthalamidate (1a) were treated with stirring with 165 ml of sodium hypochlorite solution. After 5 minutes, a solution of 8.8 g of sodium hydroxide in 22 ml of water was added and the mixture was then stirred at 70° C. for 1 h. The suspension was poured into 500 ml of water with stirring. The resulting clear solution was acidified with concentrated HCl. The precipitate was filtered off and dried in a desiccator. Yield: 9.68 g (51%).

2,3-Diaminobenzoic acid (1c)

14 g (76.9 mmol) of 2-amino-3-nitrobenzoic acid (1b) were dissolved in 500 ml of methanol, treated with Pd/C, and hydrogenated with hydrogen. After 4 h, the catalyst was filtered off with suction and concentrated. A dark-brown solid was obtained. Yield: 11.67 g (99%).

2-(Pyrid-4-yl)-1H-benzimidazole-4-carboxylic acid (1d)

700 mg (4.6 mmol) of 2,3-diaminobenzoic acid (1c) and 0.47 ml (4.95 mmol) of 4-pyridylaldehyde were dissolved in 40 ml of nitrobenzene and heated at 145° C. for 2 h with stirring. The mixture was then cooled and the precipitate was filtered off with suction. The precipitate was washed with ethyl acetate and dried in a desiccator. Yield: 800 mg (73%).

(2-(Pyrid-4-yl)-1H-benzimidazole-4-carbonyl)-(L)-leucine methyl ester (1)

120 mg (0.5 mmol) of 2-(pyrid-4-yl)-1H-benzimidazole-4-carboxylic acid (1d) and 84 mg (0.5 mmol) of H-(L)-leucine methyl ester were dissolved in 5 ml of DMF. 164 mg (0.5 mmol) of TOTU and 0.086 ml of diisopropylethylamine were added and the mixture was stirred at RT for 3 h. The precipitate was filtered off and the filtrate was concentrated. The residue was dissolved in ethyl acetate, the solution was washed with water, and the organic phase was dried using anhydrous sodium sulfate and concentrated. Yield: 180 mg (98%).

$(M+H)^+=367.1$ $(CI^+)$.

EXAMPLE 91

(2-(Pyrid-4-yl)-1H-benzimidazole-4-carbonyl)-(L)-valinamide (2)

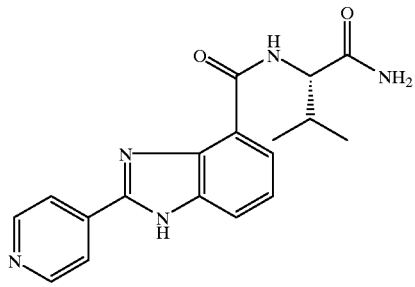

120 mg (0.5 mmol) of 2-(pyrid-4-yl)-1H-benzimidazole-4-carboxylic acid (1d) and 76.4 mg (0.5 mmol) of H-(L)-valinamide were dissolved in 5 ml of DMF. 164 mg (0.5 mmol) of TOTU and 0.086 ml of diisopropylethylamine were added and the mixture was stirred at RT for 3 h. The precipitate was filtered off and the filtrate was concentrated. The residue was dissolved in ethyl acetate, the solution was washed with saturated sodium chloride solution, and the organic phase was dried using anhydride sodium sulfate and concentrated. Yield: 168 mg (99%). $(M+H)^+=338.2$ $(CI^+)$.

EXAMPLE 92

(2-(Pyrid-4-yl)-1H-benzimidazole-4-carbonyl)-(S)-histidine methyl ester (3)

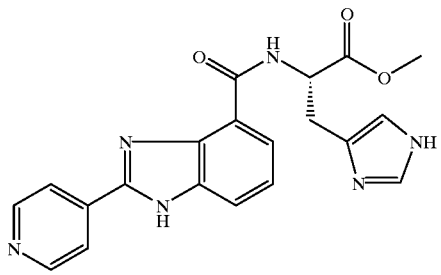

(2-(Pyrid-4-yl)-1H-benzimidazole-4-carbonyl)-(L)-histidine(Trt) methyl ester (3a)

120 mg (0.5 mmol) of 2-(pyrid4-yl)-1H-benzimidazole-4-carboxylic acid (1d) and 242 mg (0.5 mmol) of H-(L)-histidine(Trt) methyl ester were dissolved in 5 ml of DMF. 164 mg (0.5 mmol) of TOTU and 0.172 ml of diisopropylethylamine were added and the mixture was stirred at RT for 3 h. The clear solution was concentrated. The residue was dissolved in ethyl acetate, the solution was washed with water, and the organic phase was dried using anhydrous sodium sulfate and concentrated. Yield: 380 mg of crude product. $(M+H)^+=633.3$ $(ES^+)$.

EXAMPLE 93

2-(Pyrid-4-yl)-1H-benzimidazole-4-carbonyl-(L)-methioninamide (4)

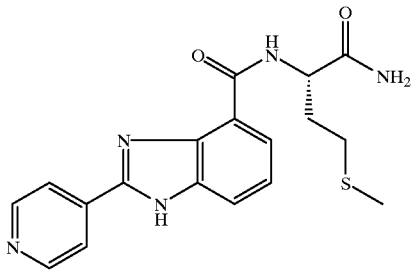

120 mg (0.5 mmol) of 2-(pyrid4-yl)-1H-benzimidazole-4-carboxylic acid (1d) and 74.2 mg (0.5 mmol) of H-(L)-methioninamide were dissolved in 5 ml of DMF. 164 mg (0.5 mmol) of TOTU and 0.086 ml of diisopropylethylamine were added and the mixture was stirred at RT for 3 hours. The clear solution was concentrated. The residue was dissolved in ethyl acetate, the solution was washed with saturated sodium chloride solution, and the organic phase was dried using anhydrous sodium sulfate and concentrated. Yield: 149 mg (81%).

$(M+H)^+=370.2$ $(ES^+)$.

The examples mentioned in Table 2 which follows have been prepared analogously to Examples 90 to 93.

TABLE 2

| Example | Structure | Empirical formula | MS (M + H) | Note |
|---|---|---|---|---|
| 94 | 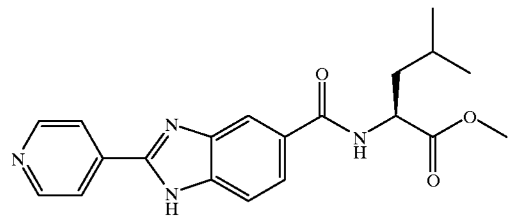 | M.W. = 366.42<br>C₂₀H₂₂N₄O₃ | 367.1 | Process variant a) |
| 95 | 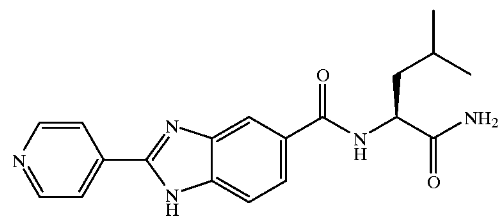 | M.W. = 351.41<br>C₁₉H₂₁N₅O₂ | 352.2 | a) |
| 96 | 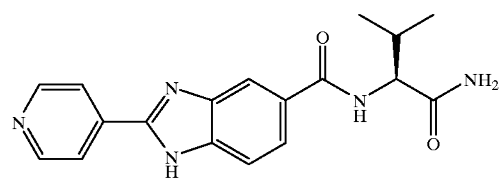 | M.W. = 337.38<br>C₁₈H₁₉N₅O₂ | 338.2 | a) |
| 97 | 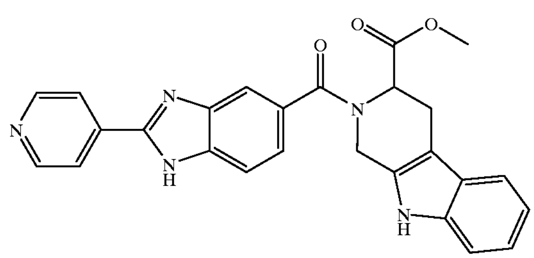 | M.W. = 451.49<br>C₂₆H₂₁N₅O₃ | 452.2 | a) |
| 98 | 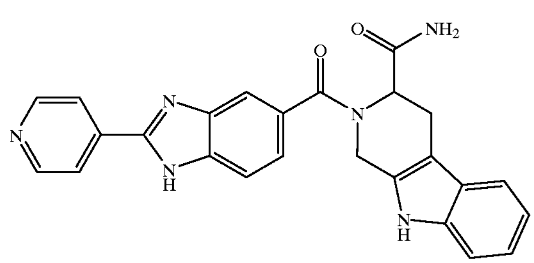 | M.W. = 436.48<br>C₂₅H₂₀N₆O₂ | 437.2 | a) |
| 99 | 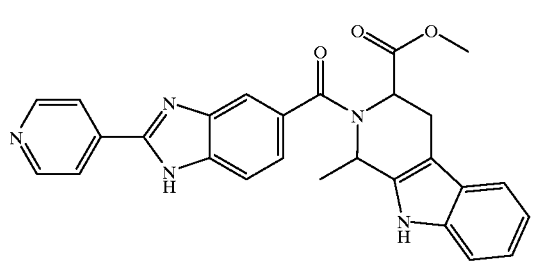 | M.W. = 465.52<br>C₂₇H₂₃N₅O₃ | 466.2 | a) |

TABLE 2-continued
| Example | Structure | Empirical formula | MS (M + H) | Note |
|---|---|---|---|---|
| 100 | 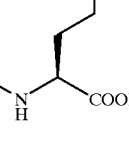 | M.W.=400.44<br>$C_{23}H_{20}N_4O_3$ | 401.2 | a) |
| 101 | 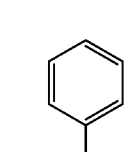 | M.W. = 399.46<br>$C_{23}H_{21}N_5O_2$ | 400.2 | a) |
| 102 | 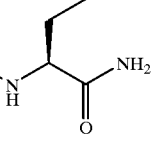 | M.W.= 501.55<br>$C_{27}H_{27}N_5O_5$ | 502.3 | a) |
| 103 | 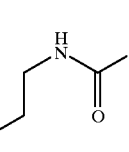 | M.W. = 444.49<br>$C_{25}H_{24}N_4O_4$ | 445.3 | a) |
| 104 | 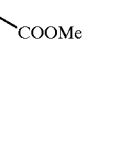 | M.W. = 454.49<br>$C_{25}H_{22}N_6O_3$ | 455.1 | a) |

TABLE 2-continued
| Example | Structure | Empirical formula | MS (M + H) | Note |
|---|---|---|---|---|
| 105 | 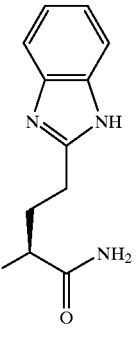 | M.W. = 439.48<br>$C_{24}H_{21}N_7O_2$ | 440.2 | a) |
| 106 | 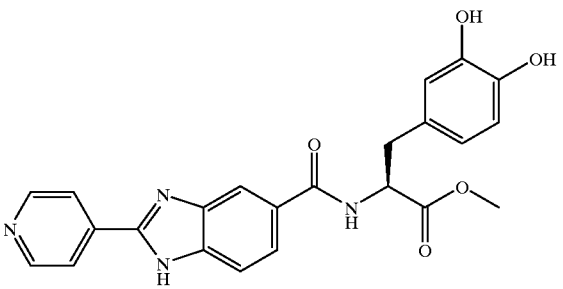 | M.W. = 432.44<br>$C_{23}H_{20}N_4O_5$ | 433.2 | a) |
| 107 | 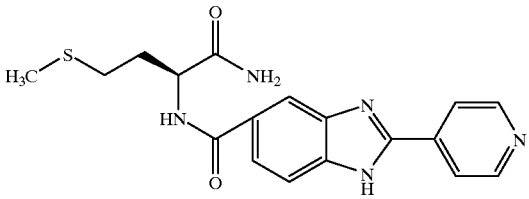 | M.W. = 369.45<br>$C_{18}H_{19}N_5O_2S$ | 370.1 | a) |
| 108 | 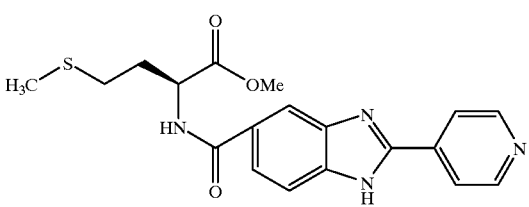 | M.W. = 384.46<br>$C_{19}H_{20}N_4O_3S$ | 385.1 | a) |
| 109 | 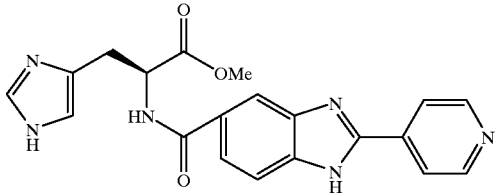 | M.W. = 390.40<br>$C_{20}H_{18}N_6O_3$ | 391.1 | a) |

TABLE 2-continued

| Example | Structure | Empirical formula | MS (M + H) | Note |
|---|---|---|---|---|
| 110 | 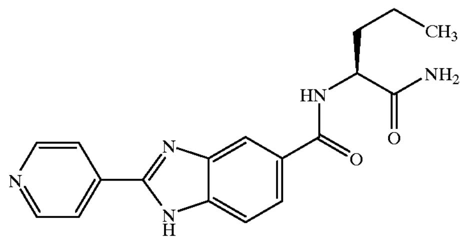 | M.W. = 337.38 $C_{18}H_{19}N_5O_2$ | 338.2 | a) |
| 111 | 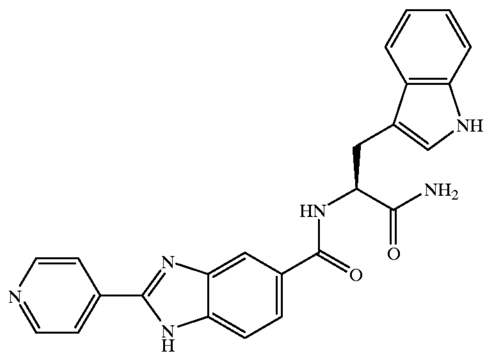 | M.W. = 424.47 $C_{24}H_{20}N_6O_2$ | 425.2 | a) |
| 112 | 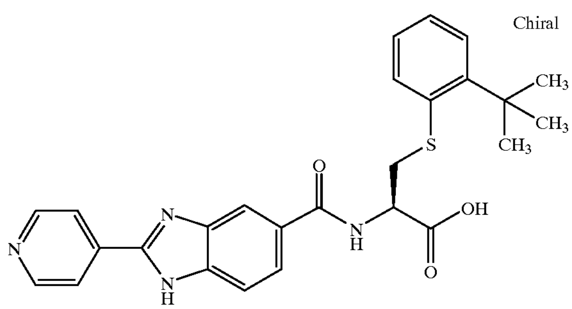 | M.W. = 474.59 $C_{26}H_{26}N_4O_3S$ | 476 | a) |
| 113 | 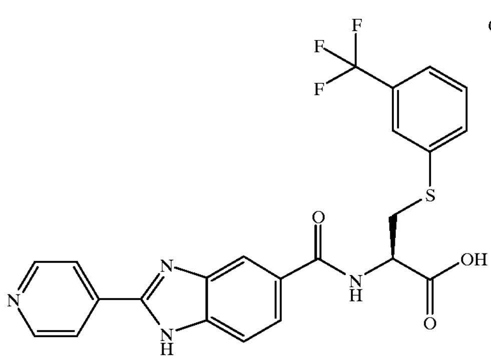 | M.W. = 486.48 $C_{23}H_{17}F_3N_4O_3S$ | 487 | a) |

TABLE 2-continued

| Example | Structure | Empirical formula | MS (M + H) | Note |
|---------|-----------|-------------------|------------|------|
| 114 | 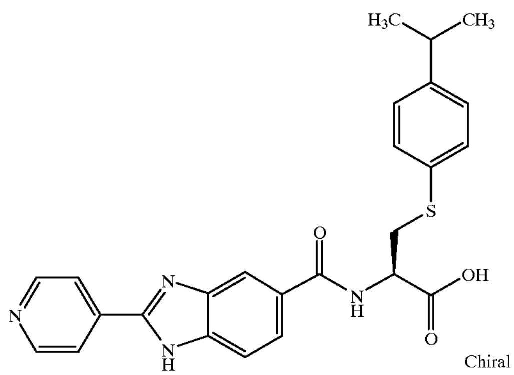 | M.W. = 460.56<br>$C_{25}H_{24}N_4O_3S$ | 462 | a) |
| 115 | 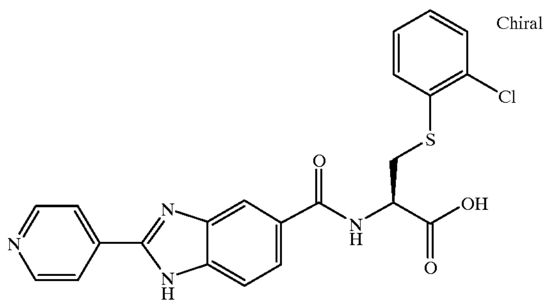 | M.W. = 452.92<br>$C_{22}H_{17}ClN_4O_3S$ | 454 | a) |
| 116 | 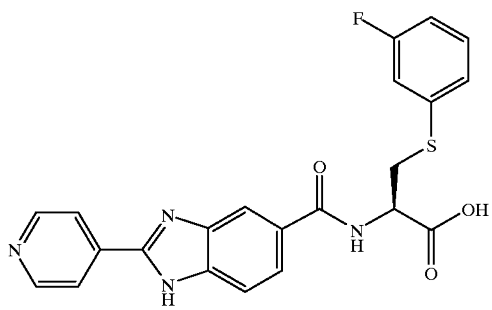 | M.W. = 436.47<br>$C_{22}H_{17}FN_4O_3S$ | 437 | a) |
| 117 | 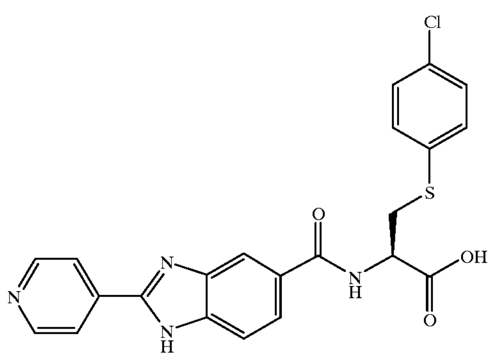 | M.W. = 452.92<br>$C_{22}H_{17}ClN_4O_3S$ | 454 | a) |

TABLE 2-continued

| Example | Structure | Empirical formula | MS (M + H) | Note |
| --- | --- | --- | --- | --- |
| 118 | Chiral | M.W. = 448.50<br>C₂₃H₂₀N₄O₄S | 449 | a) |
| 119 | Chiral | M.W. = 448.50<br>C₂₃H₂₀N₄O₄S | 449 | a) |
| 120 | Chiral | M.W. = 446.53<br>C₂₄H₂₂N₄O₃S | 447 | a) |
| 121 | Chiral | M.W. = 476.51<br>C₂₄H₂₀N₄O₅S | 477 | a) |

TABLE 2-continued
| Example | Structure | Empirical formula | MS (M + H) | Note |
| --- | --- | --- | --- | --- |
| 122 | 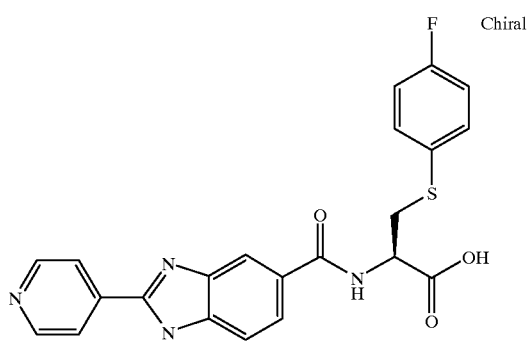 Chiral | M.W. = 436.47<br>$C_{22}H_{17}FN_4O_3S$ | 437 | a) |
| 123 | 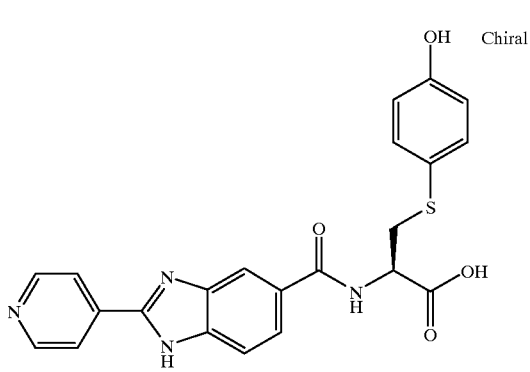 Chiral | M.W. = 434.48<br>$C_{22}H_{18}N_4O_4S$ | 435 | a) |
| 124 | 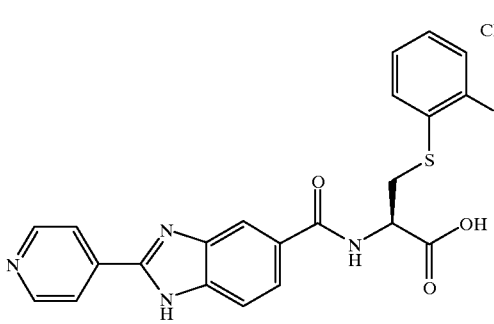 Chiral | M.W. = 433.49<br>$C_{22}H_{19}N_5O_3S$ | 434 | a) |
| 125 | 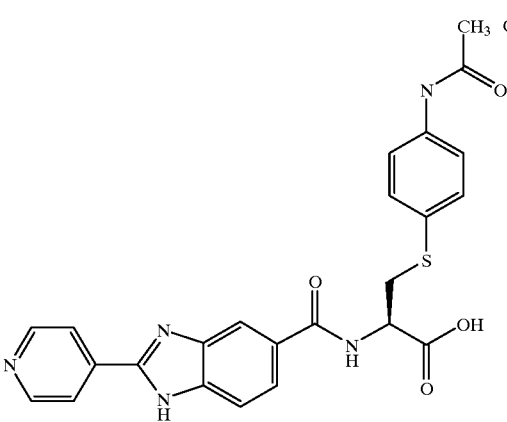 Chiral | M.W. = 475.53<br>$C_{24}H_{21}N_5O_4S$ | 476 | a) |

TABLE 2-continued
| Example | Structure | Empirical formula | MS (M + H) | Note |
|---|---|---|---|---|
| 126 | 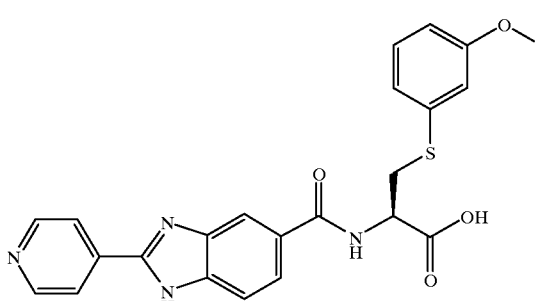 Chiral | M.W. = 448.50 $C_{23}H_{20}N_4O_4S$ | 449 | a) |
| 127 | 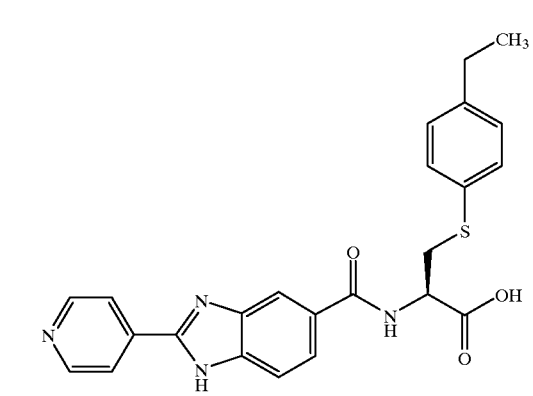 Chiral | M.W. = 446.53 $C_{24}H_{22}N_4O_3S$ | 447 | a) |
| 128 | 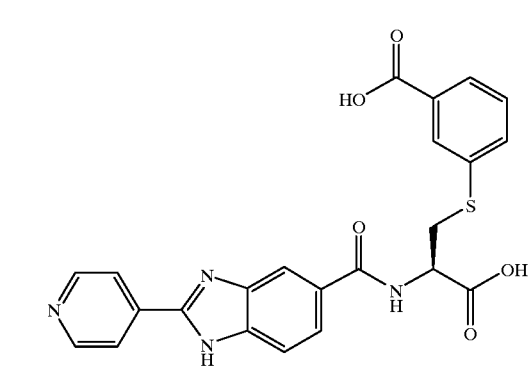 Chiral | M.W. = 462.49 $C_{23}H_{18}N_4O_5S$ | 463 | a) |
| 129 | 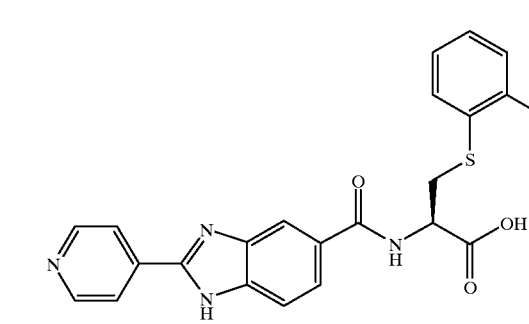 Chiral | M.W. = 446.53 $C_{24}H_{22}N_4O_3S$ | 447 | a) |

TABLE 2-continued

| Example | Structure | Empirical formula | MS (M + H) | Note |
|---|---|---|---|---|
| 130 | Chiral | M.W. = 487.37<br>$C_{22}H_{16}Cl_2N_4O_3S$ | 488 | a) |
| 131 | Chiral | M.W. = 435.48<br>$C_{22}H_{18}FN_5O_2S$ | 436 | a) |
| 132 | Chiral | M.W. = 431.52<br>$C_{23}H_{21}N_5O_2S$ | 432 | a) |
| 133 | Chiral | M.W. = 467.55<br>$C_{26}H_{21}N_5O_2S$ | 468 | a) |

TABLE 2-continued
| Example | Structure | | Empirical formula | MS (M + H) | Note |
|---|---|---|---|---|---|
| 134 | 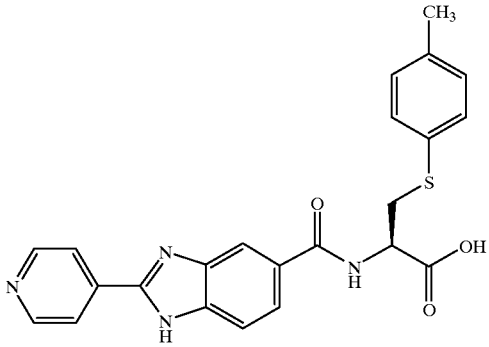 | Chiral | M.W. = 432.50 $C_{23}H_{20}N_4O_3S$ | 433 | a) |
| 135 | 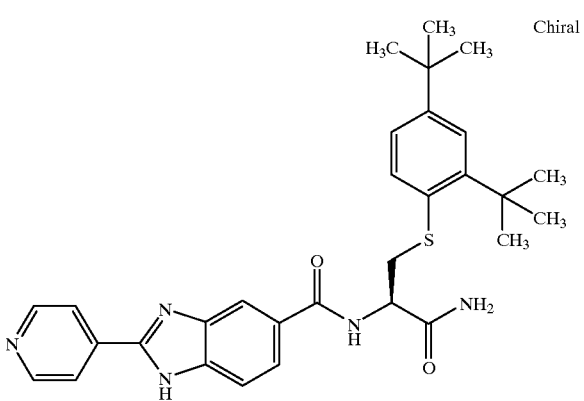 | Chiral | M.W. = 529.71 $C_{30}H_{35}N_5O_2S$ | 531 | a) |
| 136 | 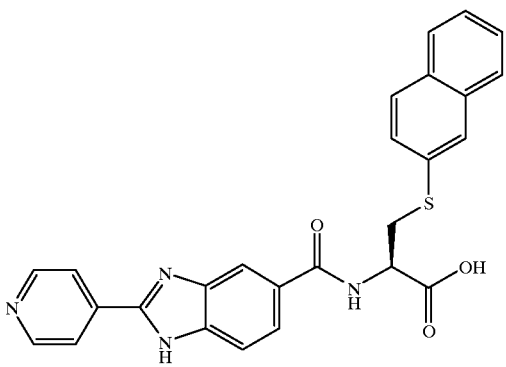 | Chiral | M.W. = 468.54 $C_{26}H_{20}N_4O_3S$ | 469 | a) |
| 137 | 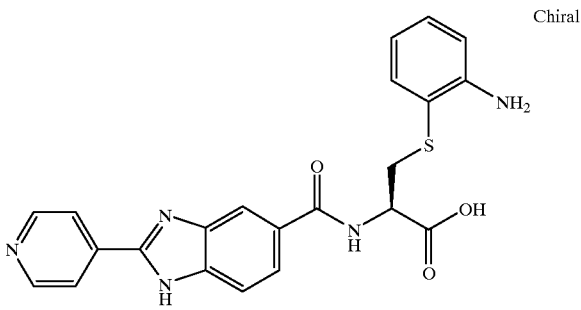 | Chiral | M.W. = 433.49 $C_{22}H_{19}N_5O_3S$ | 434 | a) |

TABLE 2-continued
| Example | Structure | Empirical formula | MS (M + H) | Note |
|---|---|---|---|---|
| 138 | 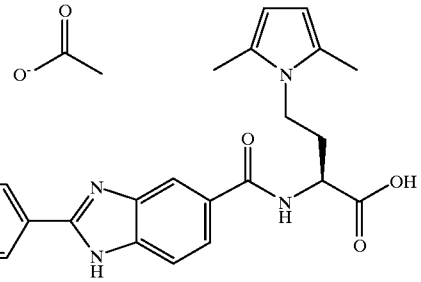 | M.W. = 417.47<br>$C_{23}H_{23}N_5O_3$ | 418.3 | a) |
| 139 | 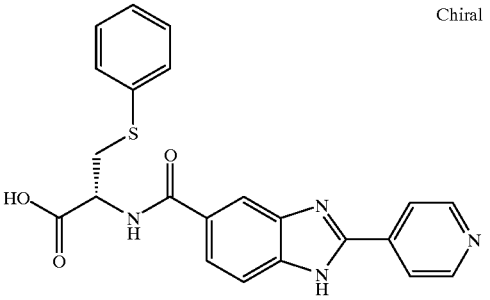 Chiral | M.W. = 418.48<br>$C_{22}H_{18}N_4O_3S$ | 419.2 | a) |
| 140 | 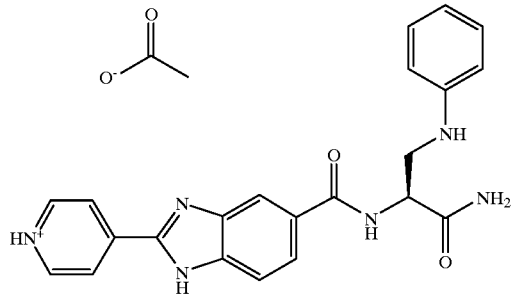 | M.W. = 400.44<br>$C_{22}H_{20}N_6O_2$ | 401.2 | a) |
| 141 | 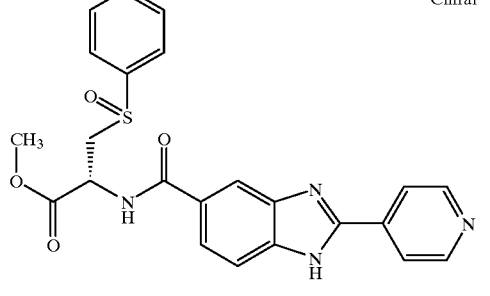 Chiral | M.W. = 448.50<br>$C_{23}H_{20}N_4O_4S$ | 449.3 | a) |
| 142 | 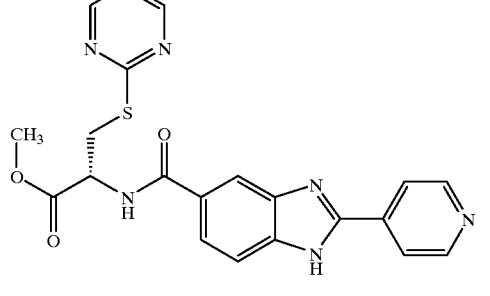 Chiral | M.W. = 434.48<br>$C_{21}H_{18}N_6O_3S$ | 435.5 | a) |

TABLE 2-continued

| Example | Structure | Empirical formula | MS (M + H) | Note |
|---|---|---|---|---|
| 143 | Chiral | M.W. = 386.46 $C_{23}H_{22}N_4O_2$ | 387.2 | a) |
| 144 | 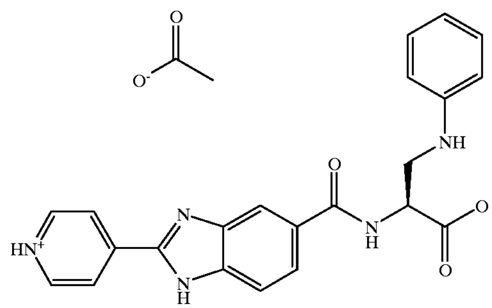 | M.W. = 401.43 $C_{22}H_{19}N_5O_3$ | 402.2 | a) |
| 145 | Chiral | M.W. = 403.40 $C_{20}H_{17}N_7O_3$ | 404.2 | a) |
| 146 | Chiral | M.W. = 389.42 $C_{21}H_{19}N_5O_3$ | 390.2 | a) |
| 147 | Chiral | M.W. = 349.35 $C_{18}H_{15}N_5O_3$ | 350.3 | a) |

TABLE 2-continued

| Example | Structure | Empirical formula | MS (M + H) | Note |
|---|---|---|---|---|
| 148 | 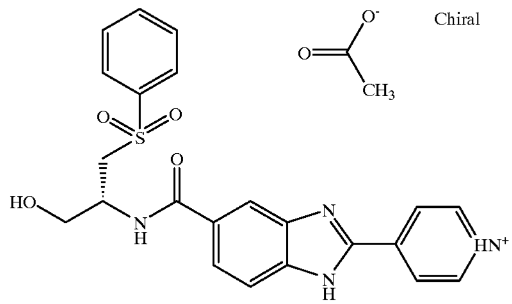 | M.W. = 436.49 $C_{22}H_{20}N_4O_4S$ | 437.0 | a) |
| 149 | 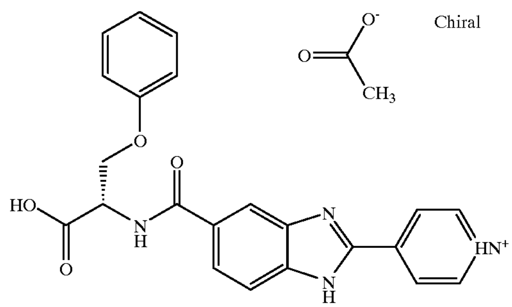 | M.W. = 402.41 $C_{22}H_{18}N_4O_4$ | 403.0 | a) |
| 150 | 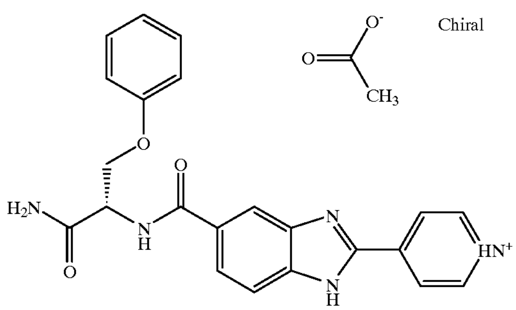 | M.W. = 401.43 $C_{22}H_{19}N_5O_3$ | 402.0 | a) |
| 151 | 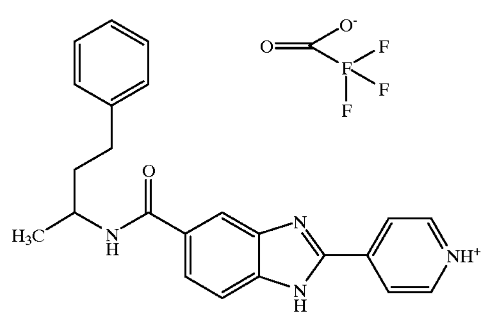 | M.W. = 370.46 $C_{23}H_{22}N_4O$ | 371.2 | a) |
| 152 | 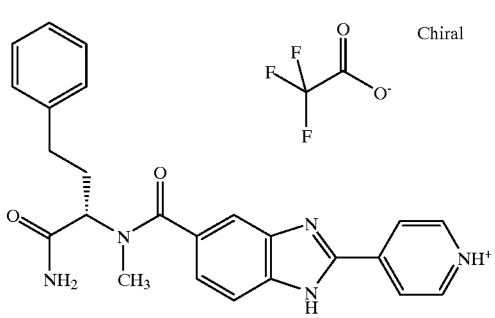 | M.W. = 413.48 $C_{24}H_{23}N_5O_2$ | 414 | a) |

TABLE 2-continued

| Example | Structure | Empirical formula | MS (M + H) | Note |
|---------|-----------|-------------------|------------|------|
| 153 | 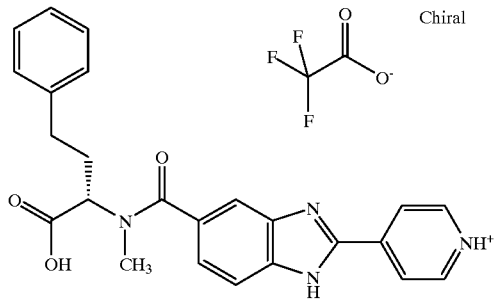 Chiral | M.W. = 414.47 $C_{24}H_{22}N_4O_3$ | 415.2 | a) |
| 154 | 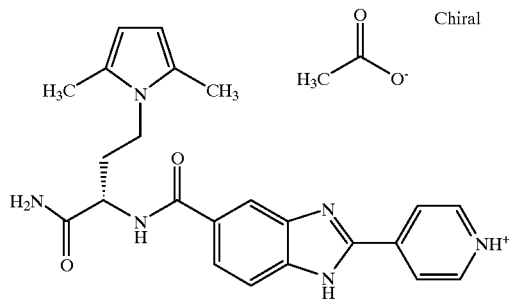 Chiral | M.W. = 416.49 $C_{23}H_{24}N_6O_2$ | 417.3 | a) |

M.W. means molecular weight

EXAMPLE 155

The following compounds were prepared according to process variant a) as in the general working procedure:

a) Preparation of 2-fluoroisonicotinic acid:

5.00 g (45 mmol) of 2-fluoro-4-methylpyridine and 1.00 g (17 mmol) of KOH were treated with 50 ml of pyridine and heated under reflux. 20.00 g (127 mmol) of potassium permanganate were added in portions in the course of 30 minutes at this temperature and the mixture was heated under reflux for a further 1.5 h. It was then cooled in an ice bath, treated with 100 ml of water, and brought to a pH of 1 using concentrated hydrochloric acid. After the addition of 100 ml of ethyl acetate, the insoluble residue was filtered off and the aqueous phase was extracted a further two times with 100 ml of ethyl acetate each time.

The combined ethyl acetate phases were dried over magnesium sulfate and concentrated under reduced pressure. 2.70 g of 2-fluoroisonicotinic acid were obtained. Yield: 42%.

b) Preparation of (2-fluoropyridin-4-yl)methanol:

12.60 g (89 mmol) of 2-fluoroisonicotinic acid were introduced into 300 ml of toluene with 13.3 ml (95 mmol) of triethylamine and treated with 9.08 ml (95 mmol) of ethyl chloroformate and stirred at RT (20°–23° C.) for 1 h. The triethylammonium chloride was then filtered off and the toluene phase was concentrated under reduced pressure. The residue was taken up in 200 ml of absolute THF and cooled to −78° C. A suspension of lithium aluminum hydride (3.55 g, 95 mmol) in THF was added dropwise at this temperature and the mixture was stirred for a further 30 minutes. The reaction mixture was then allowed to come to RT and poured onto 1 l of ice water. Extraction four times with 300 ml of ethyl acetate, drying of the combined ethyl acetate phase over magnesium sulfate, and evaporation of the solvent yielded the crude product, which after purification by means of medium-pressure chromatography (CH$_2$Cl$_2$/MeOH such as 9/1) yielded 5.10 g (40 mmol) of the desired product. Yield: 45%.

c) Preparation of 2-fluoropyridine-4-carbaldehyde:

A solution of 5 g (39 mmol) of (2-fluoropyridin-4-yl) methanol in dichloromethane was added dropwise to a solution of 4.6 ml (54 mmol) of oxalyl chloride and 7.6 ml (106 mmol) of dimethyl sulfoxide (DMSO) in 450 ml of dichloromethane at −78° C. and the mixture was stirred for 15 minutes. 24 ml (180 mmol) of triethylamine were then added and the reaction solution was slowly warmed to RT. It was poured onto 500 ml of water and washed once each with 10% strength citric acid (200 ml) and 10% strength sodium carbonate solution. The dichloromethane phase was dried over magnesium sulfate and concentrated under reduced pressure. Yield: 4.60 g (37 mmol), 94%.

d) Preparation of 2-(2-fluoropyridin-4-yl)-1H-benzimidazole-5-carboxylic acid:

2.00 g (15 mmol) of 2-fluoropyridine-4-carbaldehyde were suspended in 100 ml of nitrobenzene with 2.40 g (15 mmol) of 3,4-diaminobenzoic acid and stirred at 145° C. for 3 h. The reaction solution was then cooled to 0° C. and the crystals slowly forming in the course of this were filtered off. 2.53 g (9.8 mmol) of the desired benzimidazole were obtained. Yield: 62%.

e) Preparation of 2-(2-methylaminopyridin-4-yl)-1H-benzimidazole-5-carboxylic acid:

100 mg (0.38 mmol) of 2-(2-fluoropyridin-4-yl)-1H-benzimidazole-5-carboxylic acid were dissolved in 5 ml of methanol. The methanol solution was then saturated with gaseous methylamine and the reaction mixture was stirred at 120° C. in an autoclave for 10 h under autogenous pressure. Medium-pressure chromatography (CH$_2$Cl$_2$/MeOH=2/1) yielded 56 mg (0.21 mmol) of the substitution product. Yield: 55%.

f) Preparation of 2-(S)-{[2-(2-methylaminopyridin-4-yl)-1H-benzimidazole-5-carbonyl]amino}-4-pyrrol-1-yl butyric acid trifluoroacetate:

50 mg (0.186 mmol) of 2-(2-fluoropyridin-4-yl)-1H-benzimidazole-5-carboxylic acid were dissolved in 3 ml of DMF and cooled to 0° C. 100 µl (0.58 mmol) of diisopropylethylamine and 64 mg (0.195 mmol) of TOTU were added to this mixture. 33 mg (0.196 mmol) of 2-(S)-amino-4-pyrrol-1-ylbutyric acid were then added and the reaction solution was allowed to come to RT. It was stirred for 18 h, then poured onto 20 ml of 10% strength sodium hydrogencarbonate solution, and extracted three times with n-butanol (50 ml). After the evaporation of the butanol, the residue was purified by means of preparative HPLC (acetonitrile, 0.1% strength trifluoroacetic acid). 40 mg (0.075 mmol) of the coupled product were thus obtained. Yield: 42%.

The examples mentioned in Table 3 which follows were prepared analogously:

TABLE 3

| Example | Structure | | Empirical formula | MS (M + H) | Note |
|---------|-----------|---|-------------------|------------|------|
| 156 | 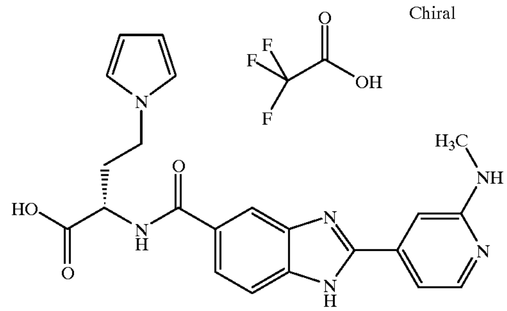 | Chiral | $C_{24}H_{23}F_3N_6O_5$ | 419.2 | a) |
| 157 | 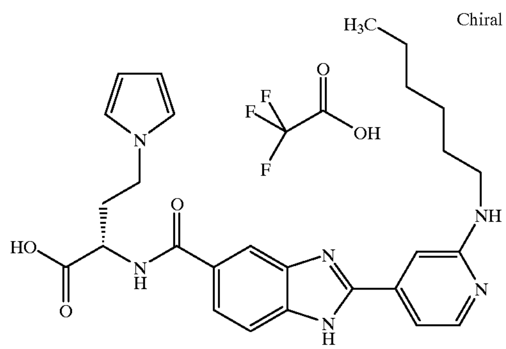 | Chiral | $C_{29}H_{33}F_3N_6O_5$ | 489.3 | a) |
| 158 | 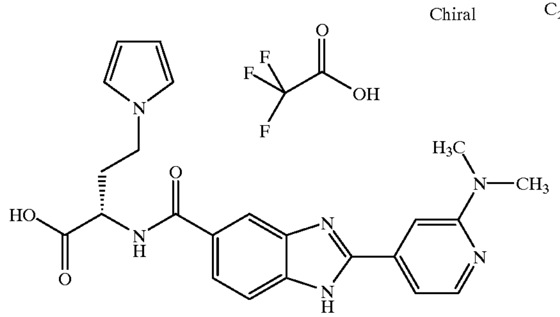 | Chiral | $C_{25}H_{25}F_3N_6O_5$ | 433.0 | a) |
| 159 | 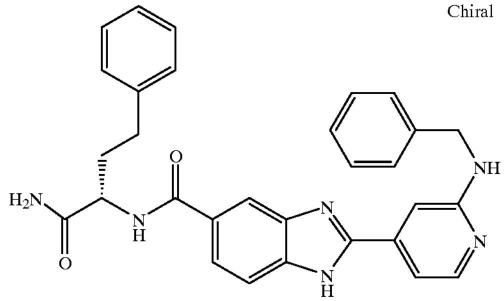 | Chiral | $C_{30}H_{28}N_6O_2$ | 505.2 | a) |

TABLE 3-continued

| Example | Structure | | Empirical formula | MS (M + H) | Note |
|---|---|---|---|---|---|
| 160 | 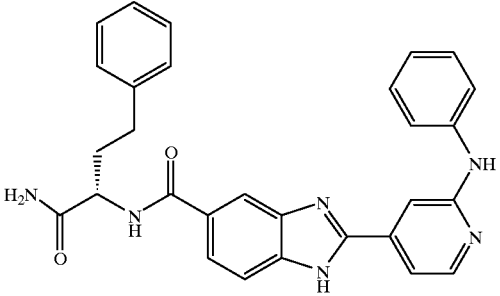 | Chiral | $C_{29}H_{26}N_6O_2$ | 491.2 | a) |
| 161 | 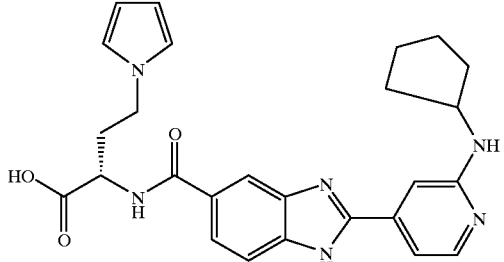 | | $C_{26}H_{28}N_6O_3$ | 473.3 | a) |

EXAMPLE 162

The following compound was prepared according to process variant a) as in the general working procedure:

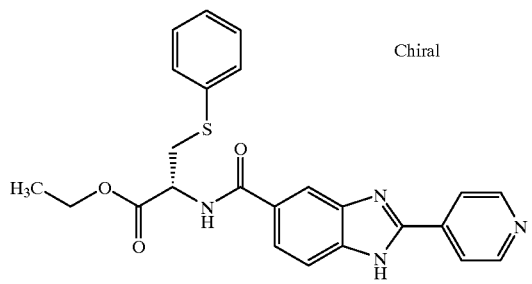

Chiral a) Preparation of ethyl 2-(S)-amino-3-phenylsulfanyl propionate:

1.7 ml (23 mmol) of thionyl chloride were added dropwise at −10° C. to 1.00 g (5 mmol) of 2-(S)-amino-3-phenylsulfanylpropionic acid dissolved in 10 ml of methanol. The reaction solution was then allowed to come to RT and 5 ml of DMF were added. It was then heated at 70° C. for 23 h and, after cooling to −10° C., 1 ml (13.5 mmol) of thionyl chloride was added again. It was then stirred at 70° C. for a further 14 h. After the evaporation of the liquid phase, the residue was taken up in water and rendered basic with concentrated aqueous ammonia solution and extracted three times with ethyl acetate (75 ml each time). After drying over magnesium sulfate and evaporation, the product was obtained as an oil that was used without further purification for the coupling with the carboxylic acid component. Yield: 830 mg (3.7 mmol), 74%.

b) Preparation of ethyl 3-phenylsulfanyl-2-(S)-[(2-pyridin-4-yl-1H-benzimidazole-5-carbonyl)amino]propionate:

In this case, the standard TOTU coupling with 188 mg (0.83 mmol) of ethyl 2-(S)-amino-3-phenylsulfanylpropionate and 200 mg (0.83 mmol) of 2-pyridin-4-yl-1H-benzimidazole-5-carboxylic acid yielded the desired product. Yield: 43% (160 mg, 0.36 mmol).

The examples mentioned in Table 4 which follows were prepared analogously:

TABLE 4

| Example | Structure | | Empirical formula | MS (M + H) | Note |
|---|---|---|---|---|---|
| 163 | 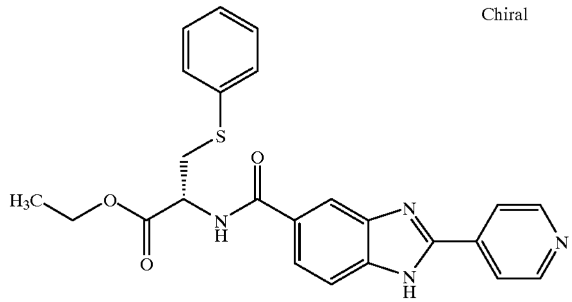 | Chiral | C₂₄H₂₂N₄O₃S | 447.1 | a) |
| 164 | 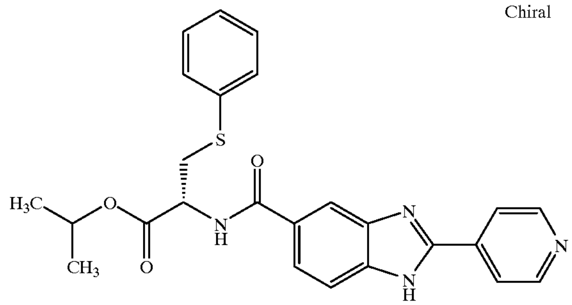 | Chiral | C₂₅H₂₄N₄O₃S | 461.3 | a) |
| 165 | 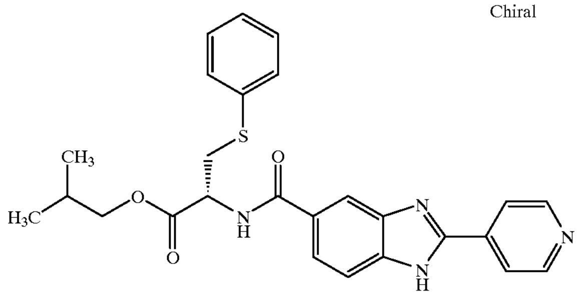 | Chiral | C₂₆H₂₆N₄O₃S | 475.2 | a) |
| 166 | 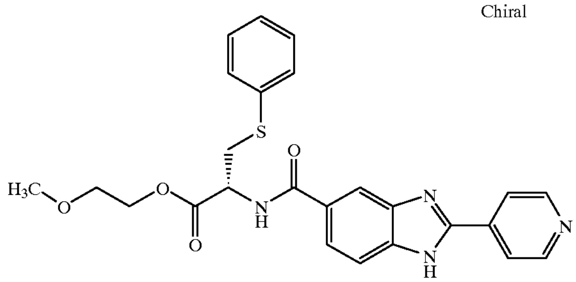 | Chiral | C₂₅H₂₄N₄O₄S | 477.3 | a) |

EXAMPLE 167

The following compound was prepared according to process variant a) as in the general working procedure:

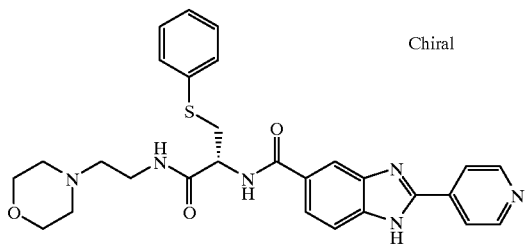

a) Preparation of 2-pyridin-4-yl-1H-benzimidazole-5-carboxylic acid [1-(2-morpholin-4-ylethylcarbamoyl)-2-phenylsulfanylethyl]amide:

100 mg (0.24 mmol) of 3-phenylsulfanyl-2-[(2-pyridin-4-yl-1H-benzimidazole-5-carbonyl)amino]propionic acid were dissolved in 10 ml of DMF. 68 μl (0.39 mmol) of diisopropylethylamine and 248 mg (0.48 mmol) of benzotriazol-1-yloxytripyrrolidinephosphonium hexafluorophosphate were added to this mixture at 0° C. It was then allowed to come to RT and stirred for 24 h. The solvent was removed under high vacuum at RT and the residue was purified by means of medium-pressure chromatography ($CH_2Cl_2$/MeOH=8/2). Yield: 73 mg (0.1376 mmol), 57%.

The examples mentioned in Table 5 which follows were prepared analogously:

TABLE 5

| Example | Structure | | Empirical formula | MS (M + H) | Note |
|---|---|---|---|---|---|
| 168 | 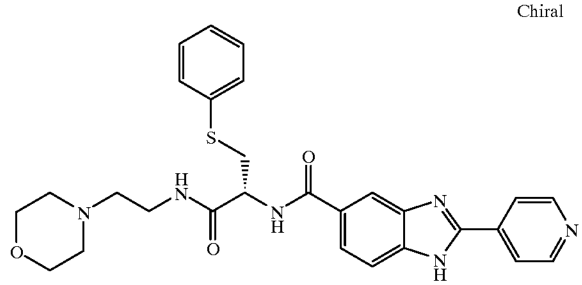 | Chiral | $C_{26}H_{30}N_6O_3S$ | 531.2 | a) |
| 169 | 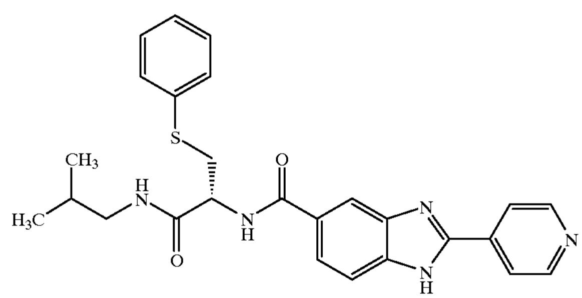 | Chiral | $C_{26}H_{27}N_5O_2S$ | 474.2 | a) |
| 170 | 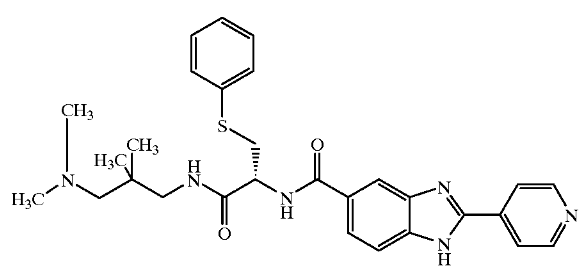 | Chiral | $C_{29}H_{34}N_6O_2S$ | 531.2 | a) |

TABLE 5-continued

| Example | Structure | | Empirical formula | MS (M + H) | Note |
|---|---|---|---|---|---|
| 171 | 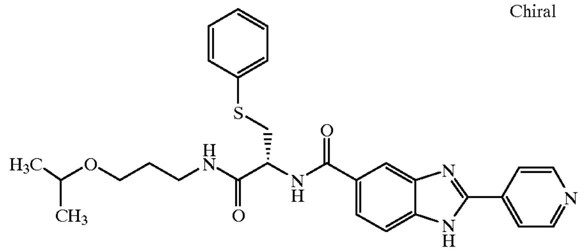 | Chiral | $C_{28}H_{31}N_5O_3S$ | 518.2 | a) |
| 172 | 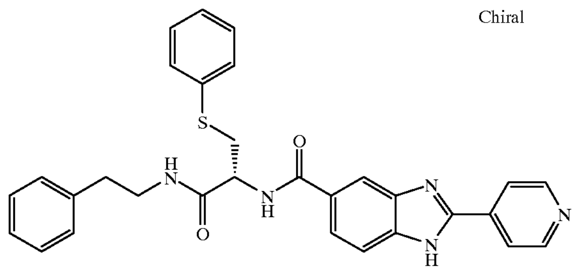 | Chiral | $C_{30}H_{27}N_5O_2S$ | 522.7 | a) |
| 173 | 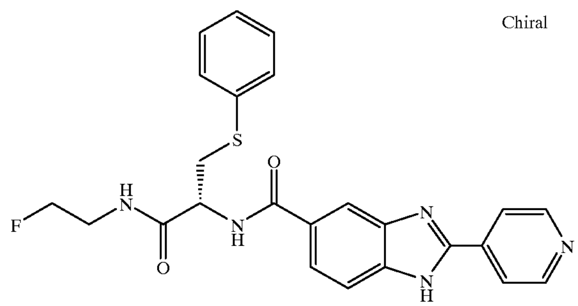 | Chiral | $C_{24}H_{22}FN_5O_2S$ | 464.1 | a) |
| 174 | 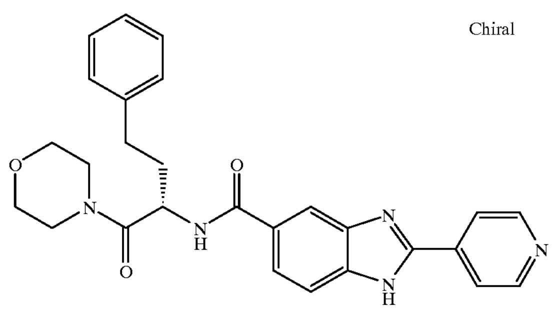 | Chiral | $C_{27}H_{27}N_5O_3$ | 470.2 | a) |
| 175 | 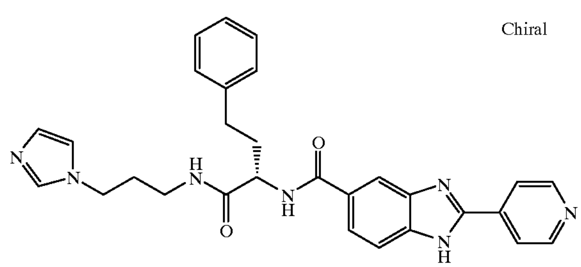 | Chiral | $C_{29}H_{29}N_7O_2$ | 508.2 | a) |

TABLE 5-continued

| Example | Structure | | Empirical formula | MS (M + H) | Note |
|---|---|---|---|---|---|
| 176 | 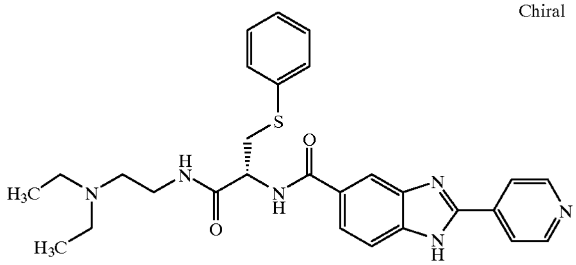 | Chiral | C$_{28}$H$_{32}$N$_6$O$_2$S | 517.3 | a) |
| 177 | 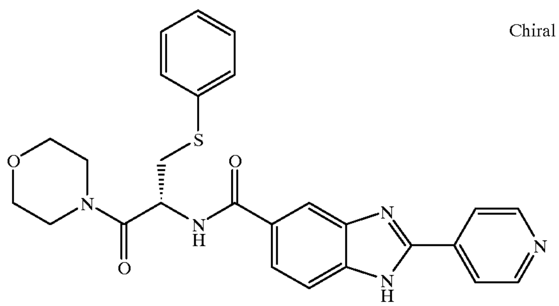 | Chiral | C$_{26}$H$_{25}$N$_5$O$_3$S | 488.2 | a) |
| 178 | 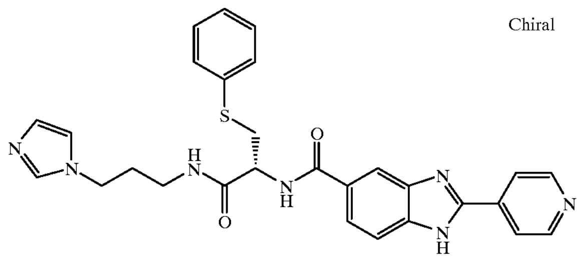 | Chiral | C$_{28}$H$_{27}$N$_7$O$_2$S | 526.2 | a) |

EXAMPLE 179

The following compound was prepared according to process variant a) as in the general working procedure:

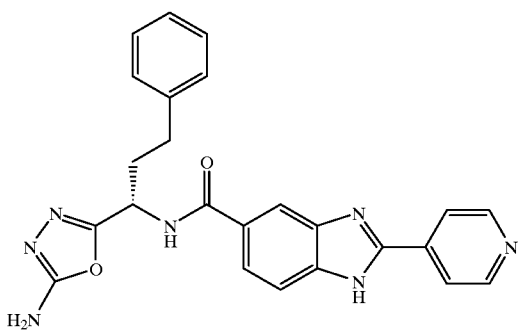

a) Preparation of Z-homophenylalanine hydrazide:

5 g (16 mmol) of Z-homophenylalanine were dissolved in 100 ml of methyl tert-butyl ether at RT, treated with 3.3 g (16 mmol) of N,N'-dicyclohexylcarbodiimide and 50 mg of dimethylaminopyridine, and the mixture was stirred at RT for 2 h. The reaction mixture was then filtered through a folded filter, and the filtrate was washed with 1M potassium hydrogensulfate solution, saturated sodium hydrogencarbonate solution, and water. The organic phase was dried over magnesium sulfate, filtered, and concentrated under reduced pressure. The residue was dissolved in 20 ml of dry ethanol, treated with 0.78 ml (16 mmol) of hydrazine hydrate, and stirred at RT for 2 h. The course of the reaction was monitored by means of thin-layer chromatography (TLC), and after completion of the reaction the mixture was concentrated under reduced pressure. The residue was recrystallized from ethyl acetate/n-heptane (1/1) and Z-homophenylalanine hydrazide was obtained, which was reacted further in this manner.

b) Preparation of benzyl [1-(5-amino-[1,3,4]oxadiazol-2-yl)-3-phenylpropyl]carbamate:

0.66 g of Z-homophenylalanine hydrazide was suspended in 10 ml of water at RT, treated with 200 mg of potassium hydrogencarbonate, and 0.4 ml of a cyanogen bromide solution (5 M in acetonitrile) was then added. The mixture was stirred at RT for 3 h and then extracted a number of times with ethyl acetate. The combined organic phases were washed with saturated sodium chloride solution, dried over magnesium sulfate, filtered, and concentrated under reduced pressure. The residue was stirred with methyl tert-butyl ether, filtered off with suction, and dried under reduced pressure. The benzyl [1-(5-amino-[1,3,4]oxadiazol-2-yl)-3-phenylpropyl]carbamate was employed in the next stage without further purification.

c) Preparation of 5-(1-amino-3-phenylpropyl)-[1,3,4]oxadiazol-2-ylamine:

0.33 g of benzyl [1-(5-amino-[1,3,4]oxadiazol-2-yl)-3-phenylpropyl]carbamate were dissolved in 50 ml of dry methanol at RT, treated under argon with hydrogenation catalyst (10% palladium on carbon), and hydrogenated at RT for 3 h. The reaction mixture was filtered off through Celite, the filtrate was concentrated under reduced pressure, and the residue was dried under high vacuum. 5-(1-Amino-3-phenylpropyl)-[1,3,4]oxadiazol-2-ylamine was obtained, which was employed in the next stage without further purification.

d) Preparation of 2-pyridin4-yl-1H-benzimidazole-5-carboxylic acid [1-(5-amino-[1,3,4]oxadiazol-2-yl)-3-phenylpropyl]amide:

0.18 g of 5-(1-amino-3-phenylpropyl)-[1,3,4]oxadiazol-2-ylamine was dissolved in 10 ml of dry dimethylformamide at RT, treated with 200 mg of 2-pyridin-4-yl-1H-benzimidazole-5-carboxylic acid, 270 mg of TOTU, and 0.12 ml of diisopropylamine, and stirred at RT for 4 h. The reaction mixture was concentrated, and the residue was taken up in ethyl acetate and washed successively with water, saturated sodium hydrogencarbonate solution, water, and saturated sodium chloride solution. The organic phase was dried over magnesium sulfate, filtered, and concentrated. The residue was stirred with methyl tert-butyl ether, filtered off, and dried under high vacuum. 2-Pyridin4-yl-1H-benzimidazole-5-carboxylic acid [1-(5-amino-[1,3,4]oxadiazol-2-yl)-3-phenylpropyl]amide, which melts at 160° C. with decomposition, is obtained.

EXAMPLE 180

The following compound was prepared according to process variant a) as in the general working procedure:

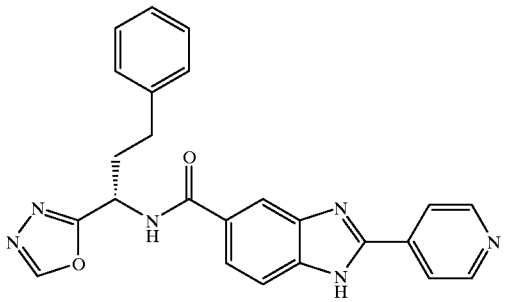

a) Z-Homophenylalanine hydrazide was prepared as described in Example 179.

b) Preparation of benzyl (1-[1,3,4]oxadiazol-2-yl-3-phenylpropyl)carbamate:

1 g of Z-homophenylalanine hydrazide was suspended in 8 ml of ethyl orthoformate at RT and the mixture was heated under reflux for 4 h. The cooled reaction mixture was treated with methyl tert-butyl ether, the precipitate was filtered off, and the filtrate was concentrated under reduced pressure. The residue was chromatographed on silica gel using ethyl acetate/n-heptane (1/1) and yielded benzyl (1-[1,3,4]oxadiazol-2-yl-3-phenylpropyl)carbamate, which was employed in the next stage.

c) The preparation of 1-[1,3,4]oxadiazol-2-yl-3-phenylpropylamine is carried out analogously to the preparation of 5-(1-amino-3-phenylpropyl)-[1,3,4]oxadiazol-2-ylamine as described in Example 179.

d) Preparation of 2-pyridin-4-yl-1H-benzimidazole-5-carboxylic acid (1-[1,3,4]oxadiazol-2-yl-3-phenylpropyl)amide:

220 mg of 1-[1,3,4]oxadiazole-2-yl-3-phenylpropylamine were dissolved in 10 ml of dry dimethylformamide at RT, treated with 260 mg of 2-pyridin-4-yl-1H-benzimidazol-5-carboxylic acid, 350 mg of TOTU, and 0.15 ml of diisopropylamine, and stirred at RT for 4 h. The reaction mixture was concentrated, the residue was taken up in ethyl acetate, and the mixture was washed successively with water, saturated sodium hydrogencarbonate solution, water, and saturated sodium chloride solution. The organic phase was dried over magnesium sulfate, filtered, and concentrated. The residue was chromatographed on silica gel using dichloromethane/methanol (8/1) and yielded 2-pyridin-4-yl-1H-benzimidazole-5-carboxylic acid (1-[1,3,4]oxadiazol-2-yl-3-phenylpropyl)amide, which melts at 103° C. with decomposition.

EXAMPLE 181

The following compound was prepared according to process variant a) as in the general working procedure:

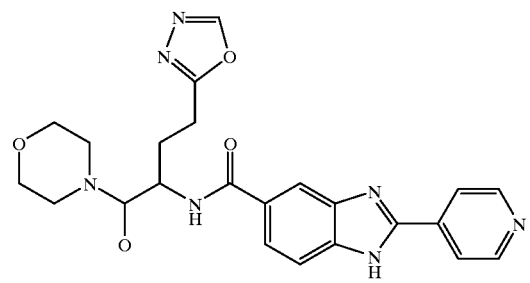

a) Preparation of L-N-benzoyloxycarbonyl-4-([1,3,4]oxadiazol-2-yl)-2-aminobutanoic acid:

1 g of Z-glutamic acid y-hydrazide was suspended in 20 ml of trimethyl orthoformate with 30 mg of para-toluenesulfonic acid and the mixture was stirred at RT. The suspension clarified within 30 minutes, and the solution resulting in this way was filtered and diluted with 100 ml of water. After addition of 20 ml of 2N hydrochloric acid, it was extracted five times with ethyl acetate and the combined organic phases were then dried over sodium sulfate. After filtration, the solution was concentrated under reduced pressure and a viscous opaque mass was obtained.

b) Preparation of L-N-benzyloxycarbonyl-4-([1,3,4]oxadiazol-2-yl)-2-aminobutanoic acid morpholide:

300 mg of L-N-benzyloxycarbonyl-4-([1,3,4]oxadiazol-2-yl)-2-aminobutanoic acid and 200 mg of EDC hydrochloride were dissolved in 20 ml of dichloromethane and then treated with 2 ml of morpholine. After stirring at RT for two days, the solution was extracted three times by shaking with saturated sodium hydrogencarbonate solution, three times by shaking with aqueous citric acid solution, and once by shaking with saturated sodium hydrogencarbonate solution. The organic phase was dried over sodium sulfate and concentrated after filtration under reduced pressure. A yellowish opaque residue was obtained.

c) Preparation of L-4-([1,3,4]oxadiazol-2-yl)-2-aminobutanoic acid morpholide:

70 mg of L-N-benzoyloxycarbonyl-4-([1,3,4]oxadiazol-2-yl)-2-aminobutanoic acid morpholide were dissolved in 20 ml of methanol and treated with one spatula tipful of palladium on active carbon (5%) and the suspension was stirred under a hydrogen atmosphere. After 3 h, the catalyst was filtered off through Celite and the filtrate was concentrated under reduced pressure after filtration through a 0.45 μm filter.

d) Preparation of 2-pyridin-4-yl-1H-benzimidazole-5-carboxylic acid [1-(morpholine-4-carbonyl)-3-[1,3,4]oxadiazol-2-ylpropyl]amide:

43 mg of 2-pyridin-4-yl-1H-benzimidazole-5-carboxylic acid, 75 mg of HATU, and 51 mg of diisopropylethylamine were dissolved in 1 ml of N,N-dimethylformamide and treated with 40 mg of L-4-([1,3,4]oxadiazol-2-yl)-2-aminobutanoic acid morpholide in 0.4 ml of N,N-dimethylformamide after stirring for 10 min. After stirring at RT for 7 h, 200 mg of aminomethylpolystyrene (1.37 mmol/g) and 20 ml of N,N-dimethylformamide were added. After 1 h, the mixture was filtered and the N,N-dimethylformamide was distilled off under reduced pressure. The residue was digested with cold acetonitrile. The insoluble residue was discarded and the acetonitrile solution was subjected to gradient filtration on RP18 silica gel using water/acetonitrile mixtures. A glassy yellowish solid was isolated.

EXAMPLE 182

3-Phenoxy-2-[(2-pyridin-4-yl-1H-benzimidazole-2-carbonyl)amino]propionic acid hydrogenacetate

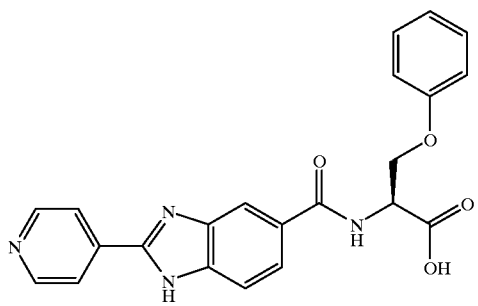

a) 2-Pyridin-4-yl-1H-benzimidazole-5-carboxylic acid (in the following called compound I) and 15.2 g (0.1 mol) of 3,4-diaminobenzoic acid were suspended in 1 l of nitrobenzene and treated with 11.2 g (0.104 mol) of pyridine-4-aldehyde. The mixture was then heated with vigorous stirring for 8 h at 145° C. to 155° C. After cooling of the solution, the precipitated product was filtered off with suction and washed thoroughly with ethyl acetate and dichloromethane. For purification, the crude product was heated to boiling in a mixture of 300 ml of methanol, 100 ml of dichloromethane, and 10 ml of DMF. After cooling, the undissolved product was filtered off and washed with dichloromethane. The material obtained was taken up in approximately 200 ml of DMSO, then the mixture was heated until a homogeneous solution resulted—cooled to approximately 50° C. and treated with 200 ml of methanol—the product crystallized after approximately 30 min at RT. The precipitate was filtered off and washed thoroughly with methanol. Yield: 19.4 g.

b) (S)-2-Amino-3-phenoxypropionic acid hydrochloride (m.w. 217.6):

2.8 g of trt-Ser-OMe (Bachem), 0.75 of phenol, and 2.25 g of triphenylphosphine were dissolved together in 60 ml of THF, absolute, and treated dropwise with 1.49 g of diethyl azodicarboxylate at 0° C. in the course of 30 min. The reaction mixture was stirred at 0° C. for 30 min and warmed to RT (about 1 h). For working-up, the solvent was removed under reduced pressure and the crude product was purified by chromatography on silica gel (heptane/ethyl acetate=1.5/1). The methyl (S)-2-tritylamino-3-phenoxypropionate thus obtained crystallized slowly in long needles, and was heated under reflux for 1 h in 5 M HCl to remove the protective groups. The reaction solution was evaporated to dryness under reduced pressure by coevaporating a number of times with toluene and the residue was recrystallized from a little tert-butanol.

Process step c):

239 mg of 2-pyridin-4-yl-1H-benzimidazole-5-carboxylic acid from a) were suspended in 10 ml of DMF and treated successively with 328 mg of TOTU and 0.17 ml of ethyldiisopropylamine. The mixture was stirred at RT for 45 min and 217.6 mg of (S)-2-amino-3-phenoxypropionic acid hydrochloride prepared as under b) were added to the resulting clear solution, and 0.34 ml of ethyldiisopropylamine was added. After stirring for 4 h, the mixture was concentrated under reduced pressure and the title compound was isolated by flash chromatography on silica gel (DCM/MeOH/AcOH/water=70/10/1/1). The title compound obtained had a molecular weight of 402.41, molecular mass of 402, and the empirical formula $C_{22}H_{18}N_4O_4$.

EXAMPLE 183

3-Phenylamino-2-[(2-pyridin-4-yl-1H-benzimidazole-5-carbonyl)amino]propionic acid hydrogenacetate

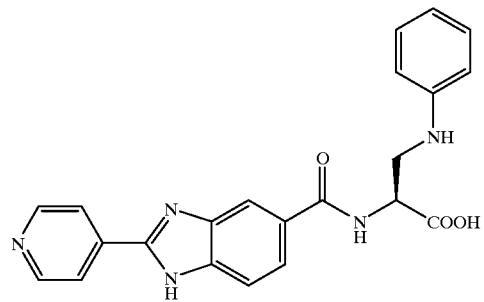

a) L-2-Amino-3-phenylaminopropionic acid:

2.74 g of triphenylphosphine were dissolved in 30 ml of acetonitrile with warming and cooled to −35° C. to −45° C. with exclusion of moisture (the phosphine precipitated in finely divided form in the course of this) and 1.82 ml of diethyl azodicarboxylate were then added dropwise at this temperature in the course of 40 min. The mixture was stirred at −35° C. for 15 min. A solution of 2.5 g of N-benzyloxycarbonyl-L-serine in 5 ml in acetonitrile and 2 ml of THF was added dropwise to this mixture, and in the course of this the temperature was not allowed to rise above −35° C. The mixture was then allowed to react at −35° C. for 1 h and warmed to RT. The reaction solution was freed from the solvent under reduced pressure and the crude product was immediately purified using medium-pressure chromatography on silica gel (DCM/AcCN=20/1). After removing the solvent, 1.4 g of clean N-benzoyloxycarbonyl-L-serine-β-lactone were obtained (see also Org. Synth. 70 (1991) 1ff) in fine needles. 1.2 g of the lactone were dissolved in 10 ml of acetonitrile and heated under reflux for 2 h with 0.51 g of aniline. After removal of the solvent, the product was isolated by chromatography on silica gel (DCM/MeOH/AcOH=10/5/1). 1.1 g (68%) of L-2-benzyloxycarbonylamino-3-phenylaminopropionic acid were thus obtained.

To remove the protective group, the Z-protected derivative was dissolved in methanol, 80 mg of catalyst (10% Pd—C) were added under inert gas, and hydrogen was passed in until the Z-protective group was completely removed. After filtering off the catalyst and evaporating the filtrate, 0.58 g of L-2-amino-3-phenylaminopropionic acid (92%) was obtained as yellowish soft needles.

Process step b):

239 mg of compound I prepared as in Example 182 were suspended in 10 ml of DMF and treated successively with 328 mg of TOTU and 0.17 ml of ethyldiisopropylamine. The mixture was stirred at RT for 45 min and 180.2 mg of (S)-2-amino-3-phenylaminopropionic acid prepared according to a) and 0.34 ml of ethyldiisopropylamine were added to the resulting clear solution. After stirring for 4 h, the mixture was concentrated under reduced pressure and the title compound was isolated by flash chromatography on silica gel (DCM/MeOH/AcOH/water=70/10/1/1). The title compound obtained had a molecular weight of 401.43 and the empirical formula $C_{22}H_{19}N_5O_3$.

EXAMPLE 184

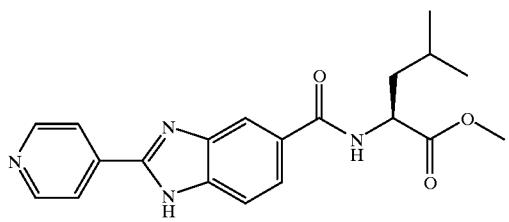

239.2 mg (1 mmol) of compound I prepared as in Example 182 were treated successively with 182.7 mg (1 mmol) of H-Leu-OMe HCl, 328 mg (1 mmol) of TOTU, and 0.34 ml (2 mmol) of ethyldiisopropylamine in approximately 8 ml of DMF. After 6 h at RT, the solvent was distilled off under reduced pressure, the residue was taken up in ethyl acetate, and the mixture was washed three times each with water and saturated NaCl solution. The organic phase was dried and evaporated to dryness under reduced pressure. The residue was purified by flash chromatography on silica gel (DCM/MeOH=15/1). Yield: approximately 200 mg.

EXAMPLE 185

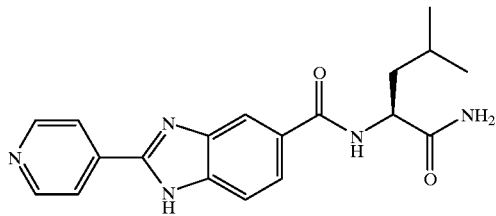

239.2 mg (1 mmol) of compound I prepared as in Example 182 were treated successively with 166.6 mg (1 mmol) of H-Leu-NH$_2$.HCl, 328 mg (1 mmol) of TOTU, and 0.34 ml (2 mmol) of ethyldiisopropylamine in approximately 8 ml of DMF. After 6 h at RT, the solvent was distilled off under reduced pressure, the residue was taken up in ethyl acetate, and the mixture was washed once with water. The aqueous phase was then saturated with NaCl and extracted twice with ethyl acetate/THF (1/1). The combined organic phases were washed once with saturated NaCl solution, dried, and evaporated to dryness under reduced pressure. The residue was precipitated with dichloromethane and filtered off. For purification, the crude product was boiled with DCM/ethyl acetate (1/1), filtered off, and washed thoroughly with DCM/ether. Yield: approximately 200 mg.

EXAMPLE 186

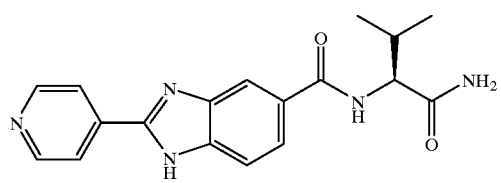

239.2 mg (1 mmol) of compound I prepared as in Example 182 were treated successively with 152.6 mg (1 mmol) of H-Val-NH$_2$.HCl, 328 mg (1 mmol) of TOTU, and 0.34 ml (2 mmol) of ethyldiisopropylamine in approximately 8 ml of DMF. After 6 h at RT, the solvent was distilled off under reduced pressure, the residue was taken up in ethyl acetate, and the mixture was washed once with water. The aqueous phase was then saturated with NaCl and extracted twice with ethyl acetate/THF (1/1). The combined organic phases were washed once with saturated NaCl solution, dried, and evaporated to dryness under reduced pressure. The residue was precipitated with dichloromethane and filtered off. For purification, the crude product was boiled with DCM/ethyl acetate (1/1), filtered off, and washed thoroughly with DCM/ether. Yield: approximately 200 mg.

EXAMPLE 187

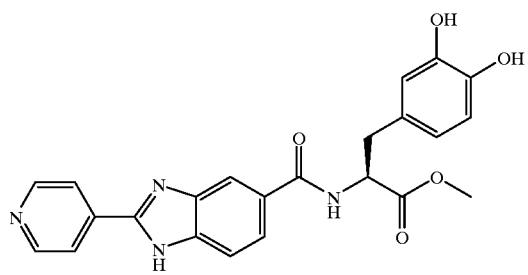

239.2 mg (1 mmol) of compound I prepared in Example 182 were treated successively with 247.7 mg (1 mmol) of H-Dopa-OMe.HCl, 328 mg (1 mmol) of TOTU, and 0.34 ml (2 mmol) of ethyldiisopropylamine in approximately 8 ml of DMF. After 6 h at RT, the solvent was distilled off under reduced pressure, the residue was taken up in ethyl acetate, and the mixture was washed three times each with water and saturated NaCl solution. The organic phase was dried and evaporated to dryness under reduced pressure. The residue was precipitated with dichloromethane and filtered off. For purification, the crude product was boiled with DCM/ethyl acetate (1/1), filtered off, and thoroughly washed with DCM/ether. Yield: approximately 200 mg.

EXAMPLE 188

The following compound was prepared according to process variant c) as in the general working procedure:

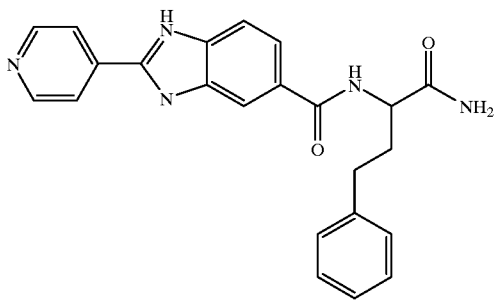

2.0 g of polystyrene-AM RAM, 160–200 microns (0.64 mmol/g)(Rapp Polymer) was added to a plastic syringe, allowed to swell in DMF for 20 min, and then treated with a solution of DMF/piperidine (1/1) for 20 min. After washing with DMF, DCM, and again with DMF, the resin was used as such in the next synthesis step.

Process step a):

DIC (0.59 ml, 3.84 mmol) was added to a solution of Fmoc-homoPheOH (0.71 g, 3.84 mmol) and HOBt hydrate (0.59 g, 3.84 mmol) in DMF. The resulting solution was drawn into the abovementioned syringe and the mixture was shaken at RT for 16 h. The resin was washed with DMF (10×15 ml), DCM (4×15 ml), and DMF (2×15 ml), and then stored at 4° C. To check the reaction, a KAISER test was carried out on a few resin beads.

Process step b):

The resin was deprotected and washed as described above. DIC (0.59 ml, 3.84 mmol) was added to a solution of 4-fluoro-3-nitrobenzoic acid (0.71 g, 3.84 mmol) and HOBt hydrate (0.59 g, 3.84 mmol) in DMF (approximately 15 ml). This solution was drawn into the syringe containing the prepared resin and the mixture was shaken at RT for 16 h. The resin was washed with DMF (10×15 ml), and stored at 4° C. To check the reaction, a KAISER test was carried out on a few resin beads.

Process step c):

A solution of 4-(aminomethyl)pyridine (1.4 ml, 12.8 mmol) in DMF (10 ml) was added to the prepared resin and the mixture was shaken at RT for 2 days. The resin was washed with DMF (8×15 ml), DCM (4×15 ml), and DMF (2×15 ml). Note: it was later found that simple heating of the resin mixture in DMA (dimethylacetamide instead of DMF) for 16 h afforded the desired hydroxybenzimidazole; it was thus possible to accelerate the synthesis.

Process step d):

A solution of the resin in DMA was packed into a sealable glass reactor and the reaction mixture was heated at 125° C. for 16 h with gentle agitation. It was possible to confirm that cyclization had taken place by means of GC/MS (after removal of an aliquot of the substance from the resin). After washing with DMA (5×15 ml), the resin was used as such in synthesis step e).

Process step e):

Tributylphosphine (0.6 ml) was added to a solution of the resin (0.5 g) from process step d) in DMA (5.0 ml) and the mixture was gently stirred at 150° C. for 6 h. The resin was then washed with DMF (20×10 ml), MeOH (10×10 ml), and DCM (10×10 ml).

Process step f) Cleavage and purification:

The resin obtained in process step e) was treated at RT for 3 h with TFA/H$_2$O (95/5). TFA/H$_2$O was removed under reduced pressure and a brown glassy solid was obtained as a crude product. The crude product was chromatographed on silica gel (flash chromatography; eluent: 95/5 DCM/2.0 M NH$_3$ in MeOH, then 92/9 DCM/2.0 M NH$_3$ in MeOH). The desired fractions were collected and the solvents were removed under reduced pressure. The product was obtained as a white solid. MS (ES; M+H$^+$=400). $^1$H-NMR corresponded to the abovementioned structural formula.

EXAMPLE 189

The following compound was prepared according to process variant c):

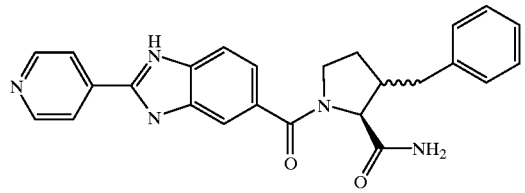

A) Synthesis of 3(R/S)-vinyl-2-(S)-azido-3-phenylpropionic acid:

a) Lithiumhydroxide (monohydrate, 21 g; 645 mmol) was added to a solution of ethyl 3-vinyl-4-phenylbutyrate (0.129 mol) in aqueous THF (120 ml/20 ml of H$_2$O). The reaction mixture was stirred overnight and then concentrated under reduced pressure. The residue was partitioned between AcOEt and aqueous HCl (1M), the phases were separated, and the aqueous phase was washed two times with AcOEt. The combined organic phases were washed with saturated sodium chloride solution, dried over MgSO$_4$, filtered, and evaporated under reduced pressure. 15.6 g (yield 62%) of acid were obtained, which was employed thus in the following reaction.

b) Triethylamine (1.27 ml) and, 15 minutes later, pivaloyl chloride (1.18 ml) were added to a cooled (−78° C.) solution of the abovementioned acid (1.74 g, 9.16 mmol) in anhydrous THF (10 ml). The mixture was stirred at 0° C. for 1 h and cooled to −78° C. In a separate flask, n-butyllithium (5.7 ml, 1.6 M in hexane) was slowly added to a cooled (−78° C.) solution of S-phenyloxazolidinone (1.64 g) in THF (36 ml). The solution was stirred at −78° C. for 1 h, warmed to 0° C., and added dropwise to the above solution via a cannula. After addition was complete, the solution was stirred at RT overnight. Saturated NH$_4$Cl solution (20 ml) was added and the solution was reduced to ⅓ of the volume under reduced pressure. The aqueous solution was extracted three times with dichloromethane, and the combined organic phases were washed with aqueous sodium hydroxide solution, dried over MgSO$_4$, filtered, and evaporated. The residue was purified by means of flash chromatography (silica gel, 5–20% AcOEt/hexane). 2.06 g (67% yield) of imide were obtained as a mixture of the two diastereomers.

c) 1,1,1,3,3,3-Hexamethyldisilazane potassium salt (14.6 ml, 0.5 molar solution in toluene) was added dropwise to a cooled (−78° C.) solution of the imide (1.88 g, 5.61 mmol) in anhydrous THF (15 ml). After 40 min, a cooled (−78° C.) solution of trimethylsilyl azide (2.51 g) in THF was added. After a further 35 min, acetic acid (1.47 ml) was added and the solution was stirred overnight at RT. The reaction mixture was partitioned between dichloromethane and saturated sodium chloride solution, and the organic phase was dried over MgSO$_4$, filtered, and evaporated. The residue was flash-chromatographed on silica gel (eluents: a) DCM/

MeOH/aq. ammonia=95/5/1; b) DCM; starting ratio a/b=1/ 10, up to pure DCM). 2.5 g (95% yield) of azido product were obtained.

d) 3 ml of hydrogen peroxide (30%) were added to a cooled solution (0° C.) of the above azido compound (2.5 g) in THF (20 ml), $H_2O$ (4 ml), and lithium hydroxide monohydrate (558 mg). The mixture was stirred at RT for 2 h and 19 ml of a 10% strength solution of sodium sulfate were then added. The solution was reduced to 1/10 of the original volume under reduced pressure, the residue obtained was extracted three times with ethyl acetate, and the combined organic phases were dried over $MgSO_4$, filtered, and concentrated to dryness under reduced pressure. The residue was purified on silica gel (flash chromatography, eluents: 1–5% MeOH in 1% strength aqueous ammonia solution/ 99% DCM). 912 mg of the desired acid (74% yield) were obtained.

B) Synthesis of 2-pyridin-4-yl-1H-benzimidazole-5-carbonyl-3-R,S-benzyl-S-prolinamide:

0.4 g of polystyrene Knorr resin (0.61 mmol/g) was added in a plastic syringe, allowed to swell in DMF for 20 min, and then treated for 20 min with a solution of DMF/piperidine (1/1). After washing with DMF, DCM, and again DMF, the resin was used thus in the next synthesis step.

Process step a):

A solution of 3(R/S)-vinyl-2-(S)-azido-3-phenylpropionic acid (see also steps a)–d) directly above; 0.28 mmol), PyBOP (0.28 mmol), and DIPEA (0.32 mmol) was added to the above resin. The resulting mixture was shaken at RT for 16 h. The resin was washed with MeOH (3×15 ml) and DCM (4×15 ml) and dried under reduced pressure. For checking the reaction, a KAISER test was carried out on some resin beads.

Process step b):

Cyclohexene (23 mmol) was added to a 2 M solution of dicyclohexyl-borane/dimethyl sulfide complex (11.6 mmol) in anhydrous diethyl ether under an inert gas atmosphere. After 1 h, a white solid was formed. The solvent was removed under reduced pressure and the above resin and 10 ml of DCM were added. The heterogeneous mixture was gently stirred for 2.5 h until the evolution of gas was complete. The resin was washed with MeOH and dried under reduced pressure. It was then stirred for 1 h with a 50/50 (vol/vol) mixture of ethanolamine and DMF and then washed with MeOH and DCM (three times each), then dried.

Process step c):

DIC (0.69 mmol) was added to a solution of 4-fluoro-3-nitrobenzoic acid (0.69 mmol) and HOAc (0.69 mmol) in DMF (approximately 5 ml). This solution was drawn into the syringe with the previously prepared resin and the mixture was shaken at RT for 16 h. The resin was washed with DMF (10×15 ml) and dried under vacuum. For monitoring the reaction, a KAISER test was carried out on some resin beads.

Process step d):

A solution of 4-(aminomethyl)pyridine (4.6 mmol) in DMF (4 ml) was added to the previously prepared resin and the mixture was shaken at RT for 32 days. The resin was washed with MeOH and DCM (3×15 ml each) and dried.

Process step e):

A solution of the resin in DMA was filled into a sealable glass reactor and the reaction mixture was heated at 125° C. with gentle agitation for 16 h. It was possible to confirm the cyclization that had taken place by GC/MS (after removal of an aliquot of the substance from the resin). The resin was washed with MeOH and DCM (3×15 ml each) and dried.

Process step f):

Tributylphosphine (0.5 ml) was added to a solution of the resin (0.021 mmol) from process step e) in DMA (3.0 ml) and the mixture was gently stirred at 125° C. for 5 h. The resin was then washed with DMF (2×10 ml), MeOH (2×10 ml), and DCM (3×10 ml) and dried under reduced pressure.

Process step g) Removal and purification:

The resin obtained in process step f) was treated with $TFA/H_2O$ (97/3) for 1 h at RT. $TFA/H_2O$ was removed under reduced pressure and a brown glassy solid was obtained as a crude product. The crude product was chromatographed on silica gel (flash chromatography; eluent: 95/5 DCM/2.0M $NH_3$ in MeOH, then 92/8 DCM/2.0M $NH_3$ in MeOH). The desired fractions were collected and the solvents were removed under reduced pressure. The product was obtained as a white solid. MS (ES; $M+H^+$=426). $^1$H-NMR corresponded to the abovementioned structural formula.

EXAMPLE 190

The following compound was prepared according to process variant c):

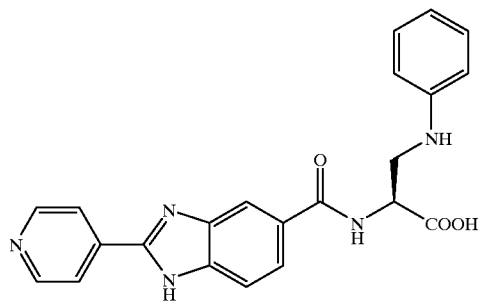

1.5 g of polystyrene Knorr resin (0.64 mmol/g) was added to a plastic syringe, swollen in 20 ml of DMF, and then treated for 20 min with a solution of DMF/piperidine (1/1). After washing with DMF, DCM, and again DMF, the resin was used thus in the next synthesis step.

Process step a):

A solution of Fmoc-3R,S-phenyl-S-proline (1.5 mmol), PyBOP (1.5 mmol), and DIPEA (2.1 mmol) in DCM was added to the resin. The resulting mixture was shaken at RT for 16 h. The resin was washed with DCM (4×15 ml), MeOH (2×15 ml), and DCM and dried under reduced pressure. For monitoring the reaction, a KAISER test was carried out on some resin beads.

Process step b):

The resin was reacted further to give the desired compound as described in Example 189 under process B.

MS (ES; $M+H^+$=412). $^1$H-NMR corresponded to the abovementioned structural formula.

EXAMPLE 191

The following compound was prepared according to process variant a) as in the general working procedure:

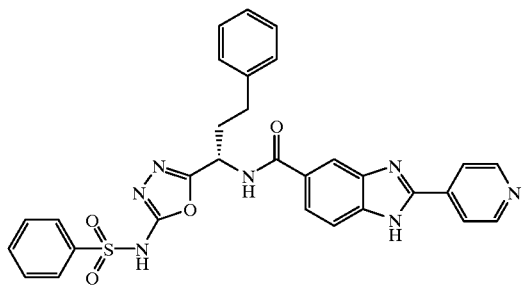

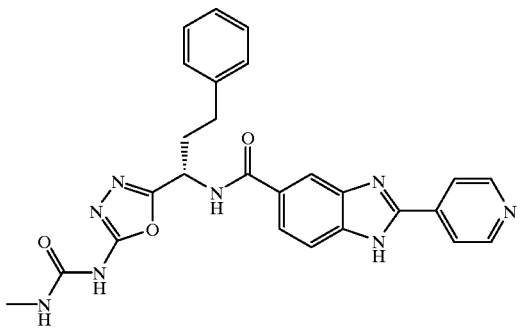

a) Preparation of Z-homophenylalanine hydrazide:

Z-Homophenylalanine hydrazide was prepared as described in Example 179a.

b) Preparation of benzyl [1-(5-amino-[1,3,4]oxadiazol-2-yl)-3-phenylpropyl]carbamate:

Benzyl [1-(5-amino-[1,3,4]oxadiazol-2-yl)-3-phenylpropyl]carbamate was prepared as described in Example 179b.

c) Preparation of benzyl [1-(5-benzenesulfonylamino-[1,3,4]oxadiazol-2-yl)-3-phenylpropyl]carbamate:

0.35 g of the compound according to Example 191b was dissolved in 5 ml of pyridine at RT, treated with 0.13 ml of benzenesulfonyl chloride, and stirred at 80° C. for 4 h. A further 0.13 ml of benzenesulfonyl chloride were added and the mixture was stirred at 80° C. for a further 2 h. The reaction mixture was concentrated in vacuo, and the residue was taken up in ethyl acetate, washed twice with water and once with saturated sodium chloride solution, dried over magnesium sulfate, filtered, and concentrated in vacuo. Benzyl [1-(5-benzenesulfonylamino-[1,3,4]oxadiazol-2-yl)-3-phenylpropyl]carbamate was obtained, which was reacted further without further purification.

d) Preparation of N-[5-(1-amino-3-phenylpropyl)-[1,3,4]oxadiazol-2-yl]benzenesulfonamide:

0.18 g of the compound according to Example 191c was dissolved in 30 ml of dry methanol at RT, treated with Pd/C catalyst under argon, and hydrogenated at RT for 4 h. After filtration, washing of the residue with methanol and concentration of the filtrate, N-[5-(1-amino-3-phenylpropyl)-[1,3,4]oxadiazol-2-yl]benzenesulfonamide was obtained, which was employed in the next stage.

e) Preparation of 2-pyridin-4-yl-1H-benzimidazole-4-carboxylic acid [1-(5-benzenesulfonylamino-[1,3,4]oxadiazol-2-yl)-3-phenylpropyl]amide:

70 mg of the compound according to Example 191d were dissolved in 5 ml of dry DMF at RT, and treated with 30 µl of diisopropylamine, 48 mg of 2-pyridin-4-yl-1H-benzimidazole-5-carboxylic acid, and 66 mg of TOTU. After stirring at RT for 4 h, the reaction was complete and the reaction mixture was concentrated. The residue was treated with ethyl acetate and water. The solvents were decanted; the oily residue was treated with warm acetone, the mixture was cooled, and the crystalline product was collected on a filter, washed with acetone, and dried. 2-Pyridin-4-yl-1H-benzimidazole-4-carboxylic acid [1-(5-benzenesulfonylamino-[1,3,4]oxadiazol-2-yl)-3-phenylpropyl]amide, which melted at 220° C. with decomposition, is obtained.

EXAMPLE 192

The following compound was prepared according to process variant a) as in the general working procedure:

a) Preparation of Z-homophenylalanine hydrazide:

Z-Homophenylalanine hydrazide was prepared as described in Example 179a.

b) Preparation of benzyl [1-(5-amino-[1,3,4]oxadiazol-2-yl)-3-phenylpropyl]carbamate:

Benzyl [1-(5-amino-[1,3,4]oxadiazol-2-yl)-3-phenylpropyl]carbamate was prepared as described in Example 179b.

c) Preparation of benzyl {1-[5-(3-methylureido)-[1,3,4]oxadiazol-2-yl]-3-phenylpropyl}carbamate:

350 mg of benzyl [1-(5-amino-[1,3,4]oxadiazol-2-yl)-3-phenylpropyl]-carbamate were dissolved in 5 ml of dry dimethyl sulfoxide, treated with 140 mg of potassium carbonate and 140 mg of methyl isocyanate, and stirred at 80° C. for 16 h. The reaction mixture was cooled, treated with ethyl acetate, washed twice with water and once with saturated sodium chloride solution, dried over magnesium sulfate, filtered, and concentrated in vacuo. Benzyl {1-[5-(3-methylureido)-[1,3,4]oxadiazol-2-yl]-3-phenylpropyl}carbamate was obtained, which was employed in the next stage (hydrogenolysis) without further purification.

d) Preparation of 1-[5-(1-amino-3-phenylpropyl)-[1,3,4]oxadiazol-2-yl]-3-methylurea:

120 mg of the previous compound were dissolved in 20 ml of dry methanol at RT, treated with Pd/C catalyst under argon, and hydrogenated at RT for 4 h. The reaction mixture was filtered, the residue was washed with methanol, and the filtrate was concentrated in vacuo. The 1-[5-(1-amino-3-phenylpropyl)-[1,3,4]oxadiazol-2-yl]-3-methylurea was employed in the next stage without further purification.

e) Preparation of 2-pyridin-4-yl-1H-benzimidazole-5-carboxylic acid {1-[5-(3-methylureido)-[1,3,4]oxadiazol-2-yl]-3-phenylpropyl}amide:

40 mg of the previous compound was dissolved in 3 ml of dry DMF at RT and treated successively with 33 mg of 2-pyridin-4-yl-1H-benzimidazole-5-carboxylic acid, 20 µl of diisopropylamine, and 40 mg of TOTU and stirred at RT for 4 h. The reaction mixture was concentrated in vacuo; the residue was taken up in ethyl acetate/tetrahydrofuran (1/1), washed with water, saturated sodium hydrogencarbonate solution, and saturated sodium chloride solution, dried over magnesium sulfate, filtered, and concentrated in vacuo. 2-Pyridin-4-yl-1H-benzimidazole-5-carboxylic acid {1-[5-(3-methylureido)-[1,3,4]oxadiazol-2-yl]-3-phenylpropyl}amide was obtained, which has m/e=497.3 (=MH$^+$) in the mass spectrum.

EXAMPLE 193

The following compound was prepared according to process variant a) as in the general working procedure:

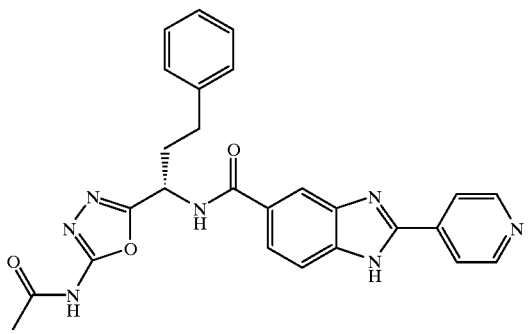

2-Pyridin-4-yl-1H-benzimidazole-5-carboxylic acid [1-(5-acetylamino-[1,3,4]oxadiazol-2-yl)-3-phenylpropyl] amide was prepared in a principally analogous manner, but with the difference that it was reacted with acetyl chloride instead of with methyl isocyanate. The compound has a melting point of 183°–186° C. with decomposition.

EXAMPLE 194

The following compound was prepared according to process variant a) as in the general working procedure:

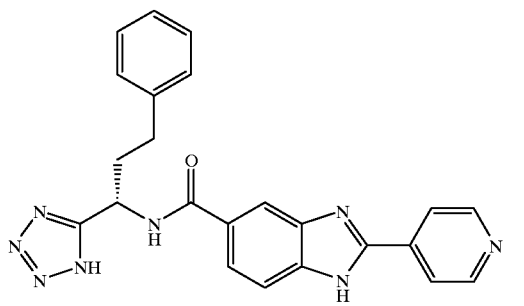

a) Preparation of benzyl (1-cyano-3-phenylpropyl) carbamate:

2.78 g of benzyl (1-carbamoyl-3-phenylpropyl) carbamate, prepared from L-homophenylalanine amide hydrochloride and N-Cbz-succinimide, were dissolved in 30 ml of dry pyridine and treated with 6 ml of acetic anhydride. The reaction mixture was stirred at 75° C. for 24 h. The cooled solution was concentrated in vacuo, treated with 100 ml of ethyl acetate, and then extracted three times by shaking with 50 ml each of 5% strength citric acid solution and saturated sodium chloride solution. The organic extract was dried over magnesium sulfate, filtered, concentrated in vacuo, and chromatographed on silica gel using n-heptane/ethyl acetate (1/1). Benzyl (1-cyano-3-phenylpropyl) carbamate was obtained, which was employed in the next stage without further purification.

b) Preparation of benzyl [3-phenyl-1-(1H-tetrazol-5-yl) propyl]carbamate:

0.15 g of the compound of Example 194a was suspended in 5 ml of dry toluene with 0.115 g of trimethyltin azide and stirred under reflux for 6 h. The cooled reaction mixture was acidified with ethereal hydrochloric acid and allowed to stand overnight in a refrigerator. On the next day, the mixture was concentrated in vacuo and chromatographed on silica gel using dichloromethane/methanol (9/1). The benzyl [3-phenyl-1-(1H-tetrazol-5-yl)propyl]carbamate thus obtained was employed in the next stage without further purification.

c) Preparation of 3-phenyl-1-(1H-tetrazol-5-yl) propylamine:

337 mg of the compound of Example 194b were dissolved in 2 ml of acetonitrile, treated with 0.477 ml of triethylsilane, one drop of triethylamine, and a spatula tipful of palladium(II) chloride, and stirred under reflux for 3 h. The cooled solution was filtered, concentrated in vacuo, and the residue was dried under high vacuum. The 3-phenyl-1-(1H-tetrazol-5-yl)propylamine thus obtained was reacted further.

d) Preparation of 2-pyridin-4-yl-1H-benzimidazole-5-carboxylic acid [3-phenyl-1-(1H-tetrazol-5-yl)propyl] amide:

0.9 mmol of the compound of Example 194c was dissolved in 5 ml of dry DMF and treated with 0.9 mmol of 2-pyridin-4-yl-1H-benzimidazole-5-carboxylic acid, 0.365 ml of diisopropylamine, and 415 mg of TOTU, and stirred at RT for 20 h and at 50° C. for a further 4 h. The reaction mixture was concentrated in vacuo; the residue was taken up in ethyl acetate, washed with water, saturated sodium hydrogencarbonate solution, and saturated sodium chloride solution, dried over magnesium sulfate, filtered, and concentrated in vacuo. The crude product thus obtained was chromatographed on silica gel using dichloromethane/methanol/water/glacial acetic acid (60/10/1/1). 2-Pyridin-4-yl-1H-benzimidazole-5-carboxylic acid [3-phenyl-1-(1H-tetrazol-5-yl)propyl]amide, was obtained, which decomposed at 87° C. and had a molecular peak at m/e= 425.2 (=MH$^+$), is obtained.

EXAMPLE 195

3-Phenylaminoethyl-2-[(2-pyridin-4-yl-1H-benzimidazole-5-carbonyl)-amino]propionic acid trifluoroacetate

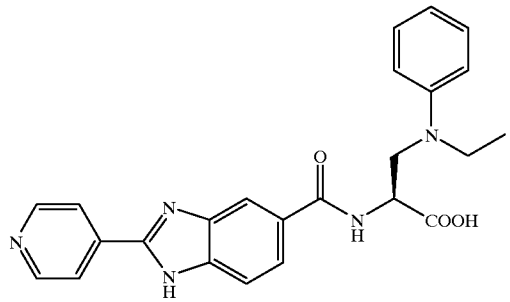

a) L-2-Amino-3-phenylaminoethylpropionic acid:

54.8 g (0.209 mol) of triphenylphosphine were suspended in 600 ml of acetonitrile and cooled to −35° C. to −45° C. with exclusion of moisture and 36.4 g (0.209 mol) of diethyl azodicarboxylic acid were then added dropwise at this temperature in the course of 50 min. The mixture was stirred at −35° C. for 15 min. A solution of 50 g (0.209 mol) of N-benzyloxycarbonyl-L-serine in 500 ml of acetonitrile was added dropwise to this mixture, and in the course of this the temperature was not allowed to rise above −35° C. The mixture was then allowed to react at −35° C. for 12 h and warmed to RT. The reaction solution was freed from the solvent under reduced pressure and the crude product was immediately purified using medium-pressure chromatography on silica gel (DCM/AcCN=25/1). After removal of the solvent, 20.8 g (yield 45%) of clean N-benzoyloxycarbonyl-L-serine-β-lactone were obtained (see also *Org. Synth.* 70

(1991) 1ff) in fine needles. Empirical formula $C_{11}H_{11}NO_4$; molecular weight of 221.2; MS (M+H) is 222.1.

7.3 ml (57.36 mmol) of N-ethylaniline dissolved in 250 ml of acetonitrile were added under argon to 15.5 ml (63.51 mmol) of N,O-bis-(trimethylsilyl)-acetamide and stirred for 3 h at 50° C. 10.7 g (48.37 mmol) of said lactone were dissolved in 250 ml of acetonitrile at 20° C. and heated under reflux for 17 h. After removal of the solvent, saturated $Na_2CO_3$ solution was added to the residue, wherein the pH of the solution did not exceed 9. The received aqueous suspension was washed with some diethylether and concentrated hydrochloric acid was added to adjust to a pH from 6 to 7. The pH of the solution was then adjusted to 5 by addition of $NaHPO_4$ buffer. The aqueous solution was extracted several times with acetic ester. After removal of the solvent, 7.4 g (yield 45%) of the product were obtained. Empirical formula $C_{19}H_{22}N_2O_4$; molecular weight of 342.4; MS (M+H) is 343.2.

6.5 ml (89.1 mmol) of thionylchloride were added dropwise to 75 ml of methanol at −10° C. and stirred for 30 min. A solution of 8.6 g (25.12 mmol) of L-2-aminoethyl-3-phenylamino-propionic acid dissolved in 75 ml of methanol were added and stirred for 30 min at −10° C. and then stirred for 3 h at RT. After removal of the solvent, acetic ester was added to the residue and washed with sodium hydrogencarbonate solution. After removal of the solvent, 4.43 g (yield 50%) of the methyl L-2-aminoethyl-3-phenylamino-propionate were isolated by flash chromatography (n-heptane/acetic ester=7/3). Empirical formula $C_{20}H_{24}N_2O_4$; molecular weight of 356.4; MS (M+H) is 357.3.

To remove the protective group, 4.4 g (12.35 mmol) of the Z-protected derivative was dissolved in 500 ml of methanol, 80 mg of catalyst (10% $Pd(OH)_2$—C) were added under inert gas, and hydrogen was passed in until the Z-protective group was completely removed. After filtering off the catalyst and evaporating the filtrate, 2.8 g of L-2-aminoethyl-3-phenylamino-propionic acid (92%) were obtained. Empirical formula $C_{12}H_{18}N_2O_2$; molecular weight of 222.3; MS (M+H) is 223.1.

Process step b):

2.4 g (10.03 mmol) of 2-pyridin-4-yl-1H-benzimidazole-5-carboxylic acid prepared as in Example 182 were suspended in 350 ml of DMF and treated successively with 4.2 g (12.80 mmol) of TOTU and 2.3 ml (13.52 mmol) of ethyldiisopropylamine. The mixture was stirred at RT for 10 min and 2.8 g (12.60 mmol) of methyl (S)-2-amino-3-phenyl-aminoethyl-propionate prepared according to a) were added to the resulting clear solution. After stirring for 2 h, the mixture was concentrated under reduced pressure and the methyl ester was isolated by flash chromatography on silica gel (DCM/MeOH=9/1). Yield 4.36 g (98%); empirical formula $C_{25}H_{25}N_5O_3$; molecular weight of 443.5; MS (M+H) is 444.3.

4.3 g of the obtained methyl ester dissolved in 400 ml of methanol were hydrolyzed by the addition of 200 ml 1 M sodium hydroxide at RT for 2 h. After evaporating methanol, $NaH_2PO_4$-buffer was added to the residue until a pH-value of 5 was reached. During this process the title compound was precipitated. The received product was isolated by flash chromatography on silica gel (DCM/MeOH=4/1) and by preparative high pressure liquid chromatography (acetonitrile/0.1% trifluoroacetic acid). Thus, 2.92 g (yield 70%) of 3-phenylaminoethyl-2-[(2-pyridin-4-yl-1H-benzimidazole-5-carbonyl)-amino]propionic acid trifluoroacetate were obtained. Empirical formula $C_{24}H_{23}N_5O_3$; molecular weight of 429.5; MS (M+H) is 430.3; melting point is about 258° C. (under decomposition).

Pharmacological examples

IκB kinase filter test:

The activity of the IκB kinase was determined using the "SIGMATECT® Protein Kinase Assay System" (Promega catalog 1998, p. 330; analogous to the SIGMATECT® DNA-dependent protein kinase procedure). The kinase was purified from HeLa cell extracts according to Z. J. Chen, Cell 84 (1996) 853–862, and incubated with the substrate peptide (biotin-$(CH_2)_8$-DRHDSGLDSMKD-$CONH_2$) (20 µM). The reaction buffer contained 50 mM HEPES, pH 7.5, 10 mM $MgCl_2$, 5 mM dithiothreitol (DTT), 10 mM β-glycerophosphate, 10 mM 4-nitrophenyl phosphate, 1 µM microcystine-LR, and 50 µM ATP (comprising 1 µCi of γ-$^{33}$P-ATP).

Method PKA, PKC, CK II:

cAMP-dependent protein kinase (PKA), protein kinase C (PKC), and casein kinase II (CK II) were determined using the appropriate test kits of Upstate Biotechnology according to the procedure of the manufacturer at an ATP concentration of 50 µM. Differently, no phosphocellulose filter, but MultiScreen plates (Millipore; phosphocellulose MS-PH, cat. MAPHNOB10) with the corresponding aspiration system were used. The plates or membranes (IκB kinase) were then measured in a Wallac Microβeta scintillation counter. 100 µM of the test substance were employed in each case.

Each substance was tested in a duplicate determination. The mean value of the blank (without enzyme) is subtracted from the mean values (enzyme with and without substances) and the % inhibition is calculated. $IC_{50}$ calculations were carried out using the software package GraFit 3.0. Table 6 which follows shows the results.

TABLE 6

Kinase inhibition at a substance concentration of 100 µM or $IC_{50}$ in µM

| Example number | IκB kinase $IC_{50}$ | PKA % inhibition | PKC % inhibition | CK II % inhibition |
|---|---|---|---|---|
| 5 | 25 | 0 | 16 | 19 |
| 6 | 72 | 0 | 46 | 14 |
| 7 | 22 | 0 | 15 | 10 |
| 8 | 4 | 0 | 9 | 7 |
| 11 | 7 | 0 | 16 | 0 |
| 12 | 42 | 0 | 16 | 0 |
| 14 | 7 | 0 | 0 | 0 |
| 16 | 9 | 0 | 11 | 4 |
| 19 | 1 | 36 | 63 | 70 |
| 20 | 34 | 26 | 31 | 60 |
| 34 | 16 | n.d. | n.d. | n.d. |
| 36 | 36 | n.d. | n.d. | n.d. |
| 107 | 1 | 0 | 13 | 92 |
| 112 | 25 | 24 | 7 | 17 |
| 179 | 0.43 | n.d. | n.d. | n.d. |
| 180 | 0.62 | n.d. | n.d. | n.d. |
| 191 | 0.12 | n.d. | n.d. | n.d. |
| 192 | 0.36 | n.d. | n.d. | n.d. |
| 195 | 0.07 | 31 | 40 | 50 | n.d. means not determined

The present invention may be embodied in other specific forms without departing from its spirit or essential characteristics. The described embodiments are to be considered in all respects as illustrative only and not restrictive. The scope of the invention is, therefore, indicated by the appended claims rather than by the foregoing description. All changes which come within the meaning and range of equivalency of the claims are to be embraced within their scope.

What is claimed is:
1. A compound of formula I

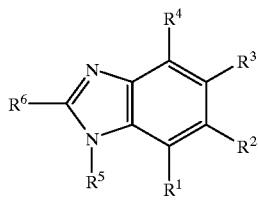

or a stereoisomeric form of the compound of formula I or a physiologically tolerable salt of the compound of formula I, where one of the substituents $R^1$, $R^2$, $R^3$, and $R^4$ is a radical of formula II

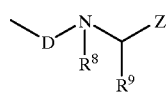

in which:
D is —C(O)—, —S(O)—, or —S(O)$_2$—;
$R^8$ is hydrogen or ($C_1$–$C_4$)-alkyl;
$R^9$ is
(1) alanine, valine, leucine, isoleucine, phenylalanine, tyrosine, tryptophan, serine, threonine, cysteine, methionine, asparagine, glutamine, lysine, histidine, arginine, glutamic acid, or aspartic acid;
(2) 2-aminoadipic acid, 2-aminobutyric acid, 2-aminoisobutyric acid, 2,3-diaminopropionic acid, 2,4-diaminobutyric acid, 1,2,3,4-tetrahydroisoquinoline-1-carboxylic acid, 1,2,3,4-tetrahydroisoquinoline-3-carboxylic acid, 2-aminopimelic acid, 2-amino-3-phenylaminoethyl-propionic acid, 2-amino-3-phenylamino-propionic acid, 3-(2-thienyl)alanine, 3-(3-thienyl)alanine, 2-aminoheptanoic acid, pipecolic acid, hydroxylysine, sarcosine, N-methylisoleucine, 6-N-methyllysine, N-methylvaline, norvaline, norleucine, ornithine, allo-isoleucine, allo-threonine, allo-hydroxylysine, 4-hydroxyproline, 3-hydroxyproline, 3-(2-naphthyl) alanine, 3-(1-naphthylalanine), homophenylalanine, homocysteine, homocysteic acid, homotryptophan, cysteic acid, 3-(2-pyridyl)alanine, 3-(3-pyridyl) alanine, 3-(4-pyridyl)alanine, phosphinothricin, 4-fluorophenylalanine, 3-fluorophenylalanine, 2-fluorophenylalanine, 4-chlorophenylalanine, 4-nitrophenylalanine, 4-aminophenylalanine, cyclohexylalanine, citrulline, 5-fluorotryptophan, 5-methoxytryptophan, methionine sulfone, methionine sulfoxide, or —NH—NR$^{11}$—CON(R$^{11}$)$_2$, wherein R$^{11}$ is as defined below:
(3) aryl, in which aryl is unsubstituted or substituted, selected from naphthyl, biphenylyl, anthryl, and fluorenyl;
(4) heteroaryl having 5 to 14 ring members, in which the heteroaryl is unsubstituted or substituted, selected from pyrrole, imidazole, pyrazole, oxazole, isoxazole, thiazole, isothiazole, tetrazole, 1,3,4-oxadiazole, 1,2,3, 5-oxathiadiazole-2-oxides, triazolones, oxadiazolones, isoxazolones, oxadiazolidinediones, triazoles which are substituted by F, CN, CF$_3$, or COO—(C$_1$–C$_4$)-alkyl, 3-hydroxypyrrole-2,4-diones, 5-oxo-1,2,4-thiadiazoles, pyrazine, pyrimidine, indole, isoindole, indazole, phthalazine, quinoline, isoquinoline, quinoxaline, quinazoline, cinnoline, carboline, and benzo-fused, cyclopenta-, cyclohexa-, or cyclohepta-fused derivatives of these heteroaryls;
(5) (C$_1$–C$_6$)-alkyl, in which alkyl is unsubstituted or mono-, di-, or trisubstituted independently of one another by
(5)(1) aryl, in which aryl is unsubstituted or substituted;
(5)(2) heteroaryl having 5 to 14 ring members, in which the heteroaryl is unsubstituted or substituted;
(5)(3) a heterocycle having 5 to 12 ring members, in which the heterocycle is unsubstituted or substituted;
(5)(4) —O—R$^{11}$;
(5)(5) =O;
(5)(6) halogen;
(5)(7) —CN;
(5)(8) —CF$_3$;
(5)(9) —S(O)$_x$—R$^{11}$, in which x is the integer 0, 1, or 2;
(5)(10) —C(O)—O—R$^{11}$;
(5)(11) —C(O)—N(R$^{11}$)$_2$;
(5)(12) —N(R$^{11}$)$_2$;
(5)(13) (C$_3$–C$_6$)-cycloalkyl;
(5)(14) a radical of formula

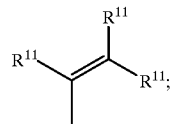

or
(5)(15) a radical of formula

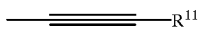

in which
R$^{11}$ is
(a) hydrogen;
(b) (C$_1$–C$_6$)-alkyl, in which alkyl is unsubstituted or mono-, di-, or trisubstituted independently of one another by
(1) aryl, in which aryl is unsubstituted or substituted;
(2) heteroaryl having 5 to 14 ring members, in which the heteroaryl is unsubstituted or substituted;
(3) a heterocycle having 5 to 12 ring members, in which the heterocycle is unsubstituted or substituted;
(4) halogen;
(5) —N—(C$_1$–C$_6$)$_n$-alkyl, in which n is the integer 0, 1, or 2, and alkyl is unsubstituted or mono-, di-, or trisubstituted independently of one another by halogen or by —COOH;
(6) —O—(C$_1$–C$_6$)-alkyl; or
(7) —COOH;
(c) aryl, in which aryl is unsubstituted or substituted;
(d) heteroaryl having 5 to 14 ring members, in which the heteroaryl is unsubstituted or substituted; or
(e) a heterocycle having 5 to 12 ring members, in which the heterocycle is unsubstituted or substituted; and in the case of $(R^{11})_2$, $R^{11}$ independently of one another has the meaning of (a) to (e);

Z is
  (1) aryl, in which aryl is unsubstituted or substituted;
  (2) heteroarl having 5 to 14 ring members, in which the heteroaryl is unsubstituted or substituted;
  (3) a heterocycle having 5 to 12 ring members, in which the heterocycle is unsubstituted or substituted;
  (4) —$(C_1-C_6)$-alkyl, in which alkyl is mono- or disubstituted independently of one another by
    (4)(1) aryl, in which aryl is unsubstituted or substituted;
    (4)(2) heteroaryl having 5 to 14 ring members, in which the heteroaryl is unsubstituted or substituted;
    (4)(3) a heterocycle having 5 to 12 ring members, in which the heterocycle is unsubstituted or substituted;
    (4)(4) halogen;
    (4)(5) —N—$(C_1-C_6)_n$-alkyl, in which n is the integer 0, 1, or 2, and alkyl is unsubstituted or mono- , di-, or trisubstituted independently of one another by halogen or by —COOH;
    (4)(6) —O—$(C_1-C_6)$-alkyl; or
    (4)(7) —COOH; or
  (5) —C(O)—$R^{10}$, in which
    $R^{10}$ is
      (1) —O—$R^{11}$; or
      (2) —N$(R^{11})_2$;
      in which $R^{11}$ is as defined above; or
$R^8$ and $R^9$, together with the nitrogen and carbon to which they are each bonded, form a heterocyclic ring of formula IIa

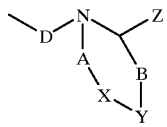

IIa in which:
D, Z, and $R^{10}$ are as defined in formula II;
A is nitrogen or —CH$_2$—;
B is oxygen, sulfur, nitrogen, or —CH$_2$;
X is oxygen, sulfur, nitrogen, or —CH$_2$;
Y is absent or is oxygen, sulfur, nitrogen, or —CH$_2$—; or
X and Y together form a phenyl, 1,2-diazine, 1,3-diazine, or a 1,4-diazine radical;
  where the ring system formed by N, A, X, Y, B, and the carbon contains no more than one oxygen, X is not oxygen, sulfur, or nitrogen if A is a nitrogen atom; contains no more than one sulfur; contains 1, 2, 3, or 4 nitrogens; and where oxygen and sulfur do not occur at the same time;
  where the ring system formed by N, A, X, Y, B, and the carbon is unsubstituted or mono-, di-, or trisubstituted independently of one another by $(C_1-C_8)$-alkyl, in which alkyl is straight-chain or branched and is unsubstituted or mono- or disubstituted by
    (1)(1) —OH;
    (1)(2) $(C_1-C_8)$-alkoxy, in which alkoxy is straight-chain or branched;
    (1)(3) halogen;
    (1)(4) —NO$_2$;
    (1)(5) —NH$_2$;
    (1)(6) —CF$_3$;
    (1)(7) —OH;
    (1)(8) methylenedioxy;
    (1)(9) —C(O)—CH$_3$;
    (1)(10) —CH(O);
    (1)(11) —CN;
    (1)(12) —COOH;
    (1)(13) —C(O)—NH$_2$;
    (1)(14) $(C_1-C_4)$-alkoxycarbonyl, in which alkoxycarbonyl is straight-chain or branched;
    (1)(15) phenyl;
    (1)(16) phenoxy;
    (1)(17) benzyl;
    (1)(18) benzyloxy; or
    (1)(19) tetrazolyl; or
$R^9$ and Z together with the carbons to which they each are bonded form a heterocyclic ring of formula IIc

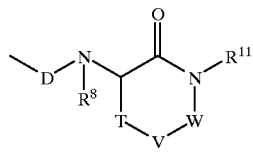

IIc in which:
D, $R^8$, and $R^{11}$ are as defined in formula II;
T is oxygen, sulfur, nitrogen, or —CH$_2$—;
W is oxygen, sulfur, nitrogen, or —CH$_2$—;
V is absent or is oxygen, sulfur, nitrogen, or —CH$_2$—; or
T and V together form a phenyl, 1,2-diazine, 1,3-diazine, or a 1,4-diazine radical; or
V and W together form a phenyl, 1,2-diazine, 1,3-diazine, or a 1,4-diazine radical;
  where the ring system formed by N, T, V, W, and the two carbons contains no more than one oxygen, no more than one sulfur, and 1, 2, 3, or 4 nitrogens; where oxygen and sulfur do not occur at the same time; and where the ring system formed by N, T, V, W, and the two carbons is unsubstituted or mono-, di-, or trisubstituted independently of one another by the substituents defined above under (1)(1) to (1)(19); and
the other substituents $R^1$, $R^2$, $R^3$, and $R^4$ are chosen independently of one another, and are
  (1) hydrogen;
  (2) halogen;
  (3) $(C_1-C_4)$-alkyl;
  (4) heteroaryl having 5 to 14 ring members, in which the heteroaryl is unsubstitued or substituted;
  (5) a heterocycle having 5 to 12 ring members, in which the heterocycle is unsubstituted or substituted; or
  (6) $(C_1-C_6)$-alkyl;
  (7) —CN;
  (8) —NO$_2$;
  (9) —O—$(C_0-C_4)$-alkyl-aryl, in which alkyl is straight-chain or branched;
  (10) —O—$(C_1-C_4)$-alkyl;
  (11) —OR$^{11}$;
  (12) —N$(R^{11})_2$;
  (13) —S(O)$_x$R$^{11}$, in which x is the integer 0, 1, or 2; or
  (14) —CF$_3$;
  in which $R^{11}$ is as defined above;

$R^5$ is
(1) hydrogen;
(2) —OH; or
(3) =O; and $R^6$ is
(1) aryl, in which aryl is unsubstituted or substituted, and is selected from phenyl, naphthyl, biphenylyl, anthryl, and fluorenyl, in which aryl is unsubstituted, monosubstituted, or polysubstituted independently of one another by $(C_1-C_8)$-alkyl, $(C_1-C_8)$-alkoxy, halogen, nitro, amino, trifluoromethyl, hydroxyl, hydroxy-$(C_1-C_4)$-alkyl, methylenedioxy, ethylenedioxy, formyl, acetyl, cyano, hydroxytarbonyl, aminocarbonyl, $(C_1-C_4)$-alkoxycarbonyl, phenyl, phenoxy, benzyl, benzyloxy, and tetrazolyl; or
(2) heteroaryl having 5 to 14 ring members, in which the heteroaryl is unsubstituted or substituted and is selected from pyrrole, furan, thiophene, imidazole, pyrazole, oxazole, isoxazole, thiazole, isothiazole, tetrazole, 1,3,4 oxadiazole, 1,2,3,5-oxathiadiazole-2-oxides, triazolones, oxadiazolones, isoxazolones, oxadiazolidinediones, triazoles which are substituted by F, CN, $CF_3$, or COO—$(C_1-C_4)$-alkyl, 3-hydroxypyrrole-2,4-diones, 5-oxo-1,2,4-thiadiazoles, pyridine, pyrazine, pyrimidine, indole, isoindole, indazole, phthalazine, quinoitne, isoquinoline, quinoxaline, quinazoline, cinnoline, carboline, and benzo-fused, cyclopenta-, cyclohexa-, or cyclohepta-fused derivatives of these heteroaryls.

2. A compound of formula I

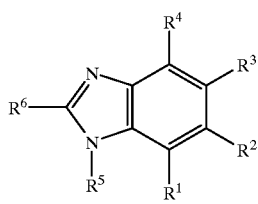

or a stereoisomeric form of the compound of formula I or a physiologically tolerable salt of the compound of formula I, where one of the substituents $R^1$, $R^2$, $R^3$, and $R^4$ is a radical of formula II

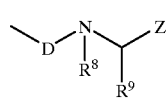

in which:
D is —C(O)—, —S(O)—, or —S(O)$_2$—;
$R^8$ is hydrogen or $(C_1-C_4)$-alkyl;
$R^9$ is
(1) alanine, valine, leucine, isoleucine, phenylalanine, tyrosine, tryptophan, serine, threonine, cysteine, methionine, asparagine, glutamine, lysine, histidine, arginine, glutamic acid, or aspartic acid;
(2) 2-aminoadipic acid, 2-aminobutyric acid, 2-aminoisobutyric acid, 2,3-diaminopropionic acid, 2,4-diaminobutyric acid, 1,2,3,4-tetrahydroisoquinoline-1-carboxylic acid, 1,2,3,4-tetrahydroisoquinoline-3-carboxylic acid, 2-aminopimelic acid, 2-amino-3-phenylaminoethyl-propionic acid, 2-amino-3-phenylamino-propionic acid, 3-(2-thienyl)alanine, 3-(3-thienyl)alanine, 2-aminoheptanoic acid, pipecolic acid, hydroxylysine, sarcosine, N-methylisoleucine, 6-N-methyllysine, N-methylvaline, norvaline, norleucine, ornithine, allo-isoleucine, allo-threonine, allo-hydroxylysine, 4-hydroxyproline, 3-hydroxyproline, 3-(2-naphthyl) alanine, 3-(1-naphthylalanine), homophenylalanine, homocysteine, homacysteic acid, homotryptophan, cysteic acid, 3-(2-pyridyl)alanine, 3-(3-pyridyl) alanine, 3-(4-pyridyl)alanine, phosphinothricin, 4-fluorophenylalanine, 3-fluorophenylalanine, 2-fluorophenylalanine, 4-chlorophenylalanine, 4-nitrophenylalanine, 4-aminophenylalanine, cyclohexylalanine, citrulline, 5-fluorotryptophan, 5-methoxytryptophan, methionine sulfone, methionine sulfoxide, or —NH—NR$^{11}$—CON(R$^{11}$)$_2$, wherein $R^{11}$ is as defined below;
(3) aryl, in which aryl is unsubstituted or substituted, selected from naphthyl, biphenylyl, anthryl, and fluorenyl;
(4) heteroaryl having 5 to 14 ring members, in which the heteroaryl is unsubstituted or substituted, selected from pyrrole, imidazole, pyrazole, oxazole, isoxazole, thiazole, isothiazole, tetrazole, 1,3,4-oxadiazole, 1,2,3, 5-oxathiadiazole-2-oxides, triazolones, oxadiazolones, isoxazolones, oxadiazolidinediones, triazoles which are substituted by F, CN, CF$_3$, or COO—(C$_1$–C$_4$)-alkyl, 3-hydroxypyrrole-2,4-diones, 5-oxo-1,2,4-thiadiazoles, pyrazine, pyrimidine, indole, isoindole, indazole, phthalazine, quinoline, isoquinoline, quinoxaline, quinazoline, cinnoline, carboline, and benzo-fused, cyclopenta-, cyclohexa-, or cyclohepta-fused derivatives of these heteroaryls;
(5) (C$_1$–C$_6$)-alkyl, in which alkyl is unsubstituted or mono-, di-, or trisubstituted independently of one another by
(5)(1) aryl, in which aryl is unsubstituted or substituted;
(5)(2) heteroaryl having 5 to 14 ring members, in which the heteroaryl is unsubstituted or substituted;
(5)(3) a heterocycle having 5 to 12 ring members, in which the heterocycle is unsubstituted or substituted;
(5)(4) —O—R$^{11}$;
(5)(5) =O;
(5)(6) halogen;
(5)(7) —CN;
(5)(8) —CF$_3$;
(5)(9) —S(O)$_x$—R$^{11}$, in which x is the integer 0, 1, or 2;
(5)(10) —C(O)—O—R$^{11}$;
(5)(11) —C(O)—N(R$^{11}$)$_2$;
(5)(12) —N(R$^{11}$)$_2$;
(5)(13) (C$_3$–C$_6$)-cycloalkyl;
(5)(14) a radical of formula

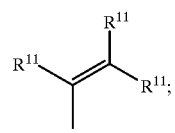

or (5)(15) a radical of formula

in which
R$^{11}$ is
- (a) hydrogen;
- (b) (C$_1$–C$_6$)-alkyl, in which alkyl is unsubstituted or mono-, di-, or trisubstituted independently of one another by
  - (1) aryl, in which aryl is unsubstituted or substituted;
  - (2) heteroaryl having 5 to 14 ring members, in which the heteroaryl is unsubstituted or substituted;
  - (3) a heterocycle having 5 to 12 ring members, in which the heterocycle is unsubstituted or substituted;
  - (4) halogen;
  - (5) —N—(C$_1$–C$_6$)$_n$-alkyl, in which n is the integer 0, 1, or 2, and alkyl is unsubstituted or mono-, di-, or trisubstituted independently of one another by halogen or by —COOH;
  - (6) —O—(C$_1$–C$_6$)-alkyl; or
  - (7) —COOH;
- (c) aryl, in which aryl is unsubstituted or substituted;
- (d) heteroaryl having 5 to 14 ring members, in which the heteroaryl is unsubstituted or substituted; or
- (e) a heterocycle having 5 to 12 ring members, in which the heterocycle is unsubstituted or substituted; and
  in the case of (R$^{11}$)$_2$, R$^{11}$ independently of one another has the meaning of (a) to (e);

Z is
(1) aryl, in which aryl is unsubstituted or substituted;
(2) heteroaryl having 5 to 14 ring members, in which the heteroaryl is unsubstituted or substituted;
(3) a heterocycle having 5 to 12 ring members, in which the heterocycle is unsubstituted or substituted;
(4) —(C$_1$–C$_6$)-alkyl, in which alkyl is mono- or disubstituted independently of one another by
  (4)(1) aryl, in which aryl is unsubstituted or substituted;
  (4)(2) heteroaryl having 5 to 14 ring members, in which the heteroaryl is unsubstituted or substituted;
  (4)(3) a heterocycle having 5 to 12 ring members, in which the heterocycle is unsubstituted or substituted;
  (4)(4) halogen;
  (4)(5) —N—(C$_1$–C$_6$)$_n$-alkyl, in which n is the integer 0, 1, or 2, and alkyl is unsubstituted or mono-, di-, or trisubstituted independently of one another by halogen or by —COOH;
  (4)(6) —O—(C$_1$–C$_6$)-alkyl; or
  (4)(7) —COOH; or
(5) —C(O)—R$^{10}$, in which
  R$^{10}$ is
  (1) —O—R$^{11}$; or
  (2) —N(R$^{11}$)$_2$;
    in which R$^{11}$ is as defined above; or
R$^8$ and R$^9$, together with the nitrogen and carbon to which they are each bonded, form a heterocyclic ring of formula IIa

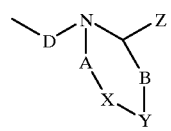

in which:
D, Z, and R$^{10}$ are as defined in formula II;
A is nitrogen or —CH$_2$—;
B is oxygen, sulfur, nitrogen, or —CH$_2$;
X is oxygen, sulfur, nitrogen, or —CH$_2$;
Y is absent or is oxygen, sulfur, nitrogen, or —CH$_2$—; or
X and Y together form a phenyl, 1,2-diazine, 1,3-diazine, or a 1,4-diazine radical;
  where the ring system formed by N, A, X, Y, B, and the carbon contains no more than one oxygen, X is not oxygen, sulfur, or nitrogen if A is a nitrogen atom; contains no more than one sulfur; contains 1, 2, 3, or 4 nitrogens; and where oxygen and sulfur do not occur at the same time;
  where the ring system formed by N, A, X, Y, B, and the carbon is unsubstituted or mono-, di-, or trisubstituted independently of one another by (C$_1$–C$_8$)-alkyl, in which alkyl is straight-chain or branched and is unsubstituted or mono- or disubstituted by
    (1)(1) —OH;
    (1)(2) (C$_1$–C$_8$)-alkoxy, in which alkoxy is straight-chain or branched;
    (1)(3) halogen;
    (1)(4) —NO$_2$;
    (1)(5) —NH$_2$;
    (1)(6) —CF$_3$;
    (1)(7) —OH;
    (1)(8) methylenedioxy;
    (1)(9) —C(O)—CH$_3$;
    (1)(10) —CH(O);
    (1)(11) —CN;
    (1)(12) —COOH;
    (1)(13) —C(O)—NH$_2$;
    (1)(14) (C$_1$–C$_4$)-alkoxycarbonyl, in which alkoxycarbonyl is straight-chain or branched;
    (1)(15) phenyl;
    (1)(16) phenoxy;
    (1)(17) benzyl;
    (1)(18) benzyloxy; or
    (1)(19) tetrazolyl; or
R$^9$ and Z together with the carbons to which they each are bonded form a heterocyclic ring of formula IIc

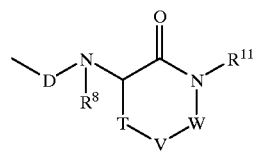

in which:
D, R$^8$, and R$^{11}$ are as defined in formula II;
T is oxygen, sulfur, nitrogen, or —CH$_2$—;
W is oxygen, sulfur, nitrogen, or —CH$_2$—;
V is absent or is oxygen, sulfur, nitrogen, or —CH$_2$—; or
T and V together form a phenyl, 1,2-diazine, 1,3-diazine, or a 1,4-diazine radical; or V and W together form a phenyl, 1,2-diazine, 1,3-diazine, or a 1,4-diazine radical;
  where the ring system formed by N, T, V, W, and the two carbons contains no more than one oxygen, no more than one sulfur, and 1, 2, 3, or 4 nitrogens; where oxygen and sulfur do not occur at the same time; and where the ring system formed by N, T, V, W, and the two carbons is unsubstituted or mono-, di-, or trisubstituted independently of one another by the substituents defined above under (1)(1) to (1)(19); and
  the other substituents $R^1$, $R^2$, $R^3$, and $R^4$ are chosen independently of one another, and are
    (1) hydrogen;
    (4) halogen;
    (5) ($C_1$–$C_4$-alkyl;
    (4) heteroaryl having 5 to 14 ring members, in which the heteroaryl is unsubstituted or substituted;
    (5) a heterocycle having 5 to 12 ring members, in which the heterocycle is unsubstituted or substituted; or
    (6) ($C_1$–$C_6$)-alkyl;
    (7) —CN;
    (8) —$NO_2$;
    (9) —O—($C_0$–$C_4$)-alkyl-aryl, in which alkyl is straight-chain or branched;
    (10) —O—($C_1$–$C_4$)-alkyl;
    (11) —$OR^{11}$;
    (12) —$N(R^{11})_2$;
    —$S(O)_xR^{11}$, in which x is the integer 0, 1, or 2; or
    (14) —$CF_3$;
      in which $R^{11}$ is as defined above;
$R^5$ is
  (1) hydrogen;
  (2) —OH; or
  (3) =O; and
$R^6$ is
  (1) phenyl, optionally mono- or disubstituted independently of one another by —CN, —$NO_2$, —O—($C_1$–$C_4$)-alkyl, —$N(R^{11})_2$, —NH—C(O)—$R^{11}$, —$S(O)_xR^{11}$, in which x is the integer 0, 1, or 2, or —C(O)—$R^{11}$, in which $R^{11}$ is as defined above; or
  (2) heteroaryl having 5 to 14 ring members, in which the heteroaryl is unsubstituted or substituted and is selected from pyrrole, furan, thiophene, imidazole, pyrazole, oxazole, isoxazole, thiazole, isothiazole, tetrazole, 1,3,4 oxadiazole, 1,2,3,5-oxathiadiazole-2-oxides, triazolones, oxadiazolones, isoxazolones, oxadiazolidinediones, triazoles which are substituted by F, CN, $CF_3$, or COO—($C_1$–$C_4$)-alkyl, 3-hydroxypyrrole-2,4-diones, 5-oxo-1,2,4-thiadiazoles, pyridine, pyrazine, pyrimidine, indole, isoindole, indazole, phthalazine, quinoline, isoquinoline, quinoxaline, quinazoline, cinnoline, carboline, and benzo-fused, cyclopenta-, cyclohexa-, or cyclohepta-fused derivatives of these heteroaryls.

3. A method for producing a pharmaceutical composition, comprising bringing at least one compound of claim 1 or 2 into a suitable administration form using a pharmaceutically suitable and physiologically tolerable excipient and, if appropriate, further suitable active compounds, additives, or auxiliaries.

4. A compound of claim 1 or 2, in which $R^9$(3) is 1-naphthyl, 2-naphthyl, 2-biphenylyl, 3-biphenylyl, or 4-biphenylyl.

5. A compound of claim 1 or 2, in which $R^9$(4) is 2- or 3-pyrrolyl, phenylpyrrolyl, 4-imidazolyl, methylimidazolyl, 1,3-thiazol-2-yl, 2-, 3-, or 4-pyridyl-N-oxide, 2-pyrazinyl, 2-, 4-, or 5-pyrimidinyl, 2-, 3-, or 5-indolyl, substituted 2-indolyl, 1-benzyl-2- or -3-indolyl, 4,5,6,7-tetrahydro-2-indolyl, cyclohepta[b]-5-pyrrolyl, 2-, 3-, or 4-quinolyl, 1-, 3-, or 4-isoquinolyl, 1-oxo-1,2-dihydro-3-isoquinolyl, 2-quinoxalinyl, 2-benzofuranyl, 2-benzothienyl, 2-benzoxazolyl, benzothiazolyl, dihydropyridinyl, pyrrolidinyl, piperazinyl, morpholinyl, thiomorpholinyl, tetrahydrothienyl, or benzodioxolanyl.

6. A compound of claim 1 or 2, in which $R^9$(4) is 4- or 5-phenyl-2-pyrrolyl, 1-methyl-2-, -4-, or -5-imidazolyl, 1-methyl-, 5-methyl-, 5-methoxy-, 5-benzyloxy-, 5-chloro-, or 4,5-dimethyl-2-indolyl, or 2- or 3-(N-methylpyrrolidinyl).

7. A compound of claim 1 or 2, in which $R^6$(2) is 2- or 3-pyrrolyl, phenylpyrrolyl, 2-furyl, 2-thienyl, 4-imidazolyl, methylimidazolyl, 1,3-thiazol-2-yl, 2-pyridyl, 3-pyridyl, 4-pyridyl, 2-, 3-, or 4-pyridyl-N-oxide, 2-pyrazinyl, 2-, 4-, or 5-pyrimidinyl, 2-, 3-, or 5-indolyl, substituted 2-indolyl, 1-benzyl-2- or -3-indolyl, 4,5,6,7-tetrahydro-2-indolyl, cyclohepta[b]-5-pyrrolyl, 2-, 3-, or 4-quinolyl, 1-, 3-, or 4-isoquinolyl, 1-oxo-1,2-dihydro-3-isoquinolyl, 2-quinoxalinyl, 2-benzofuranyl, 2-benzothienyl, 2-benzoxazolyl, benzothiazolyl, dihydropyridinyl, pyrrolidinyl, piperazinyl, morpholinyl, thiomorpholinyl, tetrahydrothienyl, or benzodioxolanyl.

8. A compound of claim 1 or 2, in which $R^6$(2) is 4- or 5-phenyl-2-pyrrolyl, 1-methyl-2-, -4- or -5-imidazolyl, 1-methyl-, 5-methyl-, 5-methoxy-, 5-benzyloxy-, 5-chloro-, or 4,5-dimethyl-2-indolyl, or 2- or 3-(N-methylpyrrolidinyl).

9. A method for treating disorders in whose course an increased activity of NFκB is involved, comprising administering to a patient in need thereof an effective amount of at least one compound of claim 1 or 2.

10. A method for treating rheumatoid arthritis, osteoarthritis, asthma, cardiac infarct, Alzheimer's disease, carcinomatous disorders, or atherosclerosis, comprising administering to a patient in need thereof an effective amount of at least one compound of claim 1 or 2.

11. A process for the preparation of a compound of claim 1 or 2, comprising
  a) reacting a compound of formula IV

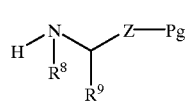

IV in which Pg is a suitable protective group, an amide group, or a hydroxyl group, and Z, $R^8$, and $R^9$ are as defined in formula II, with an acid chloride or an activated ester of the compound of formula III

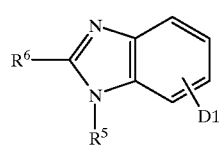

III where D1 is —COOH or sulfonylhalogen, and $R^5$ and $R^6$ are as defined in formula I, in the presence of a base or, optionally, of a dehydrating agent in solution and, after removal of the protective group, converting into a compound of formula I; or b) reacting a compound of formula IVa

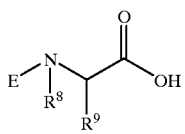

IVa in which $R^8$ and $R^9$ are as defined in formula II, and E is an N-amino protective group, with its carboxyl group coupled via an intermediate chain L to a polymeric resin of formula PS, a compound of formula V

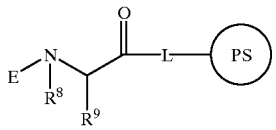

V resulting, which, after selective removal of the protective group E, is reacted with a compound of formula III, where $R^5$ and $R^6$ are as defined in formula I, in the presence of a base or, optionally, of a dehydrating agent to give a compound of formula VI

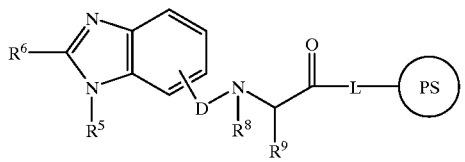

VI and converting the compound of formula VI, after removal of the polymeric resin, into a compound of formula I; or c) reacting a compound of formula V, after selective removal of the protective group E, with a compound of formula VII

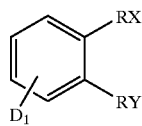

VII where $D_1$ is —COOH or sulfonylhalogen, and RX is halogen and RY is a radical —$NO_2$ or —NH—E, and E is a protective group, to give a compound of formula VIII

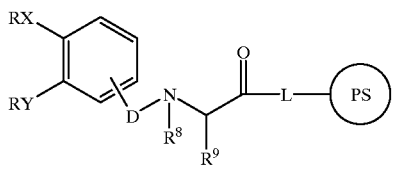

VIII and then reacting the compound of formula VIII with a compound of formula IX $NH_2$—$R^6$

IX in which $R^6$ is as defined in the compound of formula I, to give an intermediate compound of formula VIa

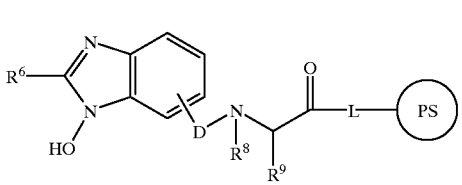

VIa then either converting the intermediate compound of formula VIa into a compound of formula I after removal of the polymeric resin, or reducing it to give a compound of formula VI, and converting into a compound of formula I after removal of the polymeric resin; or d) converting a compound of formula I into a physiologically tolerable salt.

12. A process of claim 11, in which the intermediate compound of formula VIa is reduced with tributylphosphine to give a compound of formula VI.

13. A pharmaceutical composition, comprising at least one compound of claim 1 or 2, and a pharmaceutically suitable and physiologically tolerable excipient, additive, and optionally other active compounds and auxiliaries.

14. A method for treating disorders in whose course an increased activity of NFκB is involved, comprising administering to a patient in need thereof an effective amount of at least one compound of claim 13.

15. A method for treating rheumatoid arthritis, osteoarthritis, asthma, cardiac infarct, Alzheimer's disease, carcinomatous disorders, or atherosclerosis, comprising administering to a patient in need thereof an effective amount of at least one compound of claim 13.

16. A compound of claim 1, in which $R^8$ is hydrogen;

$R^9$ is (1) histidine, tryptophan, serine, threonine, cysteine, methionine, asparagine, glutamine, lysine, arginine, glutamic acid, or aspartic acid;

(2) ($C_1$–$C_6$)-alkyl, in which alkyl is unsubstituted or mono- or disubstituted independently of one another by a radical selected from pyrrole, pyrrole mono- or disubstituted independently of one another by —($C_1$–$C_4$)-alkyl, pyrazole, phenyl, imidazole, triazole, thiophene, thiazole, oxazole, isoxazole, pyridine, pyrimidine, indole, benzothiophene, benzimidazole, benzoxazole, benzothiazole, azetidine, pyrroline, pyrrolidine, piperidine, isothiazole, diazepine, thiomorpholine, —CN, morpholine, azepine, 1,3,4-oxadiazole, —N($R^{13}$)-phenyl, wherein $R^{13}$ is defined below, pyrazine, ($C_3$–$C_6$)-cycloalkyl, —$OR^{11}$, —NH($R^{11}$), in which $R^{11}$ is as defined above, —S(O)$_x$—$R^{12}$, in which x is 0, 1, or 2, and $R^{12}$ is naphthyl, pyrimidinyl, morpholinyl, or phenyl, which are unsubstituted or mono- or disubstituted independently of one another by —OH, ($C_1$–$C_4$)-alkyl, —$CF_3$, halogen, —O—($C_1$–$C_4$)-alkyl, —COOH, —C(O)—O—($C_1$–$C_4$)-alkyl, —$NH_2$, or —NH—C(O)—($C_1$–$C_4$)-alkyl, or C(O)—$R^{12}$, in which $R^{12}$ is as defined above;

Z is —C(O)—$R^{10}$, tetrazole, ($C_1$–$C_6$)-alkyl, in which alkyl is mono- or disubstituted independently on one another by phenyl or —OH, or 1,3,4-oxadiazole, in which 1,3,4-oxadiazole is unsubstituted or monosubstituted by —NH$_2$, —NH(C$_1$–C$_4$)-alkyl, —N—[(C$_1$–C$_4$)-alkyl]$_2$, —NH—C(O)—(C$_1$–C$_4$)-alkyl, —NH—C(O)—NH—(C$_1$–C$_4$)-alkyl, —NH—C(O)—NH—(C$_3$–C$_7$)-cycloalkyl, —NH—C(O)—NH-aryl, —NH—C(O)—NH-phenyl, —NH—SO$_2$-aryl, —NH—SO$_2$—(C$_1$–C$_4$)-alkyl, —OH, or —(C$_1$–C$_4$)-alkyl, in which R$^{10}$ is —O—R$^{11}$, phenyl, pyrimidine, —OH, morpholinyl, —N(R$^{11}$)$_2$, or —NH$_2$;

R$^{11}$ is
  (1) —(C$_1$–C$_4$)-alkyl;
  (2) R$^{13}$; or
  (3) —N(R$^{13}$)$_2$, in which
    R$^{13}$ independently of one another is
      (a) hydrogen;
      (b) —(C$_1$–C$_6$)-alkyl;
      (c) —(C$_1$–C$_4$)-alkyl-O—(C$_1$–C$_4$)-alkyl;
      (d) —(C$_1$–C$_6$)-alkyl-N(R$^{13}$)$_2$;
      (e) halogen; or
      (f) —(C$_0$–C$_4$)-alkyl, mono- or disubstituted by aryl, imidazolyl, morpholinyl, or phenyl; or R$^8$ and R$^9$, together with the nitrogen and carbon to which they are each bonded, form a ring of formula IIa selected from pyrrole, pyrroline, pyrrolidine, pyridine, piperidine, piperylene, pyridazine, pyrimidine, pyrazine, piperazine, pyrazole, imidazole, pyrazoline, imidazoline, pyrazolidine, imidazolidine, oxazole, isoxazole, 2-isoxazolidine, isoxazolidine, morpholine, isothiazole, thiazole, tetrazole, 1,2,3,5-oxathiadiazole-2-oxides, oxadiazolones, isoxazolones, triazolones, oxadiazolidinediones, triazoles which are substituted by F, CN, CF$_3$, or COO—(C$_1$–C$_4$)-alkyl, 3-hydroxypyrro-2,4-diones, 5-oxo-1,2,4-thiadiazoles, 1,3,4-oxadiazole, isothiazolidine, thiomorpholine, indazole, thiadiazole, benzimidazole, quinoline, triazole, phthalazine, quinazoline, quinoxaline, purine, pteridine, indole, tetrahydroquinoline, tetrahydroisoquinoline, and isoquinoline; or R$^9$ and Z, together with the carbons to which they are each bonded, form a ring of formula IIc selected from pyrrole, pyrroline, pyrrolidine, pyridine, piperidine, piperylene, pyridazine, pyrimidine, pyrazine, piperazine, pyrazole, imidazole, pyrazoline, imidazoline, pyrazolidine, imidazolidine, oxazole, isoxazole, 2-isoxazolidine, isoxazolidine, morpholine, isothiazole, thiazole, isothiazolidine, thiomorpholine, indazole, thiadiazole, benzimidazole, quinoline, triazole, phthalazine, quinazoline, quinoxaline, purine, pteridine, indole, tetrahydroquinoline, tetrahydrolsoquinoline, isoquinoline, tetrazole, 1,2,3,5-oxathiadiazole-2-oxides, oxadiazolones, isoxazolones, triazolones, oxadiazolidinediones, triazoles which are substituted by F, CN, CF$_3$, or COO—(C$_1$–C$_4$)-alkyl, 3-hydroxypyrrole-2,4-diones, 1,3,4-oxadiazole, and 5-oxo-1,2,4-thiadiazoles; and the other substituents R$^1$, R$^2$, R$^3$, and R$^4$ are chosen independently of one another, and are
  (1) hydrogen;
  (2) halogen;
  (3) (C$_1$–C$_4$)-alkyl;
  (4) —CN;
  (5) —NO$_2$;
  (6) —O—(C$_0$–C$_4$)-alkyl-aryl, in which alkyl is straight-chain or branched;
  (7) —O—(C$_1$–C$_4$)-alkyl;
  (8) —N—(C$_0$–C$_4$)-alkyl-aryl, in which alkyl is straight-chain or branched;
  (9) —N—(C$_1$–C$_4$)-alkyl; or
  (10) —CF$_3$;

R$^5$ is
  (1) hydrogen;
  (2) —OH; or
  (3) =O; and

R$^6$ is
  (1) phenyl, mono- or disubstituted independently of one another by
    (1)(1) —CN;
    (1)(2) —NO$_2$;
    (1)(3) —O—(C$_1$–C$_4$)-alkyl; or
    (1)(4) —NH$_2$; or
  (2) heteroaryl having 5 to 14 ring members, in which the heteroaryl is unsubstituted or mono-, di-, or trisubstituted and is selected from the group consisting of pyrrole, furan, thiophene, imidazole, pyrazole, oxazole, isoxazole, thiazole, isothiazole, tetrazole, 1,3,4-oxadiazole, 1,2,3,5-oxathiadiazole-2-oxides, triazolones, oxadiazolones, isoxazolones, oxadiazolidinediones, triazoles which are substituted by F, CN, CF$_3$, or COO—(C$_1$–C$_4$)-alkyl, 3-hydroxypyrrole-2,4-diones, 5-oxo-1,2,4-thiadiazoles, pyridine, pyrazine, pyrimidine, indole, isoindole, indazole, phthalazine, quinoline, isoquinoline, quinoxaline, quinazoline, cinnoline, carboline, and benzo-fused, cyclopenta-, cyclohexa-, or cyclohepta-fused derivatives of these heteroaryls.

17. A compound of claim 16, in which R$^6$(2) is 2- or 3-pyrrolyl, phenylpyrrolyl, 2-furyl, 2-thienyl, 4-imidazolyl, methylimidazolyl, 1,3-thiazol-2-yl, 2-pyridyl, 3-pyridyl, 4-pyridyl, 2-, 3-, or 4-pyridyl-N-oxide, 2-pyrazinyl, 2-, 4-, or 5-pyrimidinyl, 2-, 3-, or 5-indolyl, substituted 2-indolyl, 1-benzyl-2- or -3-indolyl, 4,5,6,7-tetrahydro-2-indolyl, cyclohepta[b]-5-pyrrolyl, 2-, 3-, or 4-quinolyl, 1-, 3-, or 4-isoquinolyl, 1-oxo-1,2-dihydro-3-isoquinolyl, 2-quinoxalinyl, 2-benzofuranyl, 2-benzothienyl, 2-benzoxazolyl, benzothiazolyl, dihydropyridinyl, pyrrolidinyl, piperazinyl, morpholinyl, thiomorpholinyl, tetrahydrothienyl, or benzodioxolanyl.

18. A compound of claim 16, in which R$^6$(2) is 4- or 5-phenyl-2-pyrrolyl, 1-methyl-2-, -4- or -5-imidazolyl, 1-methyl-, 5-methyl-, 5-methoxy-, 5-benzyloxy-, 5-chloro-, or 4,5-dimethyl-2-indolyl, or 2- or 3-(N-methylpyrrolidinyl).

19. A pharmaceutical composition, comprising at least one compound of claim 16, and a pharmaceutically suitable and physiologically tolerable excipient, additive, and optionally other active compounds and auxiliaries.

20. A method for treating disorders in whose course an increased activity of NFκB is involved, comprising administering to a patient in need thereof an effective amount of at least one compound of claim 16.

21. A method for treating rheumatoid arthritis, osteoarthritis, asthma, cardiac infarct, Alzheimer's disease, carcinomatous disorders, or atherosclerosis, comprising administering to a patient in need thereof an effective amount of at least one compound of claim 16.

22. A compound of claim 1, in which R$^6$(1) is 1-naphthyl, 2-naphthyl, 2-biphenylyl, 3-biphenylyl, or 4-biphenylyl, and R$^6$(1) is unsubstituted or monosubstituted, disubstituted, or trisubstituted independently of one another by (C$_1$–C$_4$)-alkyl, (C$_1$–C$_4$)-alkoxy, hydroxymethyl, 1-hydroxyethyl, or 2-hydroxyethyl.

23. A method for treating disorders in whose course an increased activity of NFκB is involved, comprising administering to a patient in need thereof an effective amount of at least one compound of formula I

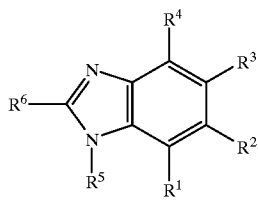

or a stereoisomeric form of the compound of formula I or a physiologically tolerable salt of the compound of formula I, where at least one of the substituents $R^1$, $R^2$, $R^3$, and $R^4$ is a radical of formula II

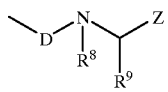

in which:
D is —C(O)—, —S(O)—, or —S(O)$_2$—;
$R^8$ is hydrogen or (C$_1$–C$_4$)alkyl;
$R^9$ is
(1) glycine, alanine, valine, leucine, isoleucine, phenylalanine, tyrosine, tryptophan, serine, threonine, cysteine, methionine, asparagine, glutamine, lyslne, histidine, arginine, glutamic acid, aspartic acid, 2-aminoadipic acid, 2-aminobutyric acid, 2-aminoisobutyric acid, 2,3-diaminopropionic acid, 2,4-diaminobutyric acid, 1,2,3,4-tetrahydroisoquinoline-1-carboxylic acid, 1,2,3,4-tetrahydroisoquinoline-3-carboxylic acid, 2-aminopimelic acid, 2-amino-3-phenylaminoethyl-propionic acid, 2-amino-3-phenylamino-propionic acid, phenylglycine, 3-(2-thienyl)alanine, 3-(3-thienyl) alanine, 2-(2-thienyl)glycine, 2-aminoheptanoic acid, pipecolic acid, hydroxylysine, sarcosine, N-methylisoleucine, 6-N-methyllysine, N-methylvaline, norvaline, norleucine, ornithine, allo-isoleucine, allo-threonine, allo-hydroxylysine, 4-hydroxyproline, 3-hydroxyproline, 3-(2-naphthyl) alanine, 3-(1-naphthylalanine), homophenylalanine, homocysteine, homocysteic acid, homotryptophan, cysteic acid, 3-(2-pyridyl)alanine, 3-(3-pyridyl) alanine, 3-(4-pyridyl)alanine, phosphinothricin, 4-fluorophenylalanine, 3-fluorophenylalanine, 4-fluorophenylalanine, 3-fluorophenylalanine, 3-fluorophenylalanine, 2-fluorophenylalanine, 4-chlorophenylalanine, 4-nitrophenylalanine, 4-aminophenylalanine, cyclohexylalanine, citrulline, 5-fluorotryptophan, 5-methoxytryptophan, methionine sulfone, methionine sulfoxide, or —NH—NR$^{11}$—CON(R$^{11}$)$_2$, wherein $R^{11}$ is as defined below;
(2) aryl, in which aryl is unsubstituted or substituted:
(3) heteroaryl having 5 to 14 ring members, in which heteroaryl is unsubstituted or substituted;
(4) a heterocycle having 5 to 12 ring members, in which heterocycle is unsubstituted or substituted;
(5) (C$_1$–C$_6$)-alkyl, in which alkyl is unsubstituted or mono-, di-, or trisubstituted independently of one another by
(5)(1) aryl, in which aryl is unsubstituted or substituted;
(5)(2) heteroaryl having 5 to 14 ring members, in which heteroaryl is unsubstituted or substituted;
(5)(3) a heterocycle having 5 to 12 ring members, in which the heterocycle is unsubstituted or substituted;
(5)(4) —O—R$^{11}$;
(5)(5) =O;
(5)(6) halogen;
(5)(7) —CN;
(5)(8) —CF$_3$;
(5)(9) —S(O)$_x$—R$^{11}$, in which x is the integer zero, 1, or 2;
(5)(10) —C(O)—O—R$^{11}$;
(5)(11) —C(O)—N(R$^{11}$)$_2$;
(5)(12) —N(R$^{11}$)$_2$;
(5)(13) (C$_3$–C$_8$)-cycloalkyl;
(5)(14) a radical of formula

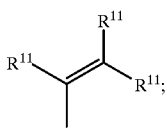

or
(5)(15) a radical of formula

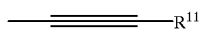

in which
$R^{11}$ is
(a) hydrogen;
(b) (C$_1$–C$_6$)-alkyl, in which alkyl is unsubstituted or mono-, di-, or trisubstituted independently of one another by
(1) aryl, in which aryl is unsubstituted or substituted;
(2) heteroaryl having 5 to 14 ring members, in which heteroaryl is unsubstituted or substituted;
(3) a heterocycle having 5 to 12 ring members, in which heterocycle is unsubstituted or substituted;
(4) halogen;
(5) —N—(C$_1$–C$_6$)$_n$-alkyl, in which n is the integer 0, 1, or 2 and alkyl is unsubstituted or mono-, di-, or trisubstituted independently of one another by halogen or by —COOH;
(6) —O—(C$_1$–C$_5$)-alkyl; or
(7) —COOH;
(c) aryl, in which aryl is unsubstituted or substituted;
(d) heteroaryl having 5 to 14 ring members, in which heteroaryl is unsubstituted or substituted; or
(e) a heterocycle having 5 to 12 ring members, in which heterocycle is unsubstituted or substituted; and
in the case of (R$^{11}$)$_2$, R$^{11}$ independently of one another has the meaning of (a) to (e);
Z is
(1) aryl, in which aryl is unsubstituted or substituted;
(2) heteroaryl having 5 to 14 ring members, in which heteroaryl is unsubstituted or substituted;
(3) a heterocycle having 5 to 12 ring members, in which heterocycle is unsubstituted or substituted;
(4) —(C$_1$–C$_6$)-alkyl, in which alkyl is substituted or unsubstituted independently of one another by (4)(1) aryl, in which aryl is unsubstituted or substituted;
(4)(2) heteroaryl having 5 to 14 ring members, in which heteroaryl is unsubstituted or substituted;
(4)(3) a heterocycle having 5 to 12 ring members, in which heterocycle is unsubstituted or substituted;
(4)(4) halogen;
(4)(5) —N—$(C_1-C_6)_n$-alkyl, in which n is the integer 0, 1, or 2, and alkyl is unsubstituted or mono-, di-, or trisubstituted independently of one another by halogen or by —COOH;
(4)(6) —O—$(C_1-C_6)$-alkyl; or
(4)(7) —COOH; or
(5) —C(O)—$R^{10}$, in which
  $R^{10}$ is
  (1) —O—$R^{11}$; or
  (2) —N$(R^{11})_2$;
  in which $R^{11}$ is as defined above; or
$R^8$ and $R^9$, together with the nitrogen and carbon to which they are each bonded, form a heterocyclic ring of formula IIa

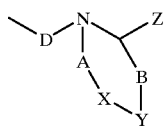

IIa in which:
D, Z, and $R^{10}$ are as defined in formula II;
A is nitrogen or —CH$_2$—;
B is oxygen, sulfur, nitrogen, or —CH$_2$;
X is oxygen, sulfur, nitrogen, or —CH$_2$;
Y is absent or is oxygen, sulfur, nitrogen, or —CH$_2$—; or
X and Y together form a phenyl, 1,2-diazine, 1,3-diazine, or a 1,4-diazine radical;
  where the ring system formed by N, A, X, Y, B, and the carbon contains no more than one oxygen, X is not oxygen, sulfur, or nitrogen if A is a nitrogen atom; contains no more than one sulfur; contains 1, 2, 3, or 4 nitrogens; and where oxygen and sulfur do not occur at the same time;
  where the ring system formed by N, A, X, Y, B, and the carbon is unsubstituted or mono-, di, or trisubstituted independently of one another by $(C_1-C_8)$-alkyl, in which alkyl is unsubstituted or mono- or disubstituted by
    (1)(1) —OH;
    (1)(2) $(C_1-C_8)$-alkoxy, in which alkoxy is straight-chain or branched;
    (1)(3) halogen;
    (1)(4) —NO$_2$;
    (1)(5) —NH$_2$;
    (1)(6) —CF$_3$;
    (1)(7) —OH;
    (1)(8) methylenedioxy;
    (1)(9) —C(O)—CH$_3$;
    (1)(10) —CH(O);
    (1)(11) —CN;
    (1)(12) —COOH;
    (1)(13) —C(O)—NH$_2$;
    (1)(14) $(C_1-C_4)$-alkoxycarbonyl, in which alkoxycarbonyl is straight-chain or branched;
    (1)(15) phenyl;
    (1)(16) phenoxy;
    (1)(17) benzyl;
    (1)(18) benzyloxy; or
    (1)(19) tetrazolyl; or
$R^9$ and Z together with the carbons to which they each are bonded form a heterocyclic ring of formula IIc

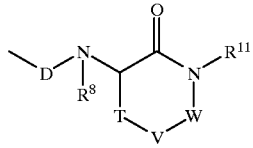

IIc in which:
D, $R^8$, and $R^{11}$ are as defined in formula II;
T is oxygen, sulfur, nitrogen, or —CH$_2$—;
W is oxygen, sulfur, nitrogen, or —CH$_2$—;
V is absent or is oxygen, sulfur, nitrogen, or —CH$_2$—; or
T and V together form a phenyl, 1,2-diazine, 1,3-diazine, or a 1,4-diazine radical; or
V and W together form a phenyl, 1,2-diazine, 1,3-diazine, or a 1,4-diazine radical;
  where the ring system formed by N, T, V, W, and the two carbons contains no more than one oxygen, no more than one sulfur, and 1, 2, 3, or 4 nitrogens; where oxygen and sulfur do not occur at the same time; and where the ring system formed by N, T, V, W, and the two carbons is unsubstituted or mono, di-, or trisubstituted independently of one another by the substituents defined above under (1)(1) to (1)(19); and
  the other substituents $R^1$, $R^2$, $R^3$, and $R^4$ are chosen independently of one another, and are
  (1) hydrogen;
  (2) halogen;
  (3) $(C_1-C_4)$-alkyl;
  (4) heteroaryl having 5 to 14 ring members, in which heteroaryl is unsubstituted or substituted;
  (5) a heterocycle having 5 to 12 ring members, in which heterocycle is unsubstituted or substituted;
  (6) $(C_1-C_6)$-alkyl;
  (7) —CN;
  (8) —NO$_2$;
  (9) —O—$(C_0-C_4)$-alkyl-aryl, in which alkyl is straight-chain or branched;
  (10) —O—$(C_1-C_4)$-alkyl;
  (11) —OR$^{11}$;
  (12) —N$(R^{11})_2$;
  (13) —S(O)$_x$R$^{11}$, in which x is the integer 0, 1, or 2; or
  (14) —CF$_3$;
    in which $R^{11}$ is as defined above;
$R^5$ is
  (1) hydrogen;
  (2) —OH; or
  (3) =O; and
$R^6$ is
  (1) aryl, in which aryl is unsubstituted or substituted, and is selected from phenyl, naphthyl, biphenylyl, anthryl, and fluorenyl, in which aryl is unsubstituted, monosubstituted, or polysubstituted independently of one another by $(C_1-C_8)$-alkyl, $(C_1-C_8)$-alkoxy, halogen, nitro, amino, trifluoromethyl, hydroxyl, hydroxy-$(C_1-C_4)$-alkyl, methylenedioxy, ethylenedioxy, formyl, acetyl, cyano, hydroxycarbonyl, aminocarbonyl, $(C_1-C_4)$- alkoxycarbonyl, phenyl, phenoxy, benzyl, benzyloxy, and tetrazolyl; or (2) heteroaryl having 5 to 14 ring members, unsubstituted or mono-, di-, or trisubstituted; or (3) a heterocycle having 5 to 12 ring members, unsubstituted or mono-, di-, or trisubstituted.

24. A method for treating disorders in whose course an increased activity of is involved, comprising administering to a patient in need thereof an effective amount of at least one compound of formula I

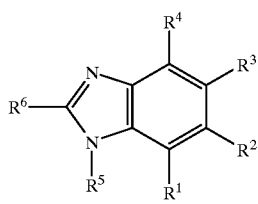

I or a stereoisomeric form of the compound of formula I or a physiologically tolerable salt of the compound of formula I, where at least one of the substituents $R_1$, $R^2$, $R^3$, and $R^4$ is a radical of formula II

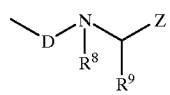

II in which:
D is —C(O)—, —S(O)—, or —S(O)$_2$—;
$R^8$ is hydrogen or ($C_1$–$C_4$)-alkyl;
$R^9$ is
(1) glycine, alanine, valine, leucine, isoleucine, phenylalanine, tyrosine, tryptophan, serine, threonine, cysteine, methionine, asparagine, glutamine, lysine, histidine, arginine, glutamic acid, aspartic acid, 2-aminoadipic acid, 2-aminobutyric acid, 2-aminoisobutyric acid, 2,3-diaminopropionic acid, 2,4-diaminobutyric acid, 1,2,3,4-tetrahydroisoquinoline-1-carboxylic acid, 1,2,3,4-tetrahydroisoquinoline-3-carboxylic acid, 2-aminopimelic acid, 2-amino-3-phenylaminoethylpropionic acid, 2-amino-3-phenylamino-propionic acid, phenylglycine, 3-(2-thienyl)alanine, 3-(3-thienyl) alanine, 2-(2-thienyl)glycine, 2-aminoheptanoic acid, pipecolic acid, hydroxylysine, sarcosine, N-methylisoleucine, 6-N-methyllysine, N-methylvaline, norvaline, norleucine, ornithine, alloisoleucine, allo-threonine, allo-hydroxylysine, 4-hydroxyproline, 3-hydroxyproline, 3-(2-naphthyl) alanine, 3-(1-naphthylalanine), homophenylalanine, homocysteine, homocysteic acid, homotryptophan, cysteic acid, 3-(2-pyridyl)alanine, 3-(3-pyridyl) alanine, 3-(4-pyridyl)alanine, phosphinothricin, 4-fluorophenylalanine, 3-fluorophenylalanine, 4-fluorophenylalanine, 3-fluorophenylalanine, 3-fluorophenylalanine, 2-fluorophenylalanine, 4-chlorophenylalanine, 4-nitrophenylalanine, 4-aminophenylalanine, cyclohexylalanine, citrulline, 5-fluorotryptophan, 5-methoxytryptophan, methionine sulfone, methionine sulfoxide, or —NH—NR$^{11}$—CON ($R^{11})_2$, wherein $R^{11}$ is as defined below;

(2) aryl, in which aryl is unsubstituted or substituted;

(3) heteroaryl having 5 to 14 ring members, in which heteroaryl is unsubstituted or substituted;

(4) a heterocycle having 5 to 12 ring members, in which heterocycle is unsubstituted or substituted;

(5) ($C_1$–$C_6$)-alkyl, in which alkyl is unsubstituted or mono-, di-, or trisubstituted independently of one another by (5)(1) aryl, in which aryl is unsubstituted or substituted;

(5)(2) heteroaryl having 5 to 14 ring members, in which heteroaryl is unsubstituted or substituted;

(5)(3) a heterocycle having 5 to 12 ring members, in which the heterocycle is unsubstituted or substituted;

(5)(4) —O—R$^{11}$;

(5)(5) =O;

(5)(6) halogen;

(5)(7) —CN;

(5)(8) —CF$_3$;

(5)(9) —S(O)$_x$—R$^{11}$, in which x is the integer zero, 1, or 2;

(5)(10) —C(O)—O—R$^{11}$;

(5)(11) —C(O)—N(R$^{11})_2$;

(5)(12) —N(R$^{11})_2$;

(5)(13) ($C_3$–$C_6$)-cycloalkyl;

(5)(14) a radical of formula

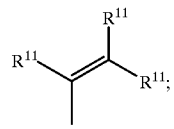

or
(5)(15) a radical of formula

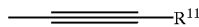

in which
R$^{11}$ is
(a) hydrogen;
(b) ($C_1$–$C_6$)-alkyl, in which alkyl is unsubstituted or mono-, di, or trisubstituted independently of one another by
(1) aryl, in which aryl is unsubstituted or substituted;
(2) heteroaryl having 5 to 14 ring members, in which heteroaryl is unsubstituted or substituted;
(3) a heterocycle having 5 to 12 ring members, in which heterocycle is unsubstituted or substituted;
(4) halogen;
(5) —N—($C_1$–$C_6$)$_n$-alkyl, in which n is the integer 0, 1, or 2 and alkyl is unsubstituted or mono-, di-, or trisubstituted independently of one another by halogen or by —COOH;
(6) —O—($C_1$–$C_6$)alkyl; or
(7) —COOH;
(c) aryl, in which aryl is unsubstituted or substituted;
(d) heteroaryl having 5 to 14 ring members, in which heteroaryl is unsubstituted or substituted; or
(e) a heterocycle having 5 to 12 ring members, in which heterocycle is unsubstituted or substituted; and
in the case of (R$^{11})_2$, R$^{11}$ independently of one another has the meaning of (a) to (e);

Z is
(1) aryl, in which aryl is unsubstituted or substituted;
(2) heteroaryl having 5 to 14 ring members, in which heteroaryl is unsubstituted or substituted;
(3) a heterocycle having 5 to 12 ring members, in which heterocycle is unsubstituted or substituted;
(4) —$(C_1-C_6)$-alkyl, in which alkyl is substituted or unsubstituted independently of one another by
   (4)(1) aryl, in which aryl is unsubstituted or substituted;
   (4)(2) heteroaryl having 5 to 14 ring members, in which heteroaryl is unsubstituted or substituted;
   (4)(3) a heterocycle having 5 to 12 ring members, in which heterocycle is unsubstituted or substituted;
   (4)(4) halogen;
   (4)(5) —N—$(C_1-C_6)_n$-alkyl, in which n is the integer 0, 1, or 2, and alkyl is unsubstituted or mono-, di-, or trisubstituted independently of one another by halogen or by —COOH;
   (4)(6) —O—$(C_1-C_6)$-alkyl; or
   (4)(7) —COOH; or
(5) —C(O)—$R^{10}$, in which
   $R^{10}$ is
   (1) —O—$R^{11}$; or
   (2) —N$(R^{11})_2$;
   in which $R^{11}$ is as defined above; or
$R^8$ and $R^9$, together with the nitrogen and carbon to which they are each bonded, form a heterocyclic ring of formula IIa

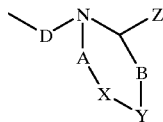

IIa in which:
D, Z, and $R^{10}$ are as defined in formula II;
A is nitrogen or —$CH_2$—;
B is oxygen, sulfur, nitrogen, or —$CH_2$;
X is oxygen, sulfur, nitrogen, or —$CH_2$;
Y is absent or is oxygen, sulfur, nitrogen, or —$CH_2$—; or
X and Y together form a phenyl, 1,2-diazine, 1,3-diazine, or a 1,4-diazine radical;
   where the ring system formed by N, A, X, Y, B, and the carbon contains no more than one oxygen, X is not oxygen, sulfur, or nitrogen if A is a nitrogen atom; contains no more than one sulfur; contains 1, 2, 3, or 4 nitrogens; and where oxygen and sulfur do not occur at the same time;
   where the ring system formed by N, A, X, Y, B, and the carbon is unsubstituted or mono-, di-, or trisubstituted independently of one another by $(C_1-C_8)$-alkyl, in which alkyl is unsubstituted or mono- or disubstituted by
      (1)(1) —OH;
      (1)(2) $(C_1-C_8)$-alkoxy, in which alkoxy is straight-chain or branched;
      (1)(3) halogen;
      (1)(4) —$NO_2$;
      (1)(5) —$NH_2$;
      (1)(6) —$CF_3$;
      (1)(7) —OH;
      (1)(8) methylenedioxy;
      (1)(9) —C(O)—$CH_3$;
      (1)(10) —CH(O);
      (1)(11) —CN;
      (1)(12) —COOH;
      (1)(13) —C(O)—$NH_2$;
      (1)(14) $(C_1-C_4)$-alkoxycarbonyl, in which alkoxycarbonyl is straight-chain or branched;
      (1)(15) phenyl;
      (1)(16) phenoxy;
      (1)(17) benzyl;
      (1)(18) benzyloxy; or
      (1)(19) tetrazolyl; or
$R^9$ and Z together with the carbons to which they each are bonded form a heterocyclic ring of formula IIc

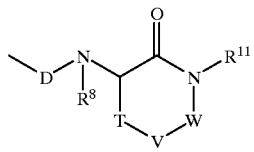

IIc in which;
D, $R^8$, and $R^{11}$ are as defined in formula II;
T is oxygen, sulfur, nitrogen, or —$CH_2$—;
W is oxygen, sulfur, nitrogen, or —$CH_2$—;
V is absent or is oxygen, sulfur, nitrogen, or —$CH_2$—; or
T and V together form a phenyl, 1,2-diazine, 1,3-diazine, or a 1,4-diazine radical; or
V and W together form a phenyl, 1,2-diazine, 1,3-diazine, or a 1,4-diazine radical;
   where the ring system formed by N, T, V, W, and the two carbons contains no more than one oxygen, no more than one sulfur, and 1, 2, 3, or 4 nitrogens; where oxygen and sulfur do not occur at the same time; and where the ring system formed by N, T, V, W, and the two carbons is unsubstituted or mono-, di-, or trisubstituted independently of one another by the substituents defined above under (1)(1) to (1)(19); and
the other substituents $R^1$, $R^2$, $R^3$, and $R^4$ are chosen independently of one another, and are
(1) hydrogen;
(2) halogen;
(3) $(C_1-C_4)$-alkyl;
(4) heteroaryl having 5 to 14 ring members, in which heteroaryl is unsubstituted or substituted;
(5) a heterocycle having 5 to 12 ring members, in which heterocycle is unsubstituted or substituted;
(6) $(C_1-C_6)$-alkyl;
(7) —CN;
(8) —$NO_2$;
(9) —O—$(C_0-C_4)$-alkyl-aryl, in which alkyl is straight-chain or branched;
(10) —O—$(C_1-C_4)$-alkyl;
(11) —$OR^{11}$;
(12) —N$(R^{11})_2$;
(13) —$S(O)_xR^{11}$, in which x is the integer 0, 1, or 2; or
(14) —$CF_3$;
in which $R^{11}$ is as defined above;
$R^5$ is
(1) hydrogen;
(2) —OH; or
(3) =O; and R⁶ is
- (1) phenyl, optionally mono- or disubstituted independently of one another by —CN, —NO₂, —O—($C_1$–$C_4$)-alkyl, —N($R^{11}$)₂, —NH—C(O)—$R^{11}$, —S(O)$_x R^{11}$, in which x is the integer 0, 1, or 2, —C(O)—$R^{11}$, in which $R^{11}$ is as defined above, or —($C_1$–$C_4$)-alkyl-NH₂; or
- (2) heteroaryl having 5 to 14 ring members, unsubstituted or mono-, di-, or trisubstituted; or
- (3) a heterocycle having 5 to 12 ring members, unsubstituted or mono-, di-, or trisubstituted.

25. The method of claim 24, comprising administering to a patient in need thereof an effective amount of at least one compound of formula I, in which:

$R^8$ is hydrogen;

$R^9$ is
- (1) glycine, alanine, valine, leucine, isoleucine, phenylalanine, tyrosine, tryptophan, serine, threonine, cysteine, methionine, asparagine, glutamine, lysine, histidine, arginine, glutamic acid, aspartic acid, 2-aminoadipic acid, 2-aminobutyric acid, 2-aminoisobutyric acid, 2,3-diaminopropionic acid, 2,4-diaminobutyric acid, 1,2,3,4-tetrahydroisoquinoline-1-carboxylic acid, 1,2,3,4-tetrahydroisoquinoline-3-carboxylic acid, 2-aminopimelic acid, 2-amino-3-phenylaminoethyl-propionic acid, 2-amino-3-phenylamino-propionic acid, phenylglycine, 3-(2-thienyl)alanine, 3-(3-thienyl)alanine, 2-(2-thienyl)glycine, 2-aminoheptanoic acid, pipecolic acid, hydroxylysine, sarcosine, N-methylisoleucine, 6-N-methyllysine, N-methylvaline, norvaline, norleucine, ornithine, allo-isoleucine, allo-threonine, allo-hydroxylysine, 4-hydroxyproline, 3-hydroxyproline, 3-(2-naphthyl)alanine, 3-(1-naphthylalanine), homophenylalanine, homocysteine, homocysteic acid, homotryptophan, cysteic acid, 3-(2-pyridyl)alanine, 3-(3-pyridyl)alanine, 3-(4-pyridyl)alanine, phosphinothricin, 4-fluorophenylalanine, 3-fluorophenylalanine, 4-fluorophenylalanine, 3-fluorophenylalanine, 3-fluorophenylalanine, 2-fluorophenylalanine, 4-chlorophenylalanine, 4-nitrophenylalanine, 4-aminophenylalanine, cyclohexylalanine, citrulline, 5-fluorotryptophan, 5-methoxytryptophan, methionine sulfone, methionine sulfoxide, or —NH—NR$^{11}$—CON(R$^{11}$)₂, wherein R$^{11}$ is as defined below;
- (2) ($C_1$–$C_6$)-alkyl, in which alkyl is unsubstituted or mono- or disubstituted independently of one another by a radical selected from pyrrole, pyrrole mono- or disubstituted independently of one another by —($C_1$–$C_4$)-alkyl, pyrazole, phenyl, imidazole, triazole, thiophene, thiazole, oxazole, isoxazole, pyridine, pyrimidine, indole, benzothiophene, benzimidazole, benzoxazole, benzothiazole, azetidine, pyrroline, pyrrolidine, piperidine, isothiazole, diazepine, thiomorpholine, —CN, morpholine, azepine, 1,3,4-oxadiazole, —N(R$^{13}$)-phenyl, wherein R$^{13}$ is defined below, pyrazine, ($C_3$–$C_6$)-cycloalkyl, —OR$^{11}$, —NH(R$^{11}$), in which R$^{11}$ is as defined above, —S(O)$_x$—R$^{12}$, in which x is 0, 1, or 2, and R$^{12}$ is naphthyl, pyrimidinyl, morpholinyl, or phenyl, which are unsubstituted or mono- or disubstituted independently of one another by —OH, ($C_1$–$C_4$)-alkyl, —CF₃, halogen, —O—($C_1$–$C_4$)-alkyl, —COOH, —C(O)—O—($C_1$–$C_4$)-alkyl, —NH₂, or —NH—C(O)—($C_1$–$C_4$)-alkyl, or C(O)—R$^{12}$, in which R$^{12}$ is as defined above;

Z is —C(O)—$R_{10}$, tetrazole, ($C_1$–$C_6$)-alkyl, in which alkyl is unsubstituted or mono- or disubstituted independently of one another by phenyl or —OH, or 1,3,4-oxadiazole, in which 1,3,4-oxadiazole is unsubstituted or monosubstituted by —NH₂, —NH($C_1$–$C_4$)-alkyl, —N—[($C_{193}$–$C_4$)-alkyl]₂, —NH—C(O)—($C_1$–$C_4$)-alkyl, —NH—C(O)—NH—($C_1$–$C_4$)-alkyl, —NH—C(O)—NH—($C_3$–$C_7$)-cycloalkyl, —NH—C(O)—NH—aryl, —NH—C(O)—NH-phenyl, —NH—SO₂-aryl, —NH—SO₂—($C_1$–$C_4$)-alkyl, —OH, or —($C_1$–$C_4$)-alkyl, in which $R^{10}$ is —O—$R^{11}$, phenyl, pyrimidine, —OH, morpholinyl, —N($R^{11}$)₂, or —NH₂;

$R^{11}$ is
- (1) —($C_1$–$C_4$)-alkyl;
- (2) $R^{13}$; or
- (3) —N($R^{13}$)₂, in which
  $R^{13}$ independently of one another is
  - (a) hydrogen;
  - (b) —($C_1$–$C_6$)-alkyl;
  - (c) —($C_1$–$C_4$)-alkyl-O—($C_1$–$C_4$)-alkyl;
  - (d) —($C_1$–$C_6$)-alkyl-N($R^{13}$)₂;
  - (e) halogen; or
  - (f) —($C_0$–$C_4$)-alkyl, mono- or disubstituted by aryl, imidazolyl, morpholinyl, or phenyl; or $R^8$ and $R^9$, together with the nitrogen and carbon to which they are each bonded, form a ring of formula IIa selected from pyrrole, pyrroline, pyrrolidine, pyridine, piperidine, piperylene, pyridazine, pyrimidine, pyrazine, piperazine, pyrazole, imidazole, pyrazoline, imidazoline, pyrazolidine, imidazolidine, oxazole, isoxazole, 2-isoxazolidine, isoxazolidine, morpholine, isothiazole, thiazole, tetrazole, 1,2,3,5-oxathiadiazole-2-oxides, oxadiazolones, isoxazolones, triazolones, oxadiazolidinediones, triazoles which are substituted by F, CN, CF₃, or COO—($C_1$–$C_4$)-alkyl, 3-hydroxypyrro-2,4-diones, 5-oxo-1,2,4-thiadiazoles, 1,3,4-oxadiazole, isothiazolidine, thiomorpholine, indazole, thiadiazole, benzimidazole, quinoline, triazole, phthalazine, quinazoline, quinoxaline, purine, pteridine, indole, tetrahydroquinoline, tetrahydroisoquinoline, and isoquinoline; or $R^9$ and Z, together with the carbons to which they are each bonded, form a ring of formula IIc selected from pyrrole, pyrroline, pyrrolidine, pyridine, piperidine, piperylene, pyridazine, pyrimidine, pyrazine, piperazine, pyrazole, imidazole, pyrazoline, imidazoline, pyrazolidine, imidazolidine, oxazole, isoxazole, 2-isoxazolidine, isoxazolidine, morpholine, isothiazole, thiazole, isothiazolidine, thiomorpholine, indazole, thiadiazole, benzimidazole, quinoline, triazole, phthalazine, quinazoline, quinoxaline, purine, pteridine, indole, tetrahydroquinoline, tetrahydroisoquinoline, isoquinoline, tetrazole, 1,2,3,5-oxathiadiazole-2-oxides, oxadiazolones, isoxazolones, triazolones, oxadiazolidinediones, triazoles which are substituted by F, CN, CF₃, or COO—($C_1$–$C_4$)-alkyl, 3-hydroxypyrrole-2,4-diones, 1,3,4-oxadiazole, and 5-oxo-1,2,4-thiadiazoles; and the other substituents $R^1$, $R^2$, $R^3$, and $R^4$ are chosen independently of one another, and are
- (1) hydrogen;
- (2) halogen;
- (3) ($C_1$–$C_4$)-alkyl;
- (4) —CN;
- (5) —NO₂;

133

(6) —O—(C₀–C₄)alkyl-aryl, in which alkyl is straight-chain or branched;
(7) —O—(C₁–C₄)-alkyl;
(8) —N—(C₀–C₄)-alkyl-aryl, in which alkyl is straight-chain or branched;
(9) —N—(C₁–C₄)-alkyl; or
(10) —CF₃;

R⁵ is
(1) hydrogen;
(2) —OH; or
(3) =O; and

R⁶ is
(1) phenyl, mono- or disubstituted independently of one another by
  (1)(1) —CN;
  (1)(2) —NO₂;
  (1)(3) —O—(C₁–C₄)-alkyl;
  (1)(4) —NH₂; or
  (1)(5) —(C₁–C₄)-alkyl-NH₂; or
(2) heteroaryl having 5 to 14 ring members, in which the heteroaryl is unsubstituted or mono-, di-, or trisubstituted independently of one another by —N—R¹⁴, in which R¹⁴ is —(C₁–C₆)-alkyl, —(C₃–C₆)-cycloalkyl, or phenyl, halogen, —OH, or —(C₁–C₄)-alkyl; or
(3) a heterocycle having 5 to 12 ring members, in which the heterocycle is unsubstituted or mono-, di-, or trisubstituted independently of one another by —N—R¹⁴, in which R¹⁴ is —(C₁–C₆)-alkyl, —(C₃–C₆)-cycloalkyl, or phenyl, halogen, —OH, or —(C₁–C₄)-alkyl.

26. A method for treating rheumatoid arthritis, osteoarthritis, asthma, cardiac infarct, Alzheimer's disease, carcinomatous disorders, or atherosclerosis, comprising administering to a patient in need thereof an effective amount of at least one compound of formula I

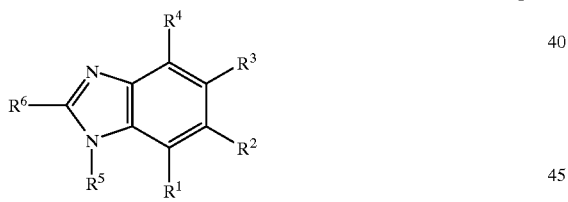

I or a stereoisomeric form of the compound of formula I or a physiologically tolerable salt of the compound of formula I, where at least one of the substituents R¹, R², R³, and R⁴ is a radical of formula II

II in which;
D is —C(O)—, —S(O)—, or —S(O)₂—;
R⁸ is hydrogen or (C₁–C₄)-alkyl;
R⁹ is
(1) glycine, alanine, valine, leucine, isoleucine, phenylalanine, tyrosine, tryptophan, serine, threonine, systeine, methionine, asparagine, glutamine, lysine, histidine, arginine, glutamic acid, aspartic acid, 2-aminoadipic acid, 2-aminobutyric acid, 2-aminoisobutyric acid, 2,3-diaminopropionic acid, 2,4-diaminobutyric acid, 1,2,3,4-tetrahydroisoquinoline-1-carboxylic acid, 1,2,3,4-tetrahydroisoquinoline-3-carboxylic acid, 2-aminopimelic acid, 2-amino-3-phenylaminoethyl-propionic acid, 2-amino-3-phenylamino-propionic acid, phenylglycine, 3-(2-thienyl)alanine, 3-(3-thienyl)alanine, 2-(2-thienyl)glycine, 2-aminoheptanoic acid, pipecolic acid, hydroxylysine, sarcosine, N-methylisoleucine, 6-N-methyllysine, N-methylvaline, norvaline, norleucine, ornithine, allo-isoleucine, allo-threonine, allo-hydroxylysine, 4-hydroxyproline, 3-hydroxyproline, 3-(2-naphthyl)alanine, 3-(1-naphthylalanine), homophenylalanine, homocysteine, homocysteic acid, homotryptophan, cysteic acid, 3-(2-pyridyl)alanine, 3-(3-pyridyl)alanine, 3-(4-pyridyl)alanine, phosphinothricin, 4-fluorophenylalanine, 3-fluorophenylalanine, 4-fluorophenylalanine, 3-fluorophenylalanine, 3-fluorophenylalanine, 2-fluorophenylalanine, 4-chlorophenylalanine, 4-nitrophenylalanine, 4-aminophenylalanine, cyclohexylalanine, citrulline, 5-fluorotryptophan, 5-methoxytryptophan, methionine sulfone, methionine sulfoxide, or —NH—NR¹¹—CON(R¹¹)₂, wherein R¹¹ is as defined below;
(2) aryl, in which aryl is unsubstituted or substituted;
(3) heteroaryl having 5 to 14 ring members, in which heteroaryl is unsubstituted or substituted;
(4) a heterocycle having 5 to 12 ring members, in which heterocycle is unsubstituted or substituted;
(5) (C₁–C₆)-alkyl, in which alkyl is unsubstituted or mono-, di-, or trisubstituted independently of one another by
  (5)(1) aryl, in which aryl is unsubstituted or substituted;
  (5)(2) heteroaryl having 5 to 14 ring members, in which heteroaryl is unsubstituted or substituted;
  (5)(3) a heterocycle having 5 to 12 ring members, in which the heterocycle is unsubstituted or substituted;
  (5)(4) —O—R¹¹;
  (5)(5) =O;
  (5)(6) halogen;
  (5)(7) —CN;
  (5)(8) —CF₃;
  (5)(9) —S(O)ₓ—R¹¹, in which x is the integer zero, 1, or 2;
  (5)(10) —C(O)—O—R¹¹;
  (5)(11) —C(O)—N(R¹¹)₂;
  (5)(12) —N(R¹¹)₂;
  (5)(13) (C₃–C₆)-cycloalkyl;
  (5)(14) a radical of formula

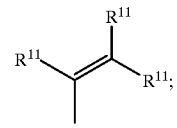

or
  (5)(15) a radical of formula

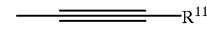

in which
R[11] is
(a) hydrogen;
(b) ($C_1$–$C_6$)-alkyl, in which alkyl is unsubstituted or mono-, di-, or trisubstituted independently of one another by
(1) aryl, in which aryl is unsubstituted or substituted;
(2) heteroaryl having 5 to 14 ring members, in which heteroaryl is unsubstituted or substituted;
(3) a heterocycle having 5 to 12 ring members, in which heterocycle is unsubstituted or substituted;
(4) halogen;
(5) —N—($C_1$–$C_6$)$_n$-alkyl, in which n is the integer 0, 1, or 2 and alkyl is unsubstituted or mono-, di-, or trisubstituted independently of one another by halogen or by —COOH;
(6) —O—($C_1$–$C_6$)-alkyl; or
(7) —COOH;
(c) aryl, in which aryl is unsubstituted or substituted;
(d) heteroaryl having 5 to 14 ring members, in which heteroaryl is unsubstituted or substituted; or
(e) a heterocycle having 5 to 12 ring members, in which heterocycle is unsubstituted or substituted; and
in the case of (R[11])$_2$, R[11] independently of one another has the meaning of (a) to (e);
Z is
(1) aryl, in which aryl is unsubstituted or substituted;
(2) heteroaryl having 5 to 14 ring members, in which heteroaryl is unsubstituted or substituted
(3) a heterocycle having 5 to 12 ring members, in which heterocycle is unsubstituted or substituted;
(4) ($C_1$–$C_6$)-alkyl, in which alkyl is substituted or unsubstituted independently of one another by
(4)(1) aryl, in which aryl is unsubstituted or substituted;
(4)(2) heteroaryl having 5 to 14 ring members, in which heteroaryl is unsubstituted or substituted;
(4)(3) a heterocycle having 5 to 12 ring members, in which heterocycle is unsubstituted or substituted;
(4)(4) halogen;
(4)(5) —N—($C_1$–$C_6$)$_n$-alkyl, in which n is the integer 0, 1, or 2, and alkyl is unsubstituted or mono-, di-, or trisubstituted independently of one another by halogen or by —COOH;
(4)(6) —O—($C_1$–$C_6$)-alkyl; or
(4)(7) —COOH; or
(5) —C(O)—R[10], in which
R[10] is
(1) —O—R[11]; or
(2) —N(R[11])$_2$;
in which R[11] is as defined above; or
R[8] and R[9], together with the nitrogen and carbon to which they are each bonded, form a heterocyclic ring of formula IIa

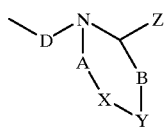

IIa in which:
D, Z, and R[10] are as defined in formula II;
A is nitrogen or —CH$_2$—;
B is oxygen, sulfur, nitrogen, or —CH$_2$;
X is oxygen, sulfur, nitrogen, or —CH$_2$;
Y is absent or is oxygen, sulfur, nitrogen, or —CH$_2$—; or
X and Y together form a phenyl, 1,2-diazine, 1,3-diazine, or a 1,4-diazine radical;
where the ring system formed by N, A, X, Y, B, and the carbon contains no more than one oxygen, X is not oxygen, sulfur, or nitrogen if A is a nitrogen atom; contains no more than one sulfur; contains 1, 2, 3, or 4 nitrogens; and where oxygen and sulfur do not occur at the same time;
where the ring system formed by N, A, X, Y, B, and the carbon is unsubstituted or mono-, di-, or trisubstituted independently of one another by ($C_1$–$C_8$)-alkyl, in which alkyl is unsubstituted or mono- or disubstituted by
(1)(1) —OH;
(1)(2) ($C_1$–$C_8$)-alkoxy, in which alkoxy is straight-chain or branched;
(1)(3) halogen;
(1)(4) —NO$_2$;
(1)(5) —NH$_2$;
(1)(6) —CF$_3$;
(1)(7) —OH;
(1)(8) methylenedioxy;
(1)(9) —C(O)—CH$_3$;
(1)(10) —CH(O);
(1)(11) —CN;
(1)(12) —COOH;
(1)(13) —C(O)—NH$_2$;
(1)(14) ($C_1$–$C_4$)-alkoxycarbonyl, in which alkoxycarbonyl is straight-chain or branched;
(1)(15) phenyl;
(1)(16) phenoxy;
(1)(17) benzyl;
(1)(18) benzyloxy; or
(1)(19) tetrazolyl; or
R[9] and Z together with the carbons to which they each are bonded form a heterocyclic ring of formula IIc

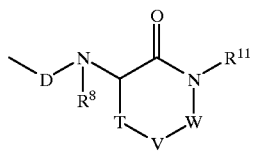

IIc in which:
D, R[8], and R[11] are as defined in formula II;
T is oxygen, sulfur, nitrogen, or —CH$_2$—;
W is oxygen, sulfur, nitrogen, or —CH$_2$—;
V is absent or is oxygen, sulfur, nitrogen, or —CH$_2$; or
T and V together form a phenyl, 1,2-diazine, 1,3-diazine, or a 1,4-diazine radical; or

137

V and W together form a phenyl, 1,2-diazine, 1,3-diazine, or a 1,4-diazine radical;

where the ring system formed by N, T, V, W, and the two carbons contains no more than one oxygen, no more than one sulfur, and 1, 2, 3, or 4 nitrogens; where oxygen and sulfur do not occur at the same time; and where the ring system formed by N, T, V, W, and the two carbons is unsubstituted or mono-, di-, or trisubstituted independently of one another by the substituents defined above under (1)(1) to (1)(19); and the other substituents $R^1$, $R^2$, $R^3$, and $R^4$ are chosen independently of one another, and are (1) hydrogen;

(2) halogen;

(3) $(C_1-C_4)$-alkyl;

(4) heteroaryl having 5 to 14 ring members, in which heteroaryl is unsubstituted or substituted;

(5) a heterocycle having 5 to 12 ring members, in which heterocycle is unsubstituted or substituted;

(6) $(C_1-C_6)$-alkyl;

(7) —CN;

(8) —$NO_2$;

(9) —O—$(C_0-C_4)$-alkyl-aryl, in which alkyl is straight-chain or branched;

(10) —O—$(C_1-C_4)$-alkyl;

(11) —$OR^{11}$;

(12) —$N(R^{11})_2$;

(13) —$S(O)_xR^{11}$, in which x is the integer 0, 1, or 2; or

(14) —$CF_3$;

in which $R^{11}$ is as defined above;

$R^5$ is (1) hydrogen;

(2) —OH; or (3) =O; and $R^6$ is (1) aryl, in which aryl is unsubstituted or substituted, and is selected from phenyl, naphthyl, biphenylyl, anthryl, and fluorenyl, in which aryl is unsubstituted, monosubstituted, or polysubstituted independently of one another by $(C_1-C_8)$-alkyl, $(C_1-C_8)$-alkoxy, halogen, nitro, amino, trifluoromethyl, hydroxyl, hydroxy-$(C_1-C_4)$-alkyl, methylenedioxy, ethylenedioxy, formyl, acetyl, cyano, hydroxycarbonyl, aminocarbonyl, $(C_1-C_4)$-alkoxycarbonyl, phenyl, phenoxy, benzyl, benzyloxy, and tetrazolyl; or (2) heteroaryl having 5 to 14 ring members, unsubstituted or mono-, di-, or trisubstituted; or (3) a heterocycle having 5 to 12 ring members, unsubstituted or mono-, di-, or trisubstituted.

27. A method for treating rheumatoid arthritis, osteoarthritis, asthma, cardiac infaret, Alzheimer's disease, carcinomatous disorders, or atherosclerosis, comprising administering to a patient in need thereof an effective amount of at least one compound of formula I

138

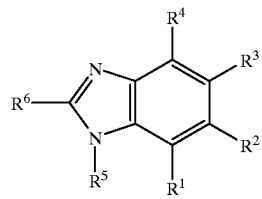

I or a stereoisomeric form of the compound of formula I or a physiologically tolerable salt of the compound of formula I, where at least one of the substituents $R^1$, $R^2$, $R^3$, and $R^4$ is a radical of formula II

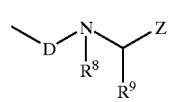

II in which:

D is —C(O)—, —S(O)—, or —$S(O)_2$—;

$R^8$ is hydrogen or $(C_1-C_4)$-alkyl;

$R^9$ is (1) glycine, alanine, valine, leucine, isoleucine, phenylalanine, tyrosine, tryptophan, serine, threonine, cysteine, methionine, asparagine, glutamine, lysine, histidine, arginine, glutamic acid, aspartic acid, 2-aminoadipic acid, 2-aminobutyric acid, 2-aminoisobutyric acid, 2,3-diaminopropionic acid, 2,4-diaminobutyric acid, 1,2,3,4-tetrahydroisoquinoline-1-carboxylic acid, 1,2,3,4-tetrahydroisoquinoline-3-carboxylic acid, 2-aminopimelic acid, 2-amino-3-phenylaminoethyl-propionic acid, 2-amino-3-phenylamino-propionic acid, phenylglycine, 3-(2-thienyl)alanine, 3-(3-thienyl) alanine, 2-(2-thienyl)glycine, 2-aminoheptanoic acid, pipecolic acid, hydroxylysine, sarcosine, N-methylisoleucine, 6-N-methyllysine, N-methylvaline, norvaline, norleucine, ornithine, allo-isoleucine, allo-threonine, allo-hydroxylysine, 4-hydroxyproline, 3-hydroxyproline, 3-(2-naphthyl) alanine, 3-(1-naphthylalanine), homophenylalanine, homocysteine, homocysteic acid, homotryptophan, cysteic acid, 3-(2-pyridyl)alanine, 3-(3-pyridyl) alanine, 3-(4-pyridyl)alanine, phosphinothricin, 4-fluorophenylalanine, 3-fluorophenylalanine, 4-fluorophenylalanine, 3-fluorophenylalanine, 3-fluorophenylalanine, 2-fluorophenylalanine, 4-chlorophenylalanine, 4-nitrophenylalanine, 4-aminophenylalanine, cyclohexylalanine, citrulline, 5-fluorotryptophan, 5-methoxytryptophan, methionine sulfone, methionine sulfoxide, or —NH—$NR^{11}$—CON $(R^{11})_2$, wherein $R^{11}$ is as defined below;

(2) aryl, in which aryl is unsubstituted or substituted;

(3) heteroaryl having 5 to 14 ring members, in which heteroaryl is unsubstituted or substituted;

(4) a heterocycle having 5 to 12 ring members, in which heterocycle is unsubstituted or substituted:

(5) $(C_1-C_6)$-alkyl, in which alkyl is unsubstituted or mono-, di-, or trisubstituted independently of one another by (5)(1) aryl, in which aryl is unsubstituted or substituted;

(5)(2) heteroaryl having 5 to 14 ring members, in which heteroaryl is unsubstituted or substituted;

(5)(3) a heterocycle having 5 to 12 ring members, in which the heterocycle is unsubstituted or substituted;
(5)(4) —O—R$^{11}$;
(5)(5) =O;
(5)(6) halogen;
(5)(7) —CN;
(5)(8) —CF$_3$;
(5)(9) —S(O)$_x$—R$^{11}$, in which x is the integer zero, 1, or 2;
(5)(10) —C(O)—O—R$^{11}$;
(5)(11) —C(O)—N(R$^{11}$)$_2$;
(5)(12) —N(R$^{11}$)$_2$;
(5)(13) (C$_3$–C$_6$)-cycloalkyl;
(5)(14) a radical of formula

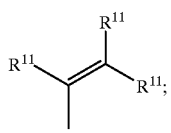

or
(5)(15) a radical of formula

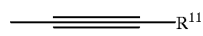

in which
R$^{11}$ is
(a) hydrogen;
(b) (C$_1$–C$_6$)-alkyl, in which alkyl is unsubstituted or mono-, di-, or trisubstituted independently of one another by
(1) aryl, in which aryl is unsubstituted or substituted;
(2) heteroaryl having 5 to 14 ring members, in which heteroaryl is unsubstituted or substituted;
(3) a heterocycle having 5 to 12 ring members, in which heterocycle is unsubstituted or substituted;
(4) halogen;
(5) —N—(C$_1$–C$_6$)$_n$-alkyl, in which n is the integer 0, 1, or 2 and alkyl is unsubstituted or mono, di-, or trisubstituted independently of one another by halogen or by —COOH;
(6) —O—(C$_1$–C$_6$)-alkyl; or
(7) —COOH;
(c) aryl, in which aryl is unsubstituted or substituted;
(d) heteroaryl having 5 to 14 ring members, in which heteroaryl is unsubstituted or substituted; or
(e) a heterocycle having 5 to 12 ring members, in which heterocycle is unsubstituted or substituted; and
in the case of (R$^{11}$)$_2$, R$^{11}$ independently of one another has the meaning of (a) to (e);
Z is
(1) aryl, in which aryl is unsubstituted or substituted;
(2) heteroaryl having 5 to 14 ring members, in which heteroaryl is unsubstituted or substituted:
(3) a heterocycle having 5 to 12 ring members, in which heterocycle is unsubstituted or substituted;
(4) —(C$_1$–C$_6$)-alkyl, in which alkyl is substituted or unsubstituted independently of one another by (4)(1) aryl, in which aryl is unsubstituted or substituted;
(4)(2) heteroaryl having 5 to 14 ring members, in which heteroaryl is unsubstituted or substituted;
(4)(3) a heterocycle having 5 to 12 ring members, in which heterocycle is unsubstituted or substituted;
(4)(4) halogen;
(4)(5) —N—(C$_1$–C$_6$)$_n$-alkyl, in which n is the integer 0, 1, or 2, and alkyl is unsubstituted or mono-, di-, or trisubstituted independently of one another by halogen or by —COOH;
(4)(6) —O—(C$_1$–C$_6$)-alkyl; or
(4)(7) —COOH; or
(5) —C(O)—R$^{10}$, in which
R$^{10}$ is
(1) —O—R$^{11}$; or
(2) —N(R$^{11}$)$_2$;
which R$^{11}$ is as defined above; or
R$^8$ and R$^9$, together with the nitrogen and carbon to which they are each bonded, form a heterocyclic ring of formula IIa

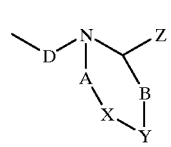

in which:
D, Z, and R$^{10}$ are as defined in formula II;
A is nitrogen or —CH$_2$—;
B is oxygen, sulfur, nitrogen, or —CH$_2$;
X is oxygen, sulfur, nitrogen, or —CH$_2$;
Y is absent or is oxygen, sulfur, nitrogen, or —CH$_2$—; or
X and Y together form a phenyl, 1,2-diazine, 1,3-diazine, or a 1,4-diazine radical;
where the ring system formed by N, A, X, Y, B, and the carbon contains no more than one oxygen, X is not oxygen, sulfur, or nitrogen if A is a nitrogen atom; contains no more than one sulfur; contains 1, 2, 3, or 4 nitrogens; and where oxygen and sulfur do not occur at the same time;
where the ring system formed by N, A, X, Y, B, and the carbon is unsubstituted or mono-, di-, or trisubstituted independently of one another by (C$_1$–C$_8$)-alkyl, in which alkyl is unsubstituted or mono- or disubstituted by
(1)(1) —OH;
(1)(2) (C$_1$–C$_8$)-alkoxy, in which alkoxy is straight-chain or branched;
(1)(3) halogen;
(1)(4) —NO$_2$;
(1)(5) —NH$_2$;
(1)(6) —CF$_3$;
(1)(7) —OH;
(1)(8) methylenedioxy;
(1)(9) —C(O)—CH$_3$;
(1)(10) —CH(O);
(1)(11) —CN;
(1)(12) —COOH;
(1)(13) —C(O)—NH$_2$;
(1)(14) (C$_1$–C$_4$)-alkoxycarbonyl, in which alkoxycarbonyl is straight-chain or branched;
(1)(15) phenyl;
(1)(16) phenoxy;
(1)(17) benzyl;

(1)(18) benzyloxy; or
(1)(19) tetrazolyl; or $R^9$ and Z together with the carbons to which they each are bonded form a heterocyclic ring of formula IIc

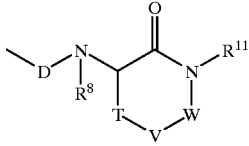

IIc in which:
D, $R^8$, and $R^{11}$ are as defined in formula II;
T is oxygen, sulfur, nitrogen, or —$CH_2$—;
W is oxygen, sulfur, nitrogen, or —$CH_2$—;
V is absent or is oxygen, sulfur, nitrogen, or —$CH_2$—; or
T and V together form a phenyl, 1,2-diazine, 1,3-diazine, or a 1,4-diazine radical; or
V and W together form a phenyl, 1,2-diazine, 1,3-diazine, or a 1,4-diazine radical;
  where the ring system formed by N, T, V, W, and the two carbons contains no more than one oxygen, no more than one sulfur, and 1, 2, 3, or 4 nitrogens; where oxygen and sulfur do not occur at the same time; and where the ring system formed by N, T, V, W, and the two carbons is unsubstituted or mono-, di-, or trisubstituted independently of one another by the substituents defined above under (1)(1) to (1)(19); and
  the other substituents $R^1$, $R^2$, $R^3$, and $R^4$ are chosen independently of one another, and are
    (1) hydrogen;
    (2) halogen;
    (3) ($C_1$-$C_4$)-alkyl;
    (4) heteroaryl having 5 to 14 ring members, in which heteroaryl is unsubstituted or substituted:
    (5) a heterocycle having 5 to 12 ring members, in which heterocycle is unsubstituted or substituted;
    (6) ($C_1$-$C_6$)-alkyl;
    (7) —CN;
    (8) —$NO_2$;
    (9) —O—($C_0$-$C_4$)-alkyl-aryl, in which alkyl is straight-chain or branched;
    (10) —O—($C_1$-$C_4$)-alkyl;
    (11) —$OR^{11}$;
    (12) —$N(R^{11})_2$;
    (13) —$S(O)_xR^{11}$, in which x is the integer 0, 1, or 2; or
    (14) —$CF_3$;
      in which $R^{11}$ is as defined above;
$R^5$ is
    (1) hydrogen;
    (2) —OH; or
    (3) =O; and
$R^6$ is
    (1) phenyl, optionally mono- or disubstituted independently of one another by —CN, —$NO_2$, —O—($C_1$-$C_4$)-alkyl, —$N(R^{11})_2$, —NH—C(O)—$R^{11}$, —$S(O)_xR^{11}$, in which x is the integer 0, 1, or 2, —C(O)—$R^{11}$, in which $R^{11}$ is as defined above, or —($C_1$-$C_4$)-alkyl-$NH_2$; or
    (2) heteroaryl having 5 to 14 ring members, unsubstituted or mono-, di-, or trisubstituted; or
    (3) a heterocycle having 5 to 12 ring members, unsubstituted or mono-, di-, or trisubstituted.

28. The method of claim 27, comprising administering to a patient in need thereof an effective amount of at least one compound of formula I, in which:
$R^8$ is hydrogen;
$R^9$ is
    (1) glycine, alanine, valine, leucine, isoleucine, phenylalanine, tyrosine, tryptophan, serine, threonine, cysteine, methionine, asparagine, glutamine, lysine, histidine, arginine, glutamic acid, aspartic acid, 2-aminoadipic acid, 2-aminobutyric acid, 2-aminoisobutyric acid, 2,3-diaminopropionic acid, 2,4-diaminobutyric acid, 1,2,3,4-tetrahydroisoquinoline-1-carboxylic acid 1,2,3,4-tetrahydroisoquinoline-3-carboxylic acid, 2-aminopimelic acid, 2-amino-3-phenylaminoethyl-propionic acid, 2-amino-3-phenylamino-propionic acid, phenylglycine, 3-(2-thienyl)alanine, 3-(3-thienyl)alanine, 2-(2-thienyl)glycine, 2-aminoheptanoic acid, pipecolic acid, hydroxylysine, sarcosine, N-methylisoleucine, 6-N-methyllysine, N-methylvaline, norvaline, norleucine, ornithine, allo-isoleucine, allo-threonine, allo-hydroxylysine, 4-hydroxyproline, 3-hydroxyproline, 3-(2-naphthyl)alanine, 3-(1-naphthylalanine), homophenylalanine, homocysteine, homocysteic acid, homotryptophan, cysteic acid, 3-(2-pyridyl)alanine, 3-(3-pyridyl)alanine, 3-(4-pyridyl)alanine, phosphinothricin, 4-fluorophenylalanine, 3-fluorophenylalanine, 4-fluorophenylalanine, 3-fluorophenylalanine, 3-fluorophenylalanine, 2-fluorophenylalanine, 4-chlorophenylalanine, 4-nitrophenylalanine, 4-aminophenylalanine, cyclohexylalanine, citrulline, 5-fluorotryptophan, 5-methoxytryptophan, methionine sulfone, methionine sulfoxide, or —NH—$NR^{11}$—$CON(R^{11})_2$, wherein $R^{11}$ is as defined below;
    (2) ($C_1$-$C_6$)-alkyl, in which alkyl is unsubstituted or mono- or disubstituted independently of one another by a radical selected from pyrrole, pyrrole mono- or disubstituted independently of one another by —($C_1$-$C_4$)-alkyl, pyrazole, phenyl, imidazole, triazole, thiophene, thiazole, oxazole, isoxazole, pyridine, pyrimidine, indole, benzothiophene, benzimidazole, benzoxazole, benzothiazole, azetidine, pyrroline, pyrrolidine, piperidine, isothiazole, diazepine, thiomorpholine, —CN, morpholine, azepine, 1,3,4-oxadiazole, —$N(R^{13})$-phenyl, wherein $R^{13}$ is defined below, pyrazine, ($C_3$-$C_6$)-cycloalkyl, —$OR^{11}$, —$NH(R^{11})$, in which $R^{11}$ is as defined above, —$S(O)_x$—$R^{12}$, in which x is 0, 1, or 2, and $R^{12}$ is naphthyl, pyrimidinyl, morpholinyl, or phenyl, which are unsubstituted or mono- or disubstituted independently of one another by —OH, ($C_1$-$C_4$)-alkyl, —$CF_3$, halogen, —O—($C_1$-$C_4$)-alkyl, —COOH, —C(O)—O—($C_1$-$C_4$)-alkyl, —$NH_2$, or —NH—C(O)—($C_1$-$C_4$)-alkyl, or C(O)—$R^{12}$, in which $R^{12}$ is as defined above;
Z is —C(O)—$R^{10}$, tetrazole, ($C_1$-$C_6$)-alkyl, in which alkyl is unsubstituted or mono- or disubstituted independently of one another by phenyl or —OH, or 1,3,4-oxadiazole, in which 1,3,4-oxadiazole is unsubstituted or monosubstituted by
    —$NH_2$, —$NH(C_1$-$C_4)$-alkyl, —N—[($C_1$-$C_4$)-alkyl]$_2$, —NH—C(O)—($C_1$-$C_4$)-alkyl, —NH—C(O)—NH—($C_1$-$C_4$)-alkyl, —NH—C(O)—NH—($C_3$-$C_7$)-cycloalkyl, —NH—C(O)—NH-aryl, —NH—C(O)—NH-phenyl, —NH—$SO_2$-aryl, —NH—SO$_2$—(C$_1$–C$_4$)-alkyl, —OH, or —(C$_1$–C$_4$)-alkyl, in which
R$^{10}$ is —O—R$^{11}$, phenyl, pyrimidine, —OH, morpholinyl, —N(R$^{11}$)$_2$, or —NH$_2$;
R$^{11}$ is
  (1) —(C$_1$–C$_4$)-alkyl;
  (2) R$^{13}$; or
  (3) —N(R$^{13}$)$_2$, in which
    R$^{13}$ independently of one another is
      (a) hydrogen;
      (b) —(C$_1$–C$_6$)-alkyl;
      (c) —(C$_1$–C$_4$)-alkyl-O—(C$_1$–C$_4$)-alkyl;
      (d) —(C$_1$–C$_6$)alkyl-N(R$^{13}$)$_2$;
      (e) halogen; or
      (f) —(C$_0$–C$_4$)-alkyl, mono- or disubstituted by aryl, imidazolyl, morpholinyl, or phenyl; or
R$^8$ and R$^9$, together with the nitrogen and carbon to which they are each bonded, form a ring of formula IIa selected from pyrrole, pyrroline, pyrrolidine, pyridine, piperidine, piperylene, pyridazine, pyrimidine, pyrazine, piperazine, pyrazole, imidazole, pyrazoline, imidazoline, pyrazolidine, imidazolidine, oxazole, isoxazole, 2-isoxazolidine, isoxazolidine, morpholine, isothiazole, thiazole, tetrazole, 1,2,3,5-oxathiadiazole-2-oxides, oxadiazolones, isoxazolones, triazolones, oxadiazolidinediones, triazoles which are substituted by F, CN, CF$_3$, or COO—(C$_1$–C$_4$)-alkyl, 3-hydroxypyrrole-2,4-diones, 5oxo-1,2,4-thiadiazoles, 1,3,4-oxadiazole, isothiazolidine, thiomorpholine, indazole, thiadiazole, benzimidazole, quinoline, triazole, phthalazine, quinazoline, quinoxaline, purine, pteridine, indole, tetrahydroquinoline, tetrahydroisoquinoline, and isoquinoline; or
R$^9$ and Z, together with the carbons to which they are each bonded, form a ring of formula IIc selected from pyrrole, pyrroline, pyrrolidine, pyridine, piperidine, piperylene, pyridazine, pyrimidine, pyrazine, piperazine, pyrazole, imidazole, pyrazoline, imidazoline, pyrazolidine, imidazolidine, oxazole, isoxazole, 2-isoxazolidine, isoxazolidine, morpholine, isothiazole, thiazole, isothiazolidine, thiomorpholine, indazole, thiadiazole, benzimidazole, quinoline, triazole, phthalazine, quinazoline, quinoxaline, purine, pteridine, indole, tetrahydroquinoline, tetrahydroisoquinoline, isoquinoline, tetrazole, 1,2,3,5-oxathiadiazole-2-oxides, oxadiazolones, isoxazolones, triazolones, oxadiazolidinediones, triazoles which are substituted by F, CN, CF$_3$, or COO—(C$_1$–C$_4$)-alkyl, 3-hydroxypyrrole-2,4-diones, 1,3,4-oxadiazole, and 5oxo-1,2,4-thiadiazoles; and
the other substituents R$^1$, R$^2$, R$^3$, and R$^4$ are chosen independently of one another, and are
  (1) hydrogen;
  (2) halogen;
  (3) (C$_1$–C$_4$)-alkyl;
  (4) —CN;
  (5) —NO$_2$;
  (6) —O—(C$_0$–C$_4$)-alkyl-aryl, in which alkyl is straight-chain or branched;
  (7) —O—(C$_1$–C$_4$)-alkyl;
  (8) —N—(C$_0$–C$_4$)-alkyl-aryl, in which alkyl is straight-chain or branched;
  (9) —N—(C$_1$–C$_4$)-alkyl; or
  (10) —CF$_3$;
R$^5$ is
  (1) hydrogen;
  (2) —OH; or
  (3) =O; and
R$_6$ is
  (1) phenyl, mono- or disubstituted independently of one another by
    (1)(1) —CN;
    (1)(2) —NO$_2$;
    (1)(3) —O—(C$_1$–C$_4$)-alkyl;
    (1)(4) —NH$_2$; or
    (1)(5) —(C$_1$–C$_4$)-alkyl-NH$_2$; or
  (2) heteroaryl having 5 to 14 ring members, in which the heteroaryl is unsubstituted or mono-, di-, or trisubstituted independently of one another by —N—R$^4$, in which R$^{14}$ is —(C$_1$–C$_6$)-alkyl, —(C$_3$–C$_8$)-cycloalkyl, or phenyl, halogen, OH, or —(C$_1$–C$_4$)-alkyl; or
  (3) a heterocycle having 5 to 12 ring members, in which the heterocycle is unsubstituted or mono-, di-, or trisubstituted independently of one another by —N—R$_{14}$, in which R$^{14}$ is —(C$_4$C$_8$)-alkyl, —(C$_3$C$_8$)-cycloalkyl, or phenyl, halogen, —OH, or (C$_1$–C$_4$)-alkyl.

\* \* \* \* \*

UNITED STATES PATENT AND TRADEMARK OFFICE
CERTIFICATE OF CORRECTION

PATENT NO.   : 6,358,978 B1
DATED        : March 19, 2002
INVENTOR(S)  : Olaf Ritzeler et al.

It is certified that error appears in the above-identified patent and that said Letters Patent is hereby corrected as shown below:

<u>Title page,</u>
Item [75], Inventors, "Frankurt" should read -- Frankfurt --.

<u>Column 109,</u>
Line 56, "below:" should read -- below; --.

<u>Column 110,</u>
Lines 48-49, "substituted:" should read -- substituted; --.

<u>Column 111,</u>
Line 5, "heteroarl" should read -- heteroaryl --.

<u>Column 112,</u>
Line 52, "unsubstitued" should read -- unsubstituted --.

<u>Column 113,</u>
Line 14, "hydroxytarbonyl" should read -- hydroxycarbonyl --.
Line 27, "quinoitne" should read -- quinoline --.

<u>Column 114,</u>
Line 10, "homacysteic" should read -- homocysteic --.

<u>Column 117,</u>
Line 15, before "halogen", "(4)" should read -- (2) --.
Line 16, "(5)" should read -- (3) --; and "($C_1$-$C_4$-alkyl" should read -- ($C_1$-$C_4$)-alkyl --.
Line 30, before "-$S(O)_xR^{11}$", insert -- (13) --.
Lines 58, 63 and 66, "claim 1 or 2" should read -- claims 1 or 2 --.

<u>Column 118,</u>
Lines 9, 14 and 26, "claim 1 or 2" should read -- claims 1 or 2 --.
Lines 34 and 39, "claim 1 or 2" should read -- claims 1 or 2 --.
Lines 40-41, "claim 1 or 2" should read -- claims 1 or 2 --.

<u>Column 120,</u>
Line 25, "claim 1 or 2" should read -- claims 1 or 2 --.

UNITED STATES PATENT AND TRADEMARK OFFICE
CERTIFICATE OF CORRECTION

PATENT NO.     : 6,358,978 B1
DATED          : March 19, 2002
INVENTOR(S)    : Olaf Ritzeler et al.

It is certified that error appears in the above-identified patent and that said Letters Patent is hereby corrected as shown below:

Column 121,
Line 50, "tetrahydrolsoquinoline" should read -- tetrahydroisoquinoline --.

Column 123,
Line 25, "$(C_1-C_4)$alkyl" should read -- $(C_1-C_4)$-alkyl --.
Line 29, "lyslne" should read -- lysine --.

Column 124,
Line 13, "$(C_3-C_8)$-cycloalkyl" should read -- $(C_3-C_6)$-cycloalkyl --.
Line 48, "-O-$(C_1-C_5)$-alkyl" should read -- -O-$(C_1-C_6)$-alkyl --.

Column 126,
Line 29, "mono" should read -- mono- --.

Column 127,
Line 8, after "activity of", insert -- NFκB --.
Line 24, "$R_1$" should read -- $R^1$ --.

Column 128,
Line 56, "-O-$(C_1-C_6)$-alkyl" should read -- -O-$(C_1-C_6)$-alkyl --.

Column 130,
Line 24, "which;" should read -- which: --.

Column 132,
Line 1, "-(C(O)-$R_{10}$" should read -- -C(O)-$R^{10}$ --.
Lines 6-7, "-N-[$(C_{193}-C_4)$-alkyl] $_2$" should read -- -N-[$(C_1-C_4)$-alkyl]$_2$ --.

Column 133,
Line 1, "-O-$(C_0-C_4)$alkyl-aryl" should read -- -O-$(C_0-C_4)$-alkyl-aryl --.
Line 65, "systeine" should read -- cysteine --.

Column 135,
Line 40, after "substituted", insert -- ; --.
Line 43, "$(C_1-C_6)$-alkyl" should read -- -$(C_1-C_6)$-alkyl --.

Column 137,
Line 40, "$R^5$is" should read -- $R^5$ is --.
Line 64, "infaret" should read -- infarct --.

UNITED STATES PATENT AND TRADEMARK OFFICE
CERTIFICATE OF CORRECTION

PATENT NO.   : 6,358,978 B1
DATED        : March 19, 2002
INVENTOR(S)  : Olaf Ritzeler et al.

It is certified that error appears in the above-identified patent and that said Letters Patent is hereby corrected as shown below:

Column 139,
Line 45, "mono" should read -- mono- --.
Line 63, "substituted:" should read -- substituted; --.

Column 140,
Line 17, before "which", insert -- in --.

Column 141,
Line 38, "substituted:" should read -- substituted; --.

Column 142,
Line 13, after "tetrahydroisoquinoline-1-carboxylic acid", insert a comma.

Column 143,
Line 13, "-($C_1$-$C_6$)alkyl-N($R^{13}$)$_2$" should read -- -($C_1$-$C_6$)-alkyl-N($R^{13}$)$_2$ --.
Line 28, "5oxo-1,2,4-thiadiazoles" should read -- 5-oxo-1,2,4-thiadiazoles --.

Column 144,
Line 5, "5oxo-1,2,4-thiadiazoles" should read -- 5-oxo-1,2,4-thiadiazoles --.
Line 24, "$R_6$" should read -- $R^6$ --.
Line 35, "-N-$R^4$" should read -- -N-$R^{14}$ --.
Line 36, "-($C_3$-$C_8$)-cycloalkyl" should read -- -($C_3$-$C_6$)-cycloalkyl --.
Line 41, "-N-$R_{14}$" should read -- -N-$R^{14}$ --; and "-($C_4C_8$)-alkyl" should read -- -($C_1$-$C_6$)-alkyl --.
Line 42, "-($C_3C_8$)-cycloalkyl" should read -- -($C_3$-$C_6$)-cycloalkyl --.
Line 43, "($C_1$-$C_4$)-alkyl" should read -- -($C_1$-$C_4$)-alkyl --.

Signed and Sealed this

Twenty-fifth Day of March, 2003

JAMES E. ROGAN
*Director of the United States Patent and Trademark Office*